United States Patent
Chao-Shern et al.

(10) Patent No.: US 11,525,160 B2
(45) Date of Patent: Dec. 13, 2022

(54) METHODS FOR MULTIPLEX DETECTION OF ALLELES ASSOCIATED WITH OPHTHALMIC CONDITIONS

(71) Applicant: AVELLINO LAB USA, INC., Menlo Park, CA (US)

(72) Inventors: Connie Chao-Shern, Menlo Park, CA (US); Sun-Young Cho, Seoul (KR); Gene Lee, Burlingame, CA (US)

(73) Assignee: Avellino Lab USA, Inc., Menlo Park, CA (US)

( * ) Notice: Subject to any disclaimer, the term of this patent is extended or adjusted under 35 U.S.C. 154(b) by 0 days.

(21) Appl. No.: 15/154,895

(22) Filed: May 13, 2016

(65) Prior Publication Data

US 2016/0319357 A1 Nov. 3, 2016

Related U.S. Application Data

(63) Continuation of application No. PCT/US2014/065975, filed on Nov. 17, 2014.

(60) Provisional application No. 61/905,051, filed on Nov. 15, 2013.

(51) Int. Cl.
| | | |
|---|---|---|
| *C12Q 1/68* | (2018.01) | |
| *C12Q 1/6883* | (2018.01) | |
| *C12Q 1/6851* | (2018.01) | |

(52) U.S. Cl.
CPC ......... *C12Q 1/6883* (2013.01); *C12Q 1/6851* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,018,713 A | 1/2000 | Coli et al. | |
| 6,171,112 B1 | 1/2001 | Clark et al. | |
| 6,331,276 B1 | 12/2001 | Takei et al. | |
| 9,938,581 B2 | 4/2018 | Lee et al. | |
| 2003/0176650 A1 | 9/2003 | Grosse et al. | |
| 2003/0204418 A1 | 10/2003 | Ledley | |
| 2003/0211500 A1 | 11/2003 | Woosley | |
| 2004/0217345 A1 | 11/2004 | Boland et al. | |
| 2004/0263853 A1 | 12/2004 | Hill et al. | |
| 2005/0019757 A1 | 1/2005 | Stolarchuk | |
| 2006/0038990 A1 | 2/2006 | Habib et al. | |
| 2006/0057604 A1 | 3/2006 | Chen et al. | |
| 2006/0066249 A1 | 3/2006 | Wark et al. | |
| 2007/0254296 A1 | 11/2007 | Jiang et al. | |
| 2007/0274895 A1 | 11/2007 | Jesih et al. | |
| 2008/0113344 A1 | 5/2008 | Wirtz et al. | |
| 2008/0174775 A1 | 7/2008 | Moskovits et al. | |
| 2008/0267946 A1 | 10/2008 | Kim et al. | |
| 2009/0073447 A1 | 3/2009 | Dahint et al. | |
| 2009/0305394 A1* | 12/2009 | Lee ..................... | C12Q 1/6883 435/287.2 |
| 2010/0190158 A1 | 7/2010 | Peitz et al. | |
| 2011/0053794 A1 | 3/2011 | Zhang | |
| 2012/0077200 A1 | 3/2012 | Lee et al. | |
| 2012/0231537 A1 | 9/2012 | Templeton et al. | |
| 2013/0302811 A1 | 11/2013 | Lee et al. | |

FOREIGN PATENT DOCUMENTS

| | | |
|---|---|---|
| CN | 101144812 A | 3/2008 |
| CN | 101374850 A | 2/2009 |
| CN | 102459593 A | 5/2012 |
| EP | 1715326 A1 | 10/2006 |
| EP | 1 964 606 A1 | 9/2008 |
| EP | 2 019 309 A2 | 1/2009 |
| EP | 2420574 A1 | 2/2012 |
| JP | 2006-250668 A | 9/2006 |
| JP | 2009-045057 A | 3/2009 |
| JP | 2009-523442 A | 6/2009 |
| JP | 2012-523831 A | 11/2012 |
| KR | 10-2007-0076532 A | 7/2007 |
| WO | WO 00/58509 A2 | 10/2000 |
| WO | WO2005/015198 A1 | 2/2005 |
| WO | WO2005/040756 A2 | 5/2005 |
| WO | WO 2005/114298 A2 | 12/2005 |

(Continued)

OTHER PUBLICATIONS

Yoo et al. Anal. Chem. 2010, 82, 1349-1357 (Year: 2010).*
New England Biolabs Catalog (1996/1997), pp. 111 (Year: 1996).*
Afshari, N., et al., "'Survey of Patients With Granular, Lattice, Avellino, and Reis-Buecklers Corneal Dystrophies for Mutations in the BIGH3 and Gelsolin Genes'", Arch Ophthalmol, Jan. 2001, pp. 16-22, vol. 119.
Armelao, L, et al., "Innovative metal oxide-based substrates for DNA Microarrays," Inorganica Chimica Acta, Apr. 10, 2008, vol. 361, No. 12-13, pp. 3603-3608.
Avellino Co. Ltd., Certificate of Patent, JP 2012-505796, dated May 1, 2015, 2 pgs.
Avellino Co. Ltd., European Search Report, EP 14186678.0, dated Feb. 18, 2015, 5 pgs.

(Continued)

*Primary Examiner* — Juliet C Switzer
(74) *Attorney, Agent, or Firm* — Morgan, Lewis & Bockius LLP

(57) ABSTRACT

Systems and methods for detecting at least two genomic alleles associated with corneal dystrophy in a sample from a human subject are disclosed in which cells (e.g., epithelial) of the subject are adhered to a tip of a substrate. The tip of the substrate is agitated in a lysis solution that lyses cells adhered to the substrate. The substrate is removed from the lysis solution upon completion of this agitation. The resulting lysis solution is incubated and then genomic DNA from the lysis solution is isolated to form a gDNA solution. From this, identity of at least two nucleotides present in the human TGFβI gene is determined using at least two oligonucleotide primer pairs and the gDNA solution. These at least two nucleotides are located at respective independent positions of the TGFβI gene corresponding to respective independent single nucleotide polymorphisms (SNPs) associated with corneal dystrophy.

12 Claims, 13 Drawing Sheets
Specification includes a Sequence Listing.

(56) References Cited

FOREIGN PATENT DOCUMENTS

| WO | WO 2007/002567 A2 | 1/2007 | |
|---|---|---|---|
| WO | WO 2007/083928 A1 | 7/2007 | |
| WO | WO 2008/089280 A2 | 7/2008 | |
| WO | WO-2012044121 A2 * | 4/2012 | ........... C12Q 1/6883 |
| WO | WO 2012044121 A2 | 4/2012 | |
| WO | WO 2015/073978 A2 | 5/2015 | |
| WO | WO2015/089462 A1 | 6/2015 | |

OTHER PUBLICATIONS

Avellino Co. Ltd., Examination Report, IN 7514/CHENP/2011, dated Oct. 15, 2014, 2 pgs.
Avellino Co. Ltd., First Examination Report, IN 7514/CHENP/2011, dated Aug. 7, 2014, 1 pg.
Avellino Co. Ltd., Letters Patent, CN 200980159748.3, dated Apr. 8, 2015, 2 pgs.
Avellino Co. Ltd., Notice of Reasons for Rejection, JP 2012-505796, dated Nov. 11, 2014, 3 pgs.
Avellino Co. Ltd., Notice of Reasons for Rejection, JP 2012-505796, dated Oct. 29, 2013, 3 pgs.
Avellino Co. Ltd., Notice of Reasons for Rejection, JP 2013-531500, dated Oct. 21, 2014, 5 pgs.
Avellino Co. Ltd., Notice of Reasons for Rejection, JP 2014-000571, dated Mar. 10, 2015, 4 pgs.
Avellino Co. Ltd., Notice of Reasons for Rejection, JP 2014-000571, dated Oct. 6, 2015, 7 pgs.
Avellino Co. Ltd., Certificate of Patent, JP 2014-000571, dated Apr. 1, 2016, 5 pgs.
Avellino Co., Ltd. Decision of Rejection, JP2013-531500, dated Aug. 21, 2015, 11 pgs.
Avellino Co., Certificate of Patent, JP2013-531500, dated Jan. 13, 2017, 3 pgs.
Avellino Co. Ltd., Notification of the Office Rejection, CN 200980159748.3, dated Aug. 6, 2014, 4 pgs.
Avellino Co. Ltd., Notification of Grant, CN201180056997.7, dated Jul. 16, 2015, 5 pgs.
Avellino Co. Ltd., The First Office Action, CN 200980159748.3, dated Aug. 31, 2012, 4 pgs.
Avellino Co. Ltd., The First Office Action, CN 201180056997.7, dated Dec. 22, 2014, 4 pgs.
Avellino Co. Ltd., The Second Office Action, CN 200980159748.3, dated Jul. 11, 2013, 5 pgs.
Avellino Co. Ltd., The Third Office Action, CN 200980159748.3, dated Mar. 24, 2014, 5 pgs.
Avellino Co. Ltd., Office Action, CN201510121642.1, dated Aug. 12, 2016, 8 pgs.
Avellino Co. Ltd., 2nd Office Action, CN201510121642.1, dated Jun. 28, 2017, 7 pgs.
Avellino Co. Ltd., Patent Examination Report No. 1, AU2009344501, dated Sep. 24, 2012, 3 pgs.
Avellino Co. Ltd., Patent Examination Rpt-No. 3-AU2009344501, dated Nov. 25, 2013, 4 pgs.
Avellino Co. Ltd., Decision to Grant, EP09843403.8, dated Feb. 10, 2014, 1 pg.
Avellino Co. Ltd., Patent Certificate, EP09843403-8, dated Oct. 29, 2014, 1 pg.
Avellino Co. Ltd., Office Action, IDW-00201103762, dated Jul. 6, 2017, 3 pgs.
Avellino Co. Ltd., Invitation to Respond to Written Opinion, SG201107572.8, dated Jan. 29, 2014, 12 pgs.
Avellino Co. Ltd., Certificate of Patent, ZA2011/07967, dated Aug. 28, 2013, 1 pg.
Avellino Co. Ltd.,Decision of Grant, RU2011146553, dated Jul. 23, 2014, 2 pgs.
Avellino Co. Ltd., Letters Patent, RU2011146553, dated Dec. 17, 2014, 1 pg.
Avellino Co. Ltd., The First Office Action, CN201080047181.3, dated Jul. 15, 2013, 1 pg.
Avellino Co. Ltd., Certificate of Patent, JP2012525483, dated Jan. 10, 2014, 5 pgs.
Avellino Co. Ltd., First office Action, IL215845, dated Jul. 10, 2013, 4 pgs.
Avellino Co. Ltd., Further Office Action, IL215845, dated Mar. 25, 2014, 4 pgs.
Avellino Lab, Extended European Search Report, EP14762603.0, dated Jul. 14, 2016, 11 pgs.
Avellino Lab, Communication Pursuant to Rules 161(2) and 162, EP14862501, dated Jul. 21, 2016, 2 pgs.
Avellino Lab, Communication Pursuant to Rules 70(2) and 70a(2), EP14762603.0, dated Aug. 2, 2016, 12 pgs.
Avellino Lab, Formality Office Action JP2016531678, dated Mar. 29, 2017, 3 pgs.
Avellino Lab USA Inc., International Search Report and Written Opinion, PCT/US2014/029466, dated Jul. 14, 2014, 11 pgs.
Avellino Lab USA Inc., International Preliminary Report on Patentability, PCT/US2014/029466, daetd Sep. 15, 2015, 11 pgs.
Avellino Lab USA Inc., International Search Report and Written-Opinion, PCT/US2014/065975, dated May 18, 2015, 19 pgs.
Avellino Lab USA Inc., International Preliminary Report on Patentability, PCT/US2014/065975, dated May 17, 2016, 12 pgs.
Beer et al., On-Chip, Real-Time, Single-Copy Polymerase Chain Reaction in Picoliter Droplets, 2007, Analytical Chemistry 79 (22): 8471, 5 pgs.
Biotechnology Journal, 2006, vol. 6, No. 5, pp. 621-624.
Korea Advanced Institute of Science and Technology et al., Invitation Pursuant to Rule 62a(1) EPC, EP10810154.4, dated Sep. 11, 2015, 2 pgs.
Korea Advanced Institute of Science and Technology et al., Extended European Search Report, EP10810154.4, dated Jan. 18, 2016, 9 pgs.
Korea Advanced Institute of Science and Technology et al., Communication Pursuant Article 94(3), EP10810154.4, dated Nov. 6, 2017, 5 pgs.
Chakravarthi, TGFBI Gene Mutations Causing Lattice and Granular Corneal Dystrophies in Indian Patients, Investigative Ophthalmology & Visual Science, Jan. 2005, vol. 46, No. 1, 5 pgs.
Cao W. et al., "Comparison of Methods for DNA Extraction from Paraffin-Embedded Tissues and Buccal Cells," Cancer Detection and Prevention, Elsevier Science, NL, vol. 27, No. 5, Jan. 1, 2003, 8 pgs.
Chao-Shern, Office Action, U.S. Appl. No. 14/788,572, dated Dec. 16, 2016, 14 pgs.
Database Genbank, Dec. 10, 1997, Database accession No. AF035627, 2 pgs.
Dolmetsch, A., et al., "Combined granular-lattice corneal dystrophy (Avellino) in a patient with no known Italian ancestry", Can. J. Ophthalmol, Accepted for publication Sep. 15, 1995, pp. 29-31, vol. 31, No. 1.
Endo T et al., "Label-Free Detectionof Peptide Nucleic Acid-DNA Hybridization Using Localized Surface Plasmon Resonance Based Optical Biosensor," Analytical Chemisty, American Chemical Society, US, vol. 77, No. 21, 9 pgs.
GenBank Accession No. AF035627, "*Homo sapiens* mutant kerato epithelin (BIGH3) Gene, exon 4, partial cds," [retrieved on-line: http://www.ncbi.nlm.nih.gov/nuccore/AF035627.1, retrieval date, Sep. 7, 2013], published date Dec. 1997, Skonier et al., 1 pg.
Grove, D.S., "Quantitative Real-Time Polymerase Chain Reaction for the Core Facility Using TaqMan and the Perkin-Elmer/Applied Biosystems Division 7700 Sequence Detector," Journal of Biomolecular Techniques, Mar. 1999, vol. 10, pp. 11-16.
Halfon, P., et al., "Detection of IL28B SNP DNA from Buccal Epithelial Cells, Small Amounts of Serum and Dried Blood Spots," Mar. 2012, Plos ONE, vol. 7, Issue 3, Article No. e33000, pp. 1-6.
Han, "Clinical Findings and Treatments of Granular Corneal Dystrophy Type 2 (Avellino Corneal Dystrophy): A Review of the Literature," Eye & Contact Lens, vol. 36, No. 5, Sep. 2010, 4 pgs.
Holland, E., et al., "Avellino corneal dystrophy. Clinical manifestations and natural history", Ophthalmology, Originally received Jan. 2, 1992, pp. 1564-1568, vol. 99, No. 10.
Huerva et al., "Role of BIGH3 R124H mutation in the diagnosis of Avellino corneal dystrophy," European Journal of Ophthalmology, May 2008, vol. 18, No. 3, pp. 345-350, 6 pgs.

(56) References Cited

OTHER PUBLICATIONS

Jun, R., et al., "Avellino Corneal Dystrophy After Lasik", Ophthalmology, © 2004 (Originally received Mar. 21, 2003), pp. 463-468, vol. 111.
Kennedy, S., et al., "Combined granular lattice dystrophy (Avellino corneal dystrophy)", Br. J. Ophthalmol, Accepted for publication Jan. 19, er1996, pp. 489-490, vol. 80.
Kephart, D., "Rapid Isolation of Genomic DNA from Small Quantities of Human Tissue," 1999, Profiles in DNA, vol. 2, No. 3, pp. 7-9.
Kim, Jeong Wan et al., 'Anesthetic experience for patients with malignant gyperthermia susceptibility determined by molecular genetic test', J Korean Ophthalmol Soc vol. 49, No. 9, 2008, pp. 1431-1436.
Lee, Final Office Action, U.S. Appl. No. 13/264,784, dated May 7, 2014, 26 pgs.
Lee, Final Office Action, U.S. Appl. No. 13/391,167, dated May 18, 2015, 16 pgs.
Lee, Notice of Allowance, U.S. Appl. No. 13/391,167, dated Jul. 27, 2015, 9 pgs.
Lee, Office Action, U.S. Appl. No. 13/264,784, dated Sep. 12, 2013, 14 pgs.
Lee, Office Action, U.S. Appl. No. 13/391,167, dated Dec. 29, 2014, 9 pgs.
Lee, Office Action, U.S. Appl. No. 13/876,603, dated Apr. 13, 2015, 11 pgs.
Lee, Final Office Action, U.S. Appl. No. 13/876,603, dated Nov. 6, 2015, 14 pgs.
Lee, Office Action, U.S. Appl. No. 13/876,603, dated Nov. 30, 2016, 12 pgs.
Lee, Notice of Allowance, U.S. Appl. No. 13/876,603, dated Nov. 22, 2017, 9 pgs.
Lee, Office Action, U.S. Appl. No. 14/454,669, dated May 4, 2016, 12 pgs.
Lee, Final Office Action, U.S. Appl. No. 14/454,669, dated Feb. 22, 2017, 14 pgs.
Lee, Notice of Allowance, U.S. Appl. No. 14/454,669, dated Dec. 1, 2017, 8 pgs.
Lee, Office Action, U.S. Appl. No. 14/472,325, dated Dec. 19, 2016, 18 pgs.
Lounsbury Jenny et al., "Enhanced Recovery of Spermatozoa and Comprehensive Lysis of Epithelial Cells from Sexual Assault Samples Having a Low Cell Counts for Aged Up to One Year," Forensic Science International: Genetics, vol. 8, No. 1, Jan. 2014, 6 pgs.
Miller, S., et al., "A Simple Salting Out Procedure for Extracting DNA from Human Nucleated Cells," Nucleic Acids Research, 1998, pp. 1215, vol. 16, No. 3, , Accepted for publication Jan. 19, 1996, 2 pgs.
Morbini Patrizia et al., "Oral HPV Infection and Persistence in Patients with Head and Neck Cancer," Oral Surgery, Oral Medicine, Oral Pathology and Oral Radiology, vol. 116, No. 4, Oct. 2013, 11 pgs.
Neuhaus, T., et al., "Reliability of Non-Invasively Acquired Human Genomic DNA as a Substrate for Real-Time PCR-Assisted Analysis of Genetic Polymorphisms," Archives of Toxicology, vol. 78, No. 7, Jul. 1, 2004, 7 pgs.
NCBI, "*Homo sapiens* Transforming Growth Factor, Beta-Induced, 68kDa (TGFBI), Mrna," NCBI Reference Sequence NM_000358.2, release 107, Mar. 13, 2015, 6 pgs.
Paliwal et al., Heterozygous Change T>G in the Sequence of Exon 12 of TGFBI Gene Seen in a Patienet with Corneal Dystrophy, Genbank :GQ368823.1, National Center for Biotechnology Information, Genbank, Jul. 28, 2009. 6 pgs.
Richards, et al., Multiplex PCR Amplification from the CFTR Gene Using DNA Prepared from Buccal Brushes/Swabs, 1993, Human Molecular Genetics 2 (2): 159-163, 5 pgs.
Romero, P. et al., 'Anticipation in familial lattice corneal dystrophy type I with R124C mutation in the TGFBI {BIGH3} gene', Molecular Vision vol. 14, May 7, 2008, pp. 829-835.

Stewart, H., et al., "Hetero TGFBI (BIGH3) gene-lessons for corneal amyloidogenesis", Hum. Mutat, Accepted revised manuscript Apr. 23, 1999, pp. 126-132, vol. 14.
Strum, J.C. et al., 'Tissue expression profiling using real-time PCR', Curr Protoc Pharmacol Nov. 2002;Chapter 6:Unit 6.9. DOI: 10.1002/0471141755.PH0609S18.
Walker et al., Collection of Genomic DNA by Buccal Swabs for Polymerase Chain Reaction-Based Biomaker Assays, 1999, Environmental Health Perspectives 107 (7): 517, 4 pgs.
Wittwer, Carl T. , et al., "Real-Time Multiplex PCR Assays," 2001, Department of Pathology, University of Utah, School of Medicine, Salt Lake City, Utah 84132, 13 pgs.
Yoo, So Young et al., 'Development of a DNA chip for the diagnosis of the most common corneal dystrophies caused by mutations in the high 3 gene', Br J Ophthalmol vol. 91, Jan. 10, 2007, pp. 722-727.
Yoshida, S., et al., "An analysis of BIGH3 mutations in patients with corneal dystrophies in the Kyushu district of Japan," Jpn J Ophthalmol. Jul.-Aug. 2002;46(4):469-71, 3 pgs.
Zheng, Y. B., et al., "Surface plasmons of metal nanostructure arrays: from nanoengineering to active plasmonics," Jul. 9, 2008, Journal of the Association for Laboratory Automation, vol. 13, No. 4, pp. 215-226.
Avellino Lab, Communication Pursuant to Rules 70(2) and 70a(2), EP14862501.5, dated Aug. 8, 2017, 1 pg.
Avellino Lab, Extended European Search Report, EP14862501.5, dated Jul. 21, 2017, 24 pgs.
Avellino Lab, Communication Pursuant to Article 94(3), EP14862501.5, dated Jul. 16, 2018, 6 pgs.
Avellino Lab USA Inc., International Search Report and Written Opinion, PCT/US2016/061893, dated Feb. 21, 2017, 10 pgs.
Avellino Lab USA Inc., International Preliminary Report on Patentability, PCT/US2016/061893, dated May 15, 2018, 6 pgs.
Chao-Shern, Notice of Allowance, U.S. Appl. No. 14/788,572, dated Aug. 28, 2017, 7 pgs.
Lee, Final Office Action, U.S. Appl. No. 15/947,473, dated Sep. 20, 2021, 9 pgs.
Lee, Non-Final Office Action, U.S. Appl. No. 15/947,473, dated May 7, 2021, 12 pgs.
Lee, Final Office Action, U.S. Appl. No. 15/947,473, dated Oct. 1, 2020, 14 pgs.
Lee, Non-Final Office Action, U.S. Appl. No. 15/947,473, dated Feb. 24, 2020, 12 pgs.
Lee, Non-Final Office Action, U.S. Appl. No. 15/947,463, dated May 5, 2021, 13 pgs.
Lee, Final Office Action, U.S. Appl. No. 15/947,463, dated Dec. 15, 2021, 13 pgs.
Lee, Notice of Allowance, U.S. Appl. No. 15/947,463, dated Apr. 8, 2022, 10 pgs.
Lee, Notice of Allowance, U.S. Appl. No. 15/947,473, dated Oct. 27, 2021, 6 pgs.
Avellino Co. Ltd., Communication Pursuant to Rules 161(2) and 162, EP 16865232.9, dated Jun. 20, 2018, 3 pgs.
Bass et al., " Detection of Knockdown Resistance (kdr) Mutations in Anopheles Gambiae: A Comparison of Two New High-Throughput Assays with Existing Methods," Malaria Journal, Aug. 2007, vol. 6, 14 pgs.
Byrne et al., Genome Editing in Human Stem Cells, Methods in Enzymology, 2014, vol. 546, pp. 1-16.
Courtney, et al., "A Review of Personalised Molecular Medicine for the Treatment of Cornel Disorders," International Journal of Ophthalmology and Eye Disease, Aug. 27, 2015, vol. S, No. 2, pp. 7-18.
Courtney, et al., CRISPR/Cas9 DNA Cleavage at SNP-Derived PAM Enables Both in vitro and in vivo KRT12 Mutation-Specific Targeting, Gene Therapy, Aug. 20, 2015, vol. 23, No. 1, pp. 108-112.
Dias et al., "Development of a real-time PCR assay for detection of *Mytiius* species alleles: Application to a sampling survey in Scotland," Journal of Experimental Marine Biology and Ecology, Amsterdam, NL, vol. 367, No. 2, Dec. 15, 2008, 6 pgs.
Fujiki et al., "Six different mutations of TGFBI (betaig-h3, keratoepithelin) gene found in Japanese corneal dystrophies," Cornea: The Journal of Cornea and External DIS, Lippincott Williams & Wilkins, US, vol. 19, No. 6, Nov. 1, 2000, 4 pgs.

(56) References Cited

OTHER PUBLICATIONS

Li et al., "Multicolor Real-Time PCR Genotyping of ABO System Using Displacing Probes," Journal of Forensic Sciences, vol. 55, No. 1, Dec. 2, 2009, 6 pgs.

Munier et al., "BIGH3 mutation spectrum in corneal dystrophies," Investigative Ophthalmology & Visual Science—IOVS, Association for Research in Vision and Ophthalmology, US., vol. 43, No. 4, Apr. 1, 2002, 6 pages.

Ouyang et al., Ocular Stem Cell Research from Basic Science to Clinical Application, A Repot from Zhongshan Ophthalmic Center Ocular Stem Cell Symposium, International Journal of Molecular Sciences, Mar. 22, 2016, pp. 1-15.

Yoshida, S., et al., "Rapid genotyping for most common TGFI mutations with real-time polymerase chain reaction," Human Genetics, Springer, Berlin, DE, vol. 116, No. 6, May 1, 2005, 7 pgs.

Zhang, et al., Isolation and Transplantation of Corneal Endothelial Cell-Like Cells Derived from. In-Vitro-Differentiated Human Embryonic Stem Cells, Stem Cells and Development, Feb. 5, 2014, vol. 23, No. 12, pp. 1340-1354.

Avellino Co. Ltd., Office Action, BR-PI0924016-0, dated Sep. 12, 2018, 3 pgs (No English Translation Available).

Avellino Lab, Decision to Grant, EP 14762603.0, dated Nov. 2, 2018, 2 pgs.

Avellino Lab, Notice of Reasons for Rejection, JP 2016-531678, dated Oct. 16, 2018, 4 pgs.

Avellino Co. Ltd., First Office Action, CN201480072417.7, dated Feb. 27, 2019, 7 pgs.

* cited by examiner

ACD Fw primer:
(SEQ ID NO: 1)
5'-TCC ACC ACC ACT CAG CTG TA

ACD Re primer:
(SEQ ID NO: 2)
5'-CCA TCT CAG GCC TCA GCT T
(60 bp)

AV Fw primer:
(SEQ ID NO: 3)
5'-TGC AGC CCT ACC ACT CTC AA

AV Re primer:
(SEQ ID NO: 4)
5'-AGG CCT CGT TGC TAG G
(150 bp)

Real Fw primer:
(SEQ ID NO: 5)
5'-TAG TCT CTT ATT CTA ATA GA

Real Re primer:
(SEQ ID NO: 6)
5'-GCT GCA GAC TCT GTG TTT AA
(860 bp)

ACD Fw2 primer:
(SEQ ID NO: 7)
5'-CCA TCC CTC CTT CTG TCT TCT G

ACD Re2 primer:
(SEQ ID NO: 8)
5'-CGG GCC CCT CCA TCT C
(140 bp)

ACD Fw3 primer:
(SEQ ID NO: 9)
5'-CAG AGA AGG GAG GGT GTG GTT

ACD Re3 primer:
(SEQ ID NO: 10)
5'-GGG CGA AGA TGG TGA AGC T
(190 bp)

ACD Fw4 primer:
(SEQ ID NO: 11)
5'-TCC TCG TCC TCT CCA CCT GTA

ACD Re4 primer:
(SEQ ID NO: 12)
5'-AGC TGG CAA GGA GGC CC

ACD Fw5 primer:
(SEQ ID NO: 13)
5'-TTT GGG CTT TCC CAC ATG C

ACD Re5 primer:
(SEQ ID NO: 14)
5'-GGC AGA CGG AGG TCA TCT CA

ACD Fw6 primer:
(SEQ ID NO: 15)
5'-GTA GTA CCG TGC TCT CTG

ACD Re6 primer:
SEQ ID NO: 16)
5'-AGT TCC CCA TAA GAA TCC CCC

ACD Fw7 primer:
(SEQ ID NO: 17)
5'-GGC TGG ACC CCC AGA GG

ACD Re7 primer:
(SEQ ID NO: 18)
5'-ACC CCT CGG GGA AGT AAG G

ACD Fw8 primer:
(SEQ ID NO: 19)
5'-AAC CTT TAC GAG ACC CTG GGA

ACD Re8 primer:
(SEQ ID NO: 20)
5'-GAC TCC CAT CCA TCA TGC CC

ACD Fw9 primer:
(SEQ ID NO: 21)
5'-AGT CGT TGG ATC CAC CAC CA

ACD Re9 primer:
(SEQ ID NO: 22)
5'-GAC GTC ATT TCC TAC TGT TTC AGG

ACD Fw10 primer:
(SEQ ID NO: 23)
5'-CCC CCC AGA AAC AGC CTG

ACD Re10 primer:
(SEQ ID NO: 24)
5'-TTC TAA GGG GTT AAG GAG AAA GCT T

Figure 2

Normal probe 1:
(SEQ ID NO: 25)
VIC-CAC GGA CCG CAC GGA-NFQ
(15 bp)

Mutant probe 1:
(SEQ ID NO: 26)
FAM-CAC GGA CCA CAC GGA-NFQ

Normal probe 2:
(SEQ ID NO: 27)
VIC-ACA CGG ACC GCA CG-NFQ

Mutant probe 2:
(SEQ ID NO: 28)
FAM-ACA CGG ACC ACA CG-NFQ
(14 bp)

Normal probe 3:
(SEQ ID NO: 29)
VIC-TAC ACG GAC CGC A-NFQ

Mutant probe 3:
(SEQ ID NO: 30)
FAM-TAC ACG GAC CAC A-NFQ
(13 bp)

Normal probe 4:
(SEQ ID NO: 31)
VIC-CTG TAC ACG GAC CGC ACG-NFQ

Mutant probe 4:
(SEQ ID NO: 32)
FAM-CTG TAC ACG GAC CAC ACG-NFQ
(18 bp)

Normal probe 5:
(SEQ ID NO: 33)
VIC-CTG TAC ACG GAC CGC ACG GAG-NFQ

Mutant probe 5:
(SEQ ID NO: 34)
FAM-CTG TAC ACG GAC CAC ACG GAG-NFQ
(21 bp)

Normal probe 6:
(SEQ ID NO: 35)
VIC-GCT GTA CAC GGA CCG CAC GGA GAA-NFQ

Mutant probe 6:
(SEQ ID NO: 36)
FAM-GCT GTA CAC GGA CCA CAC GGA GAA-NFQ

Normal probe 7:
(SEQ ID NO: 37)
VIC-ACC GCA CGG AGA AGC-NFQ

Mutant probe 7:
(SEQ ID NO: 38)
FAM-ACC ACA CGG AGA AGC-NFQ

Normal probe 8:
(SEQ ID NO: 39)
VIC-ACC GCA CGG AGA AGC TGA GGC-NFQ

Mutant probe 8:
(SEQ ID NO: 40)
FAM-ACC ACA CGG AGA AGC TGA GGC-NFQ

Normal probe 8:
(SEQ ID NO: 41)
VIC-ACC GCA CGG AGA AGC TGA GGC CTG-NFQ

Mutant probe 8:
(SEQ ID NO: 42)
FAM-ACC ACA CGG AGA AGC TGA GGC CTG-NFQ

Figure 3

TaqMan MGB PROBE

| | | |
|---|---|---|
| #TGFBI R124NI | VIC-CAC GGA CCG CAC GGA- MGB NFQ | SEQ ID NO: 53 |
| #TGFBI R124H | FAM-CAC GGA CCA CAC GGA- MGB NFQ | SEQ ID NO: 54 |
| #TGFBI R124C | FAM-CAC GGA CTG CAC GGA- MGB NFQ | SEQ ID NO: 48 |
| #TGFBI R124L | FAM-CAC GGA CCT CAC GGA- MGB NFQ | SEQ ID NO: 49 |
| #TGFBI R555NI | VIC-CAC CAA GAG AAC GGA-MGB NFQ | SEQ ID NO: 55 |
| #TGFBI R555W | FAM-CAC CAA GAG AAT GG-MGB NFQ | SEQ ID NO: 56 |
| #TGFBI R555Q-1 | FAM-AC CAA GAG AAC AGA G-MGB NFQ | SEQ ID NO: 50 |

SEQUENCE DETECTION PRIMER

| | | |
|---|---|---|
| #TGFBI 124 F | TCC ACC ACT CAG CTG TA | SEQ ID NO: 57 |
| #TGFBI 124 R | CCA TCT CAG GCC TCA GCT T | SEQ ID NO: 58 |
| #TGFBI 555 F | ACA CAG TCT TTG CTC CCA CAA A | SEQ ID NO: 59 |
| #TGFBI 555 R | ACT TAA GTT GGT CTT TAC CCA AGA GTC T | SEQ ID NO: 60 |

Figure 4

DATA A >> LifeTech/7500FAST; fast mode

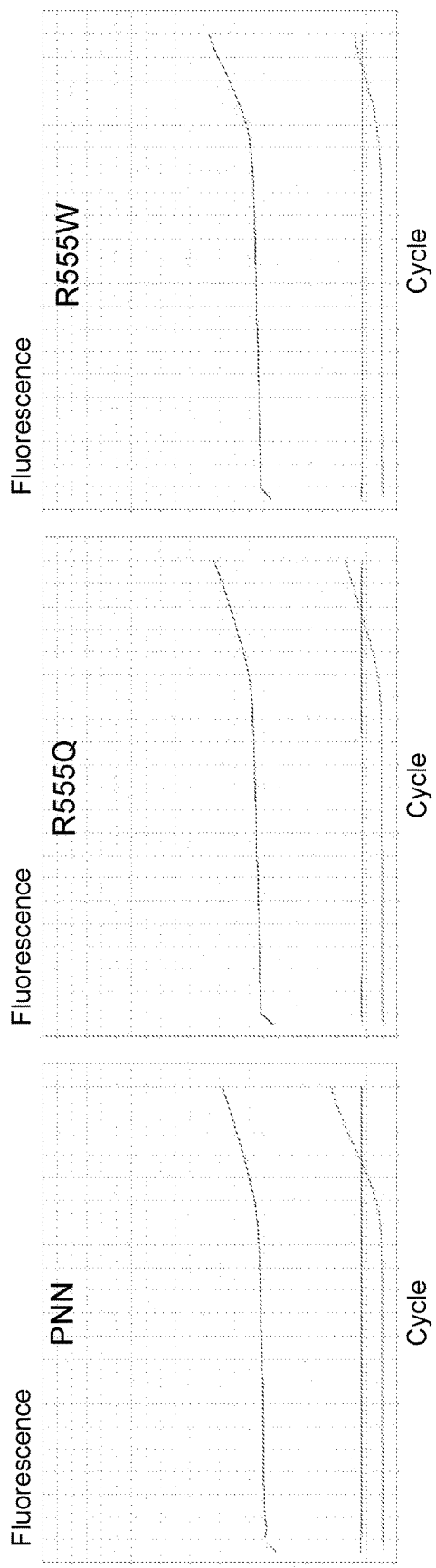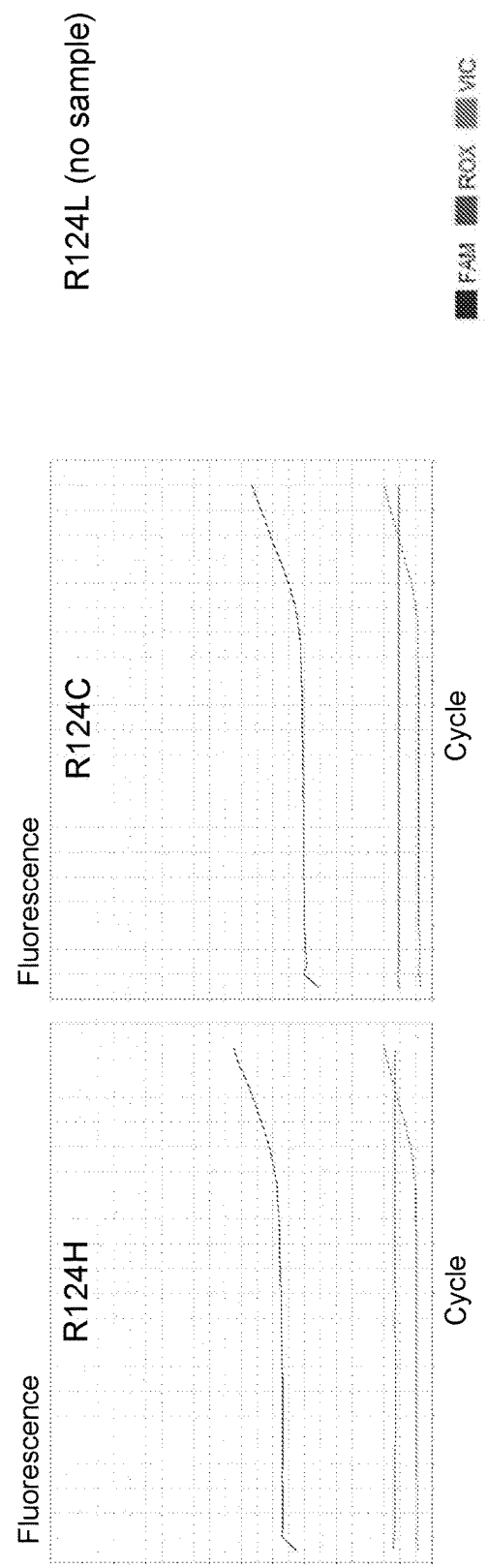
Figure 5B

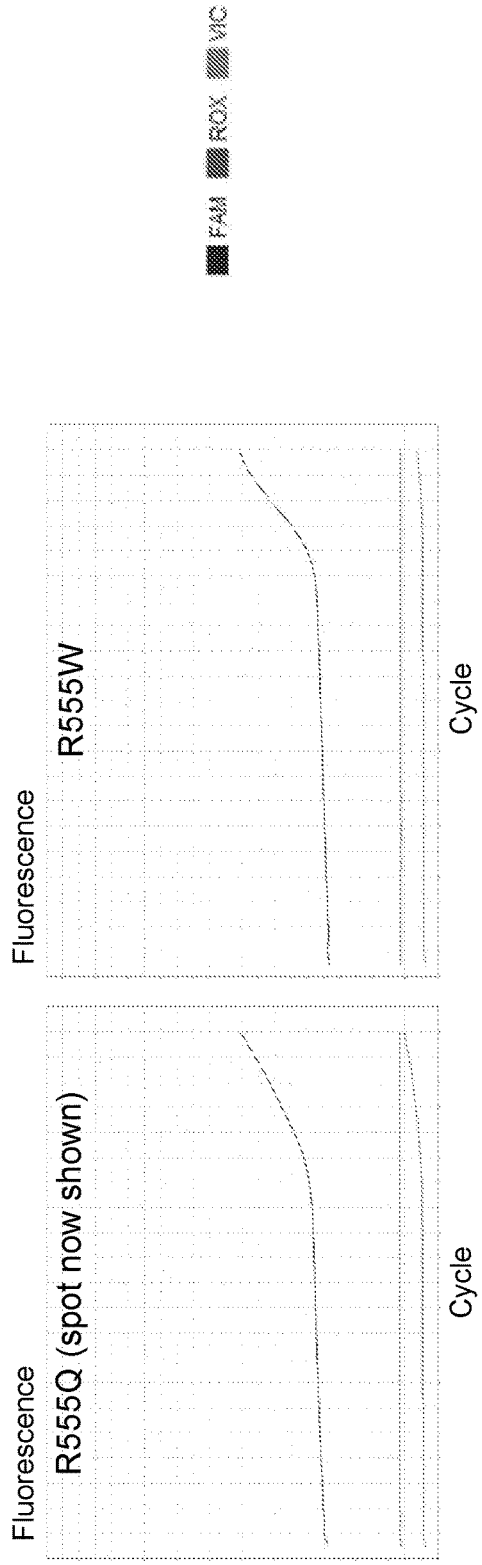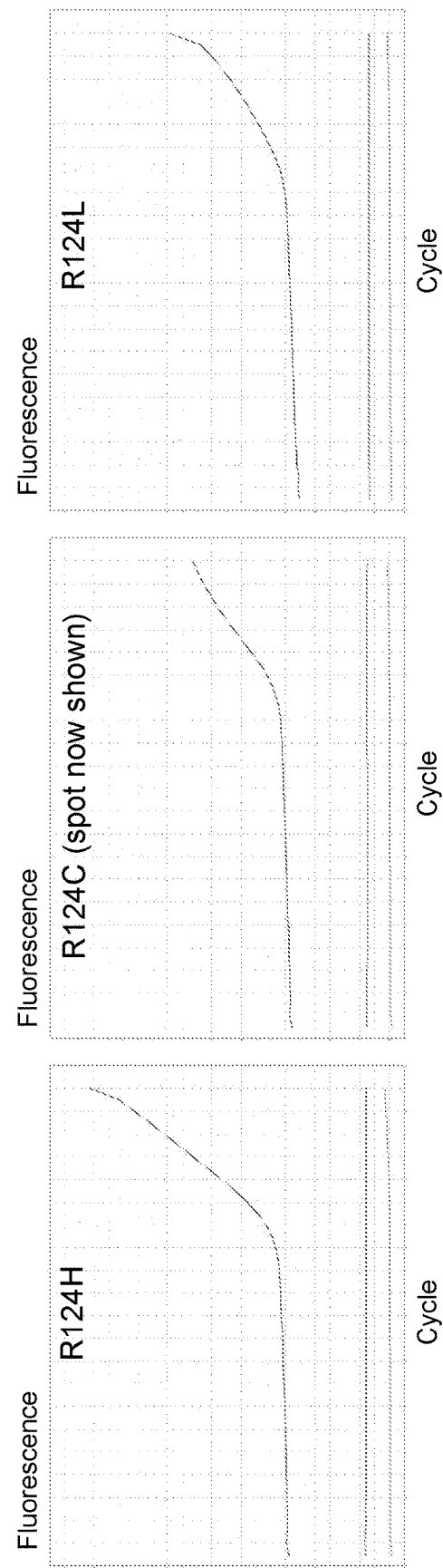
Figure 5C

DATA B >> LifeTech/7500FAST; fast mode

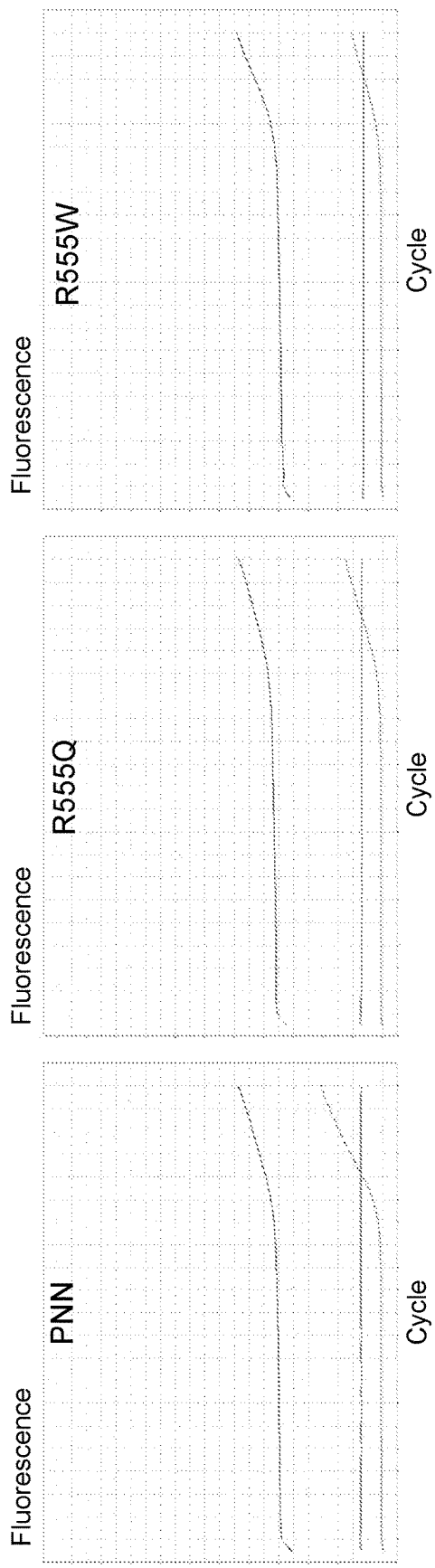
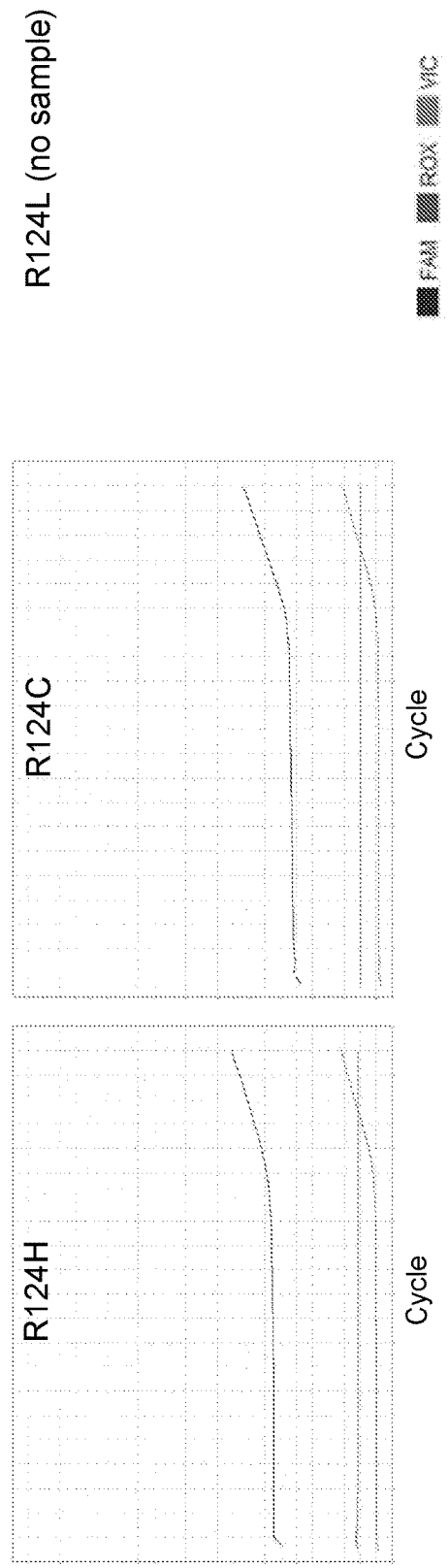
Figure 6B

ABSTRACT

METHODS FOR MULTIPLEX DETECTION OF ALLELES ASSOCIATED WITH OPHTHALMIC CONDITIONS

RELATED APPLICATION

This application is a continuation application of International Application No. PCT/US2014/065975, filed Nov. 17, 2014, which claims priority to U.S. Provisional Patent Application Ser. No. 61/905,051, filed Nov. 15, 2013. All of these patent applications are incorporated by reference herein in their entireties.

FIELD OF THE APPLICATION

This application generally relates to methods for the isolation and detection of disease-associated genetic alleles. In particular, this application relates to an improved method for the detection of an Avellino corneal dystrophy associated allele.

BACKGROUND

Real-time PCR can be used to detect differences between nucleic acid sequences having substantially identical sequences. Through the use of differentially labeled fluorescent nucleic acid probes, for example one that binds to a wild type sequence and one that binds to a mutant sequence, single nucleotide changes in the human genome can be quickly and reliably detected. This resolving power has been applied to medical diagnostics, where single nucleotide polymorphisms (SNPs), i.e., single base changes found within the coding and/or non-coding sequence of a protein, are correlated to human disease.

However, real-time PCR analysis is highly dependent upon the collection and isolation of high quality samples. Poor sample collection and/or isolation require the use of longer assay conditions and greater amounts of real-time PCR reagents, both of which result in increased costs and reduced productivity. Furthermore, failure of a real-time PCR single nucleotide polymorphism detection assay can result in the need to collect additional samples, causing even greater loss in time and resources.

Accordingly, methods resulting in improved sample collection and isolation, which improve the overall success rate of the assay, reduce the reagents required for the assay, and reduce the need to collect additional samples at later time are highly desirable. Furthermore, methods for performing real-time PCR SNP detection assays with lower amounts of sample material will also reduce the challenges associated with the collection and isolation of high quality samples.

Corneal dystrophy can be an autosomal dominant hereditary disease, which initially presents with blurred vision in the center of a patient's cornea. The blurry vision gradually spreads toward the perimeter of cornea, worsening the patient's vision as they age. There are several types of corneal dystrophy that have been characterized, including Avellino corneal dystrophy, Granular corneal dystrophy, lattice type I corneal dystrophy, Thiel-Behnke, and Reis-bucklers corneal dystrophy. Corneal dystrophies are known to be caused, at least in some cases, by mutations in the transforming growth factor beta induced (TGFβI) gene encoding the βIG-H3 protein (also known as TGFβI protein, TGFBI protein, and keratoepithelin).

Heterozygous patients suffering from Avellino corneal dystrophy have increasing loss in vision with age, becoming severe in the later years of life. Homozygous patients, in contrast, present with severe to complete loss of vision by six years of age. Avellino corneal dystrophy was first recognized as a distinct type of corneal dystrophy around 1988. Prior to then, it was likely misclassified as Granular corneal dystrophy. Today, Avellino corneal dystrophy is known to be the most common form of stromal corneal dystrophy worldwide. In Korea, Avellino corneal dystrophy is believed to have a prevalence around 1 in 870 people (see Lee, J. H. et al., *Ophthalmic Epidemiol.*, 17:160, 2010; see also Holland, E. J. et al., *Ophthalmology*, 99:1564, 1992; Kennedy, S. M. et al., *Br. J. Ophthalmol.*, 80:489, 1996; Dolmetsch, A. M. et al., *Can. J. Ophthalmol.*, 31:29, 1996; Afshari, N. A. et al., *Arch. Ophthalmol.*, 119:16, 2001; Stewart, H. S. *Hum. Mutt.*, 14:126, 1999).

Previously, it was discovered that heterozygous individuals (e.g., having one wild type βIG-H3 allele and one mutant βIG-H3 allele) were highly susceptible to accelerating loss of vision following LASIK surgery. Notably, two years after surgery increased opacity of the cornea was observed in these patients with increasing aggressiveness, eventually resulting in complete loss of vision (Jun, R. M. et al., *Opthalmology*, 111:463, 2004). Previously, eye surgery has been performed with an expectation that LASIK or Excimer Laser surgery would get rid of vision blurriness of a patient suffering from corneal dystrophy. For a hypothetical number of three hundred thousand cases of LASIK surgery, 300 people would have lost their vision, based on $1/1000$ of minimum estimation of heterozygous patients suffering from Avellino corneal dystrophy. Patients who have undergone LASIK surgery are mainly in their 20's and 30's carrying out productive activities; therefore, their vision loss causes serious troubles in both society and economics.

In addition, after approval of LASIK surgery in year 2000 in USA, African American patients suffering from Avellino corneal dystrophy who underwent LASIK surgery have been found to lose eye sight, which infers that plenty of similar cases might be occurring throughout the world.

Therefore, although accurate diagnosis of Avellino corneal dystrophy is required to prevent the progression of Avellino corneal dystrophy by LASIK surgery, the diagnosis of Avellino corneal dystrophy is just conducted by microscopic observation (e.g., slit-lamp examination) of corneal opacity and thus often doctors miss latent symptoms of patients to perform LASIK surgery, which results in vision loss. Therefore, rapid and precise genetic diagnosis of corneal dystrophy is desirable.

A DNA chip for detecting a mutation in βIG-H3 gene, which is responsible for Avellino corneal dystrophy, was developed (Korean Patent Laid-Open Publication No. 10-2007-0076532). However, the diagnosis of Avellino corneal dystrophy using the DNA chip disadvantageously requires several steps, including a step of amplifying DNA in a sample, a step of hybridizing the amplified DNA with the DNA chip, a step of washing the hybridized DNA chip, and a step of detecting a positive response.

Given the above background, what is needed in the art are improved methods for detecting multiple mutated alleles associated with corneal dystrophy.

SUMMARY

The present disclosure provides improved methods for the detection of one or more alleles associated with human disease. The methods described below decrease the time and cost associated with performing assays that yield medical information about a subject. For example, in some embodiments, the improved methods allow for same-day detection of a genomic marker associated with Avellino corneal dystrophy, at a reduced cost to the patient.

In some embodiments, the present disclosure provides methods for detecting at least two genomic alleles associated with corneal dystrophy in a sample from a subject, the method comprising: (A) providing epithelial cells of a subject adhered to a tip of a substrate; (B) agitating the tip of the substrate in a lysis solution that lyses cells adhered to the substrate; (C) removing the substrate from the lysis solution upon completion of the agitating (B); (D) incubating the lysis solution after the removing (C); (E) isolating genomic DNA from the lysis solution to form a gDNA solution; and (F) determining an identity of at least two nucleotides present in the TGFβI gene using at least two oligonucleotide primer pairs and the gDNA solution, wherein the at least two nucleotides are located at respective independent positions of the TGFβI gene corresponding to respective independent single nucleotide polymorphisms (SNPs) associated with corneal dystrophy.

In some embodiments, the at least two nucleotides present in the TGFβI gene are separated in the human genome by at least one nucleotide.

In some embodiments, at least one pair of the at least two oligonucleotide primer pairs comprises a forward PCR primer having a nucleotide sequence comprising SEQ ID NO:1 and a reverse PCR primer having a nucleotide sequence comprising SEQ ID NO:2.

In some embodiments, at least one pair of the at least two oligonucleotide primer pairs comprises a forward PCR primer having a nucleotide sequence comprising SEQ ID NO:43 and a reverse PCR primer having a nucleotide sequence comprising SEQ ID NO:44.

In some embodiments, the at least two oligonucleotide primer pairs comprise a first amplification primer pair and a second amplification primer pair. The first amplification primer pair comprises a forward PCR primer having a nucleotide sequence comprising SEQ ID NO:1 and a reverse PCR primer having a nucleotide sequence comprising SEQ ID NO:2. The second amplification primer pair comprises a forward PCR primer having a nucleotide sequence comprising SEQ ID NO:43 and a reverse PCR primer having a nucleotide sequence comprising SEQ ID NO:44.

In some embodiments, the determining (F) further comprises using: (i) a first wild type detection probe having a nucleotide sequence comprising SEQ ID NO:25 and a first mutant detection probe having a nucleotide sequence comprising SEQ ID NO:26, SEQ ID NO:48, or SEQ ID NO:49; and (ii) a second wild type detection probe having a nucleotide sequence comprising SEQ ID NO:45 or SEQ ID NO:47 and a second mutant detection probe having a nucleotide sequence comprising SEQ ID NO:46 or SEQ ID NO:50.

In some embodiments, the present disclosure provides a method for detecting corneal dystrophy, the method comprising: (A) amplifying at least two TGFβI gene sequences, including a first TGFβI gene sequence comprising nucleotides encoding amino acid residue 124 and a second TGFβI gene sequence comprising nucleotides encoding amino acid residue 555, from a biological sample from a human subject using a reaction mixture comprising at least a first amplification primer pair and at least a second amplification primer pair; (B) hybridizing a first detection probes of a first detection oligonucleotide probe pair to the first TGFβI gene sequence; (C) hybridizing a second detection probe of a second detection oligonucleotide probe pair to the second TGFβI gene sequence; and (D) detecting one or more mutations in the first TGFβI gene sequence and/or the second TGFβI gene sequence based on a use of at least two detection probe pairs, including the first detection oligonucleotide probe pair and the second detection oligonucleotide probe pair.

In some embodiments, detecting the one or more mutations in the first TGFβI gene sequence and/or the second TGFβI gene sequence includes detecting two or more mutations in the first TGFβI gene sequence and/or the second TGFβI gene sequence and the two or more mutations are separated in the human genome by at least one nucleotide.

In some embodiments, the at least first amplification primer pair comprises a first amplification primer and a second amplification primer, wherein the first amplification primer comprises nucleotide sequence SEQ ID NO:1 and wherein the second amplification primer comprises nucleotide sequence SEQ ID NO:2.

In some embodiments, the at least second amplification primer pair comprises a third amplification primer and a fourth amplification primer, wherein the third amplification primer is represented by nucleotide sequence SEQ ID NO:43, and wherein the fourth amplification primer is represented by nucleotide sequence SEQ ID NO:44.

In some embodiments, the first amplification primer pair comprises a first amplification primer and a second amplification primer, the first amplification primer comprises nucleotide sequence SEQ ID NO:1, the second amplification primer comprises nucleotide sequence SEQ ID NO:2, the second amplification primer pair comprises a third amplification primer and a fourth amplification primer, the third amplification primer comprises nucleotide sequence SEQ ID NO:43, and the fourth amplification primer comprises nucleotide sequence SEQ ID NO:44.

In some embodiments, one of the one or more mutations corresponds to, at amino acid 124, arginine mutated to a cysteine (R124C), arginine mutated to a histidine (R124H), and/or arginine mutated to a leucine (R124L) in the encoded TGFBI protein.

In some embodiments, one of the one or more mutations corresponds to, at amino acid 555, arginine mutated to a tryptophan (R555W) and/or arginine mutated to a glutamine (R555Q) in the encoded TGFBI protein.

In some embodiments, each of the at least two detection oligonucleotide probe pairs individually includes a first detection oligonucleotide probe and a second detection oligonucleotide probe, wherein the first detection oligonucleotide probe and the second detection oligonucleotide probe comprise a nucleotide sequence pair individually selected from the group consisting of SEQ ID NOs:25-26, SEQ ID NOs:25 and 48, SEQ ID NOs:25 and 49, SEQ ID NOs:27-28, SEQ ID NOs:29-30, SEQ ID NOs:31-32, SEQ ID NOs:33-34, SEQ ID NOs:35-36, SEQ ID NOs:37-38, SEQ ID NOs:39-40, SEQ ID NOs:41-42, SEQ ID NOs:45-46 and SEQ ID NOs:46-47, SEQ ID NOs: 45 and 50, and SEQ ID NOs: 47 and 50.

In some embodiments, the first detection oligonucleotide probe pair comprises a first detection oligonucleotide probe and a second detection oligonucleotide probe, wherein the first detection oligonucleotide probe and the second detection oligonucleotide probe respectively comprise nucleotide sequence pair SEQ ID NO:25 and SEQ ID NO:26.

In some embodiments, the second detection oligonucleotide probe pair comprises a third detection oligonucleotide probe and a fourth detection oligonucleotide probe, wherein the third detection oligonucleotide probe and the fourth detection oligonucleotide probe respectively comprise nucleotide sequence pair SEQ ID NO:45 and SEQ ID NO:46.

In some embodiments, the second detection oligonucleotide probe pair comprises a third detection oligonucleotide probe and a fourth detection oligonucleotide probe, wherein the third detection oligonucleotide probe and the fourth detection oligonucleotide probe respectively comprise nucleotide sequence pair SEQ ID NO:47 and SEQ ID NO:46.

In some embodiments, the second detection oligonucleotide probe pair comprises a third detection oligonucleotide probe and a fourth detection oligonucleotide probe, wherein the third detection oligonucleotide probe and the fourth detection oligonucleotide probe respectively comprise nucleotide sequence pair SEQ ID NO:25 and SEQ ID NO:48.

In some embodiments, the second detection oligonucleotide probe pair comprises a third detection oligonucleotide probe and a fourth detection oligonucleotide probe, wherein the third detection oligonucleotide probe and the fourth detection oligonucleotide probe respectively comprise nucleotide sequence pair SEQ ID NO:25 and SEQ ID NO:49.

In some embodiments, the second detection oligonucleotide probe pair comprises a third detection oligonucleotide probe and a fourth detection oligonucleotide probe, wherein the third detection oligonucleotide probe and the fourth detection oligonucleotide probe respectively comprise nucleotide sequence pair SEQ ID NO:45 and SEQ ID NO:50.

In some embodiments, the second detection oligonucleotide probe pair comprises a third detection oligonucleotide probe and a fourth detection oligonucleotide probe, wherein the third detection oligonucleotide probe and the fourth detection oligonucleotide probe respectively comprise nucleotide sequence pair SEQ ID NO:47 and SEQ ID NO:50.

In some embodiments, the first detection probe is coupled with a first label and the second detection probe is coupled to a second label.

In some embodiments, the first label is VIC and the second label is FAM.

In some embodiments, the hybridizing (B) and the hybridizing (C) are performed concurrently in a same solution.

In some embodiments, the hybridizing (B) and the hybridizing (C) are performed concurrently or at different time in a same solution or different solutions.

In some embodiments, the present disclosure provides a reaction mixture for detecting corneal dystrophy in a human subject, the reaction mixture comprising: (A) at least a first amplification primer pair and a second amplification primer pair for amplifying and determining (1) a first TGFβI gene sequence of at least two TGFβI gene sequences that comprises nucleotides encoding amino acid residue 124 from a biological sample from the subject and (2) a second TGFβI gene sequence of the at least two TGFβI gene sequences that comprises nucleotides encoding amino acid residue 555 from a biological sample from the subject; and (B) at least two detection probe pairs, wherein a detection probe in each of the at least two detection probe pairs hybridizes to at least one of the at least two TGFβI gene sequences.

In some embodiments, the first amplification primer pair comprises a first amplification primer and a second amplification primer, the first amplification primer comprises a nucleotide sequence SEQ ID NO:1, and the second amplification primer comprises a nucleotide sequence SEQ ID NO:2.

In some embodiments, the second amplification primer pair comprises a third amplification primer and a fourth amplification primer, the third amplification primer comprises a nucleotide sequence SEQ ID NO:43, and the fourth amplification primer comprises a nucleotide sequence SEQ ID NO:44.

In some embodiments, at least one of the at least two detection probe pairs is used to detect a mutation that corresponds to, at amino acid 124, arginine mutated to a cysteine (R124C), arginine mutated to a histidine (R124H), and/or arginine mutated to a leucine (R124L) in the encoded TGFBI protein.

In some embodiments, at least one of the at least two detection probe pairs is used to detect a mutation that corresponds to, at amino acid 555, arginine mutated to a tryptophan (R555W) and/or arginine mutated to a glutamine (R555Q) in the encoded TGFBI protein.

In some embodiments, respective detection probe pairs of the at least two detection probe pairs individually include a first detection oligonucleotide probe and a second detection oligonucleotide probe, wherein the first detection oligonucleotide probe and the second detection oligonucleotide probe comprise a nucleotide sequence pair individually selected from the group consisting of SEQ ID NOs:25-26, SEQ ID NOs:25 and 48, SEQ ID NOs:25 and 49, SEQ ID NOs:27-28, SEQ ID NOs:29-30, SEQ ID NOs:31-32, SEQ ID NOs:33-34, SEQ ID NOs:35-36, SEQ ID NOs:37-38, SEQ ID NOs:39-40, SEQ ID NOs:41-42, SEQ ID NOs: 45-46 and SEQ ID NOs: 46-47, SEQ ID NOs: 45 and 50, and SEQ ID NOs: 47 and 50.

In some embodiments, one of the at least two detection probe pairs comprises a first detection oligonucleotide probe and a second detection oligonucleotide probe, wherein the first detection oligonucleotide probe and the second detection oligonucleotide probe respectively comprise nucleotide sequence pair SEQ ID NO:25 and SEQ ID NO:26.

In some embodiments, one of the at least two detection probe pairs comprises a first detection oligonucleotide probe and a second detection oligonucleotide probe, wherein the first detection oligonucleotide probe and the second detection oligonucleotide probe respectively comprise nucleotide sequence pair SEQ ID NO:45 and SEQ ID NO:46.

In some embodiments, one of the at least two detection probe pairs comprises a first detection oligonucleotide probe and a second detection oligonucleotide probe, wherein the first detection oligonucleotide probe and the second detection oligonucleotide probe respectively comprise nucleotide sequence pair SEQ ID NO:47 and SEQ ID NO:46.

In some embodiments, one of the at least two detection probe pairs comprises a first detection oligonucleotide probe and a second detection oligonucleotide probe, wherein the first detection oligonucleotide probe and the second detection oligonucleotide probe respectively comprise nucleotide sequence pair SEQ ID NO:25 and SEQ ID NO:48.

In some embodiments, one of the at least two detection probe pairs comprises a first detection oligonucleotide probe and a second detection oligonucleotide probe, wherein the first detection oligonucleotide probe and the second detection oligonucleotide probe respectively comprise nucleotide sequence pair SEQ ID NO:25 and SEQ ID NO:49.

In some embodiments, one of the at least two detection probe pairs comprises a first detection oligonucleotide probe and a second detection oligonucleotide probe, wherein the first detection oligonucleotide probe and the second detection oligonucleotide probe respectively comprise nucleotide sequence pair SEQ ID NO:45 and SEQ ID NO:50.

In some embodiments, one of the at least two detection probe pairs comprises a first detection oligonucleotide probe and a second detection oligonucleotide probe, wherein the first detection oligonucleotide probe and the second detection oligonucleotide probe respectively comprise nucleotide sequence pair SEQ ID NO:47 and SEQ ID NO:50.

In some embodiments, a first detection probe of the at least two detection probes is coupled with a first label and a second detection probe of the at least two detection probes is coupled to a second label.

In some embodiments, the first label is VIC and the second label is FAM.

In some embodiments, the present disclosure provides a reaction mixture for detecting corneal dystrophy in a human subject, the reaction mixture comprising: (A) at least a first amplification primer pair for amplifying and determining a TGFβI gene sequence from a biological sample from the subject; and (B) a set of at least three detection probes, wherein one detection probe of the set of at least three detection probes hybridizes to the TGFβI gene sequence when exposed to the TGFβI gene sequence.

In some embodiments, the TGFβI gene sequence comprises nucleotides encoding amino acid residue 124 from the biological sample from the subject.

In some embodiments, the set of at least three detection probes include at least one detection probe selected from the group consisting of SEQ ID NOs:25-42 and 48-49.

In some embodiments, the set of at least three detection probes include at least two or more detection probes selected from the group consisting of SEQ ID NOs:25-42 and 48-49.

In some embodiments, the set of at least three detection probes include at least three or more detection probes selected from the group consisting of SEQ ID NOs:25-42 and 48-49.

In some embodiments, the set of at least three detection probes include a first detection probe SEQ ID NO:25 and a second detection probe SEQ ID NO:26.

In some embodiments, the set of at least three detection probes include a third detection probe selected from the group consisting of SEQ ID NO:48 and SEQ ID NO:49.

In some embodiments, the set of at least three detection probes include a fourth detection probe that is distinct from the third detection probe and that is selected from the group consisting of SEQ ID NO:48 and SEQ ID NO:49.

In some embodiments, the set of at least three detection probes include two or more detection probes selected from the group consisting of SEQ ID NOs:26 and 48-49.

In some embodiments, the first amplification primer pair comprises a first amplification primer and a second amplification primer, the first amplification primer comprises a nucleotide sequence SEQ ID NO:1, and the second amplification primer comprises a nucleotide sequence SEQ ID NO:2.

In some embodiments, the reaction mixture further comprises: (C) at least a second amplification primer pair for amplifying and determining a second TGFβI gene sequence from the biological sample; and (D) a second set of at least three detection probes, wherein one detection probe of the second set of at least three detection probes hybridizes the second TGFβI gene sequence when exposed to the second TGFβI gene sequence.

In some embodiments, the second TGFβI gene sequence comprises nucleotides encoding amino acid residue 555 from the biological sample from the subject.

In some embodiments, the second set of at least three detection probes include at least one detection probe selected from the group consisting of SEQ ID NOs: 45-47 and 50.

In some embodiments, the second set of at least three detection probes include at least two or more detection probes selected from the group consisting of SEQ ID NOs: 45-47 and 50.

In some embodiments, the second set of at least three detection probes include at least three or more detection probes selected from the group consisting of SEQ ID NOs: 45-47 and 50.

In some embodiments, the second set of at least three detection probes include a first detection probe that is SEQ ID NO:45 or SEQ ID NO:47, a second detection probe that is SEQ ID NO:46, and a third detection probe that is SEQ ID NO:50.

In some embodiments, the second amplification primer pair comprises a third amplification primer and a fourth amplification primer, the third amplification primer comprises a nucleotide sequence SEQ ID NO:43, and the fourth amplification primer comprises a nucleotide sequence SEQ ID NO:44.

In some embodiments, the TGFβI gene sequence comprises nucleotides encoding amino acid residue 555 from the biological sample from the subject.

In some embodiments, the set of at least three detection probes include at least one detection probe selected from the group consisting of SEQ ID NOs:45-47 and 50.

In some embodiments, the set of at least three detection probes include at least two or more detection probes selected from the group consisting of SEQ ID NOs: 45-47 and 50.

In some embodiments, the set of at least three detection probes include at least three or more detection probes selected from the group consisting of SEQ ID NOs: 45-47 and 50.

In some embodiments, the set of at least three detection probes include a first detection probe that is SEQ ID NO:45 or SEQ ID NO:47, a second detection probe that is SEQ ID NO:46, and a third detection probe that is SEQ ID NO:50.

In some embodiments, the present disclosure provides a method for detecting corneal dystrophy comprising: (A-1) amplifying a first TGFβI gene sequence from a biological sample from a human subject using a reaction mixture comprising at least a first amplification primer pair and a set of at least three detection probes; (B-1) hybridizing a first detection probe of the set of at least three detection probes to the first TGFβI gene sequence; and (C-1) detecting a mutation in the first TGFβI gene sequence based on (i) the hybridization of the first detection probe of the set of at least three detection probes to the first TGFβI gene sequence and (ii) the failure of a second and a third detection probe of the set of at least three detection probes to hybridize to first TGFβI gene sequence.

In some embodiments, the method further comprises: (A-2) amplifying a second TGFβI gene sequence from the biological sample using the same reaction mixture, wherein the reaction mixture comprises at least a second amplification primer pair and a second set of at least three detection probes; (B-2) hybridizing a first detection probe of the second set of at least three detection probes to the second TGFβI gene sequence; and (C-2) detecting a mutation in the second TGFβI gene sequence based on (i) the hybridization of the first detection probe of the second set of at least three detection probes to the first TGFβI gene sequence and (ii) and (ii) the failure of a second detection probe and a third detection probe of the second set of at least three detection probes to hybridize to the second TGFβI gene sequence.

In some embodiments, the amplifying (A-1), the amplifying (A-2), the hybridizing (B-1), the hybridizing (B-2), the detecting (C-1), and the detecting (C-2) are performed with a same aliquot of the biological sample.

In some embodiments, the amplifying the first TGFβI gene sequence (A-1) and the amplifying the second TGFβI gene sequence (A-2) are performed concurrently.

In some embodiments, the hybridizing (B-1) and the hybridizing (B-2) are performed concurrently.

In some embodiments, the detecting (C-1) and the detecting (C-2) are performed concurrently.

In some embodiments, the reaction mixture has some of the features described above. For brevity, such details are not repeated herein.

In some embodiments, the present disclosure provides use of a reaction mixture, as recited in any above, for predicting the risk of complication following laser eye surgery in a subject through a detection of heterozygous corneal dystrophy in the human subject.

In some embodiments, the laser eye surgery comprises one of Lasik and Excimer laser surgery.

In some embodiments, the present disclosure provides a method for detecting a genomic mutation associated with corneal dystrophy in a sample from a human subject, the method comprising: (A) providing epithelial cells of a human subject adhered to a tip of a substrate; (B) agitating the tip of the substrate in a lysis solution that lyses cells adhered to the substrate; (C) removing the substrate from the lysis solution upon completion of the agitating (B); (D) incubating the lysis solution after the removing (C); (E) isolating genomic DNA from the lysis solution to form a gDNA solution; and (F) determining an identity of at least a nucleotide present in the TGFβI gene using at least a first primer pair, a set of at least three detection probes, and the gDNA solution by concurrently exposing the gDNA solution to the at least three detection probes, wherein: the at least a nucleotide is located at a particular position of the TGFβI gene corresponding to a single nucleotide polymorphism (SNPs) associated with corneal dystrophy, and each of at least two detection probes of the set of the at least three detection probes is configured to detect a different mutation at the particular position of the TGFβI gene.

In some embodiments, the method further comprises: (G) determining an identity of at least a second nucleotide present in the TGFβI gene using at least a second primer pair, a second set of at least three detection probes, and the gDNA solution by concurrently exposing the gDNA solution to the set of at least three detection probes and the second set of at least three detection probes, wherein: the at least a second nucleotide is located at a second particular position, independent of the position of the at least a nucleotide, of the TGFβI gene corresponding to a second single nucleotide polymorphism (SNPs) associated with corneal dystrophy, and at least two detection probes of the second set of the at least three detection probes are configured to detect a respective mutation at the second particular position of the TGFβI gene.

In some embodiments, the determining (F) and the determining (G) are performed concurrently.

In some embodiments, the determining (F) and the determining (G) are performed using the same gDNA solution.

BRIEF DESCRIPTION OF THE DRAWINGS

FIG. 2 provides a list of sequences for forward and reverse PCR primer pairs (SEQ ID NOs:1-24) useful for real-time PCR detection of a single nucleotide polymorphism associated with Avellino corneal dystrophy, in accordance with some embodiments.

FIG. 3 provides a list of sequences for wild type and mutant detection probe pairs (SEQ ID NOs:25-42) useful for real-time PCR detection of a single nucleotide polymorphism associated with Avellino corneal dystrophy, in accordance with some embodiments.

FIG. 4 provides a list of the probe sequences and primers used in the allele detection experiments shown in FIGS. 5 through 8.

FIGS. 5A, 5B, and 5C provide experimental data regarding detection of the R124C, R124H, R124L, R555W and R555Q mutants using the probes described in FIG. 4. FIG. 5A provides an allelic discrimination plot run (left-hand panel) using the indicated reagent mixture and indicated cycling conditions (right-hand panel). FIG. 5B provides the Real-Time PCR plots for the various mutants compared to a normal control. FIG. 5C provides the Real-Time PCR plots for the various mutants compared to a homozygous control.

FIGS. 6A, 6B, and 6C provide experimental data regarding detection of the R124C, R124H, R124L, R555W and R555Q mutants using the probes described in FIG. 4. FIG. 6A provides an allelic discrimination plot run (left-hand panel) using the indicated reagent mixture and indicated cycling conditions (right-hand panel). FIG. 6B provides the Real-Time PCR plots for the various mutants compared to a normal control. FIG. 6C provides the Real-Time PCR plots for the various mutants compared to a homozygous control.

FIG. 7 provides an allelic discrimination plot (left-hand panel) run using the indicated reagent mixture and indicated cycling conditions (right-hand panel).

DETAILED DESCRIPTION

I. Introduction

Figure 1A:
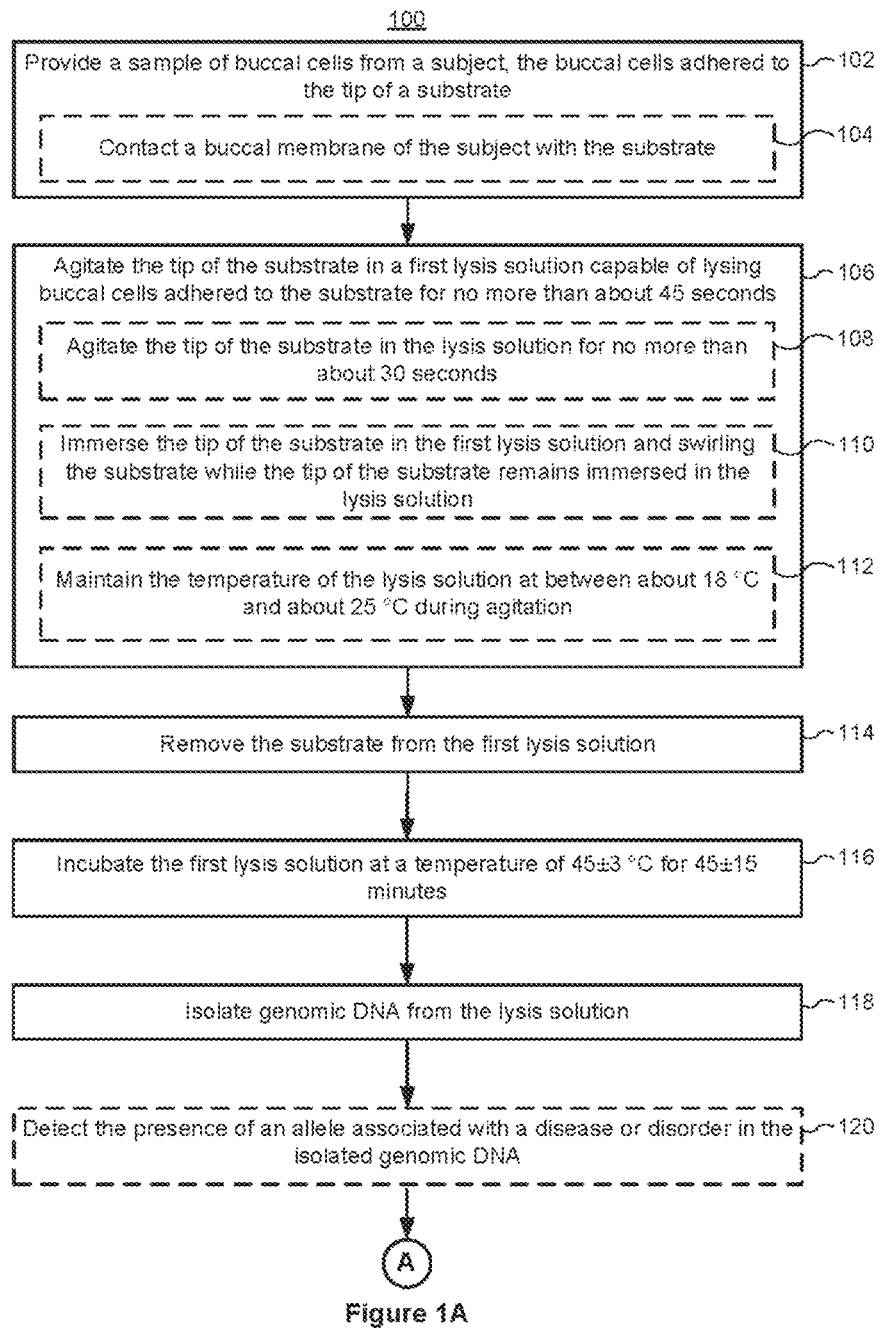
FIGS. 1A-1B illustrate an improved method 100 for the detection of genomic alleles associated with disease, according to some embodiments.

The detection of disease-related SNPs is an increasingly more important tool for the diagnosis and prognosis of various medical conditions. For example, the presence of a single nucleotide change in exon 4 of the TGFβI gene is strongly associated with Avellino corneal dystrophy. It was found that individuals heterozygous for this SNP are at high risk for vision loss following LASIK surgery. While LASIK is a medical procedure that greatly improves many people's quality of life, for individuals carrying the G/A TGFβI SNP, it commonly causes a gradual vision impairment over a four to eighteen month period, which may lead to loss of vision.

The vision impairment may occur in a longer or shorter period of time. Fortunately, screening can be performed to identify individuals carrying the mutation who should avoid having the LASIK procedure.

The present disclosure is based at least in part on the discovery of methods that improve sample isolation, preparation, and analysis. In some embodiments, methods are provided which allow for the re-use of patient samples, for example, when an assay fails or additional follow-up testing needs to be performed. In some embodiments, these improved methods include gently swirling a substrate (e.g., a rayon-tipped or cotton-tipped applicator) carrying cells sloughed-off the buccal membrane of the patient in a lysis solution at room temperature for 30-45 seconds (rather than extended incubation for 20 minutes at elevated temperature). The lysis solution is then incubated at 45° C. for 30 minutes to improve lysis and increase the yield of genomic sample. Advantageously, the rayon-tipped or cotton-tipped applicator can then be stored (e.g., frozen or refrigerated) for re-isolation of genomic DNA used for re-testing.

In some embodiments, the improvements provided herein are provided through the use of lower amounts of genomic DNA template for the real-time PCR detection assays. In some embodiments, this is achieved by increasing the number of real-time PCR cycles performed (e.g., at about 40 cycles) and/or by using 3 second denaturation cycle times at 95° C. Advantageously, because the amount of sample required is reduced by these methods, so too are the requirements for the real-time PCR reagents. Because many reagents used in diagnostic assays are proprietary, the reagents can be expensive. Reducing the amount of reagent used can also significantly reduce the costs associated with the reagent.

It is contemplated that all combinations of specific conditions (e.g., sample handling, incubation temperature, reaction volumes, reaction cycle numbers, reaction cycle times, reaction cycle temperatures) for performing each of these individual steps can be used to perform the methods described herein for detecting disease-related SNPs, such as the Avellino corneal dystrophy-related SNP found in exon 4 of the TGFβI gene.

II. Select Definitions

The term "invention" or "present invention" as used herein is not meant to be limiting to any one specific embodiment of the invention but applies generally to any and all embodiments of the invention as described in the claims and specification.

As used herein, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure.

As used herein, the term "polymorphism" and variants thereof refers to the occurrence of two or more alternative genomic sequences or alleles between or among different genomes or individuals. The terms "genetic mutation" or "genetic variation" and variants thereof include polymorphisms.

As used herein the term "single nucleotide polymorphism" ("SNP") and variants thereof refers to a site of one nucleotide that varies between alleles. A single nucleotide polymorphism (SNP) is a single base change or point mutation but also includes the so-called "indel" mutations (insertions or deletions of a nucleotide), resulting in genetic variation between individuals. SNPs, which make up about 90% of all human genetic variation, occur every 100 to 300 bases along the 3-billion-base human genome. However, SNPs can occur much more frequently in other organisms like viruses. SNPs can occur in coding or non-coding regions of the genome. A SNP in the coding region may or may not change the amino acid sequence of a protein product. A SNP in a non-coding region can alter promoters or processing sites and may affect gene transcription and/or processing. Knowledge of whether an individual has particular SNPs in a genomic region of interest may provide sufficient information to develop diagnostic, preventive and therapeutic applications for a variety of diseases. In some embodiments, the present disclosure relates to the detection of a guanine-to-adenine SNP located in exon 4 of the TGFβI gene associated with Avellino corneal dystrophy.

The term "primer" and variants thereof refers to an oligonucleotide that acts as a point of initiation of DNA synthesis in a PCR reaction. A primer is usually about 15 to about 35 nucleotides in length and hybridizes to a region complementary to the target sequence.

The term "probe" and variants thereof (e.g., detection probe) refers to an oligonucleotide that hybridizes to a target nucleic acid in a PCR reaction. Target sequence refers to a region of nucleic acid that is to be analyzed and comprises the polymorphic site of interest.

Unless defined otherwise, all technical and scientific terms used herein have the same meaning as commonly understood by those of ordinary skill in the art to which the invention pertains. Although any methods and materials similar or equivalent to those described herein can be used in the practice or testing of the present invention, various embodiments of methods and materials are specifically described herein.

III. Sample Preparation

Figure 1B:
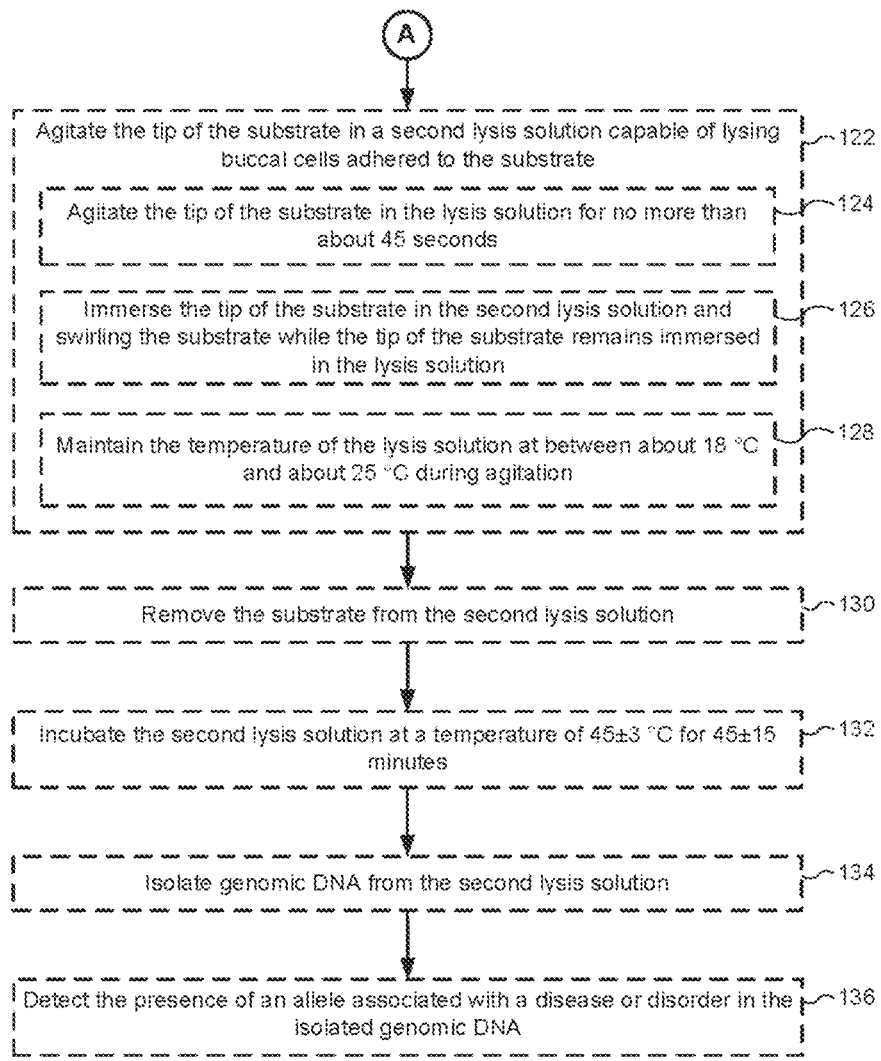
Figure 5A:
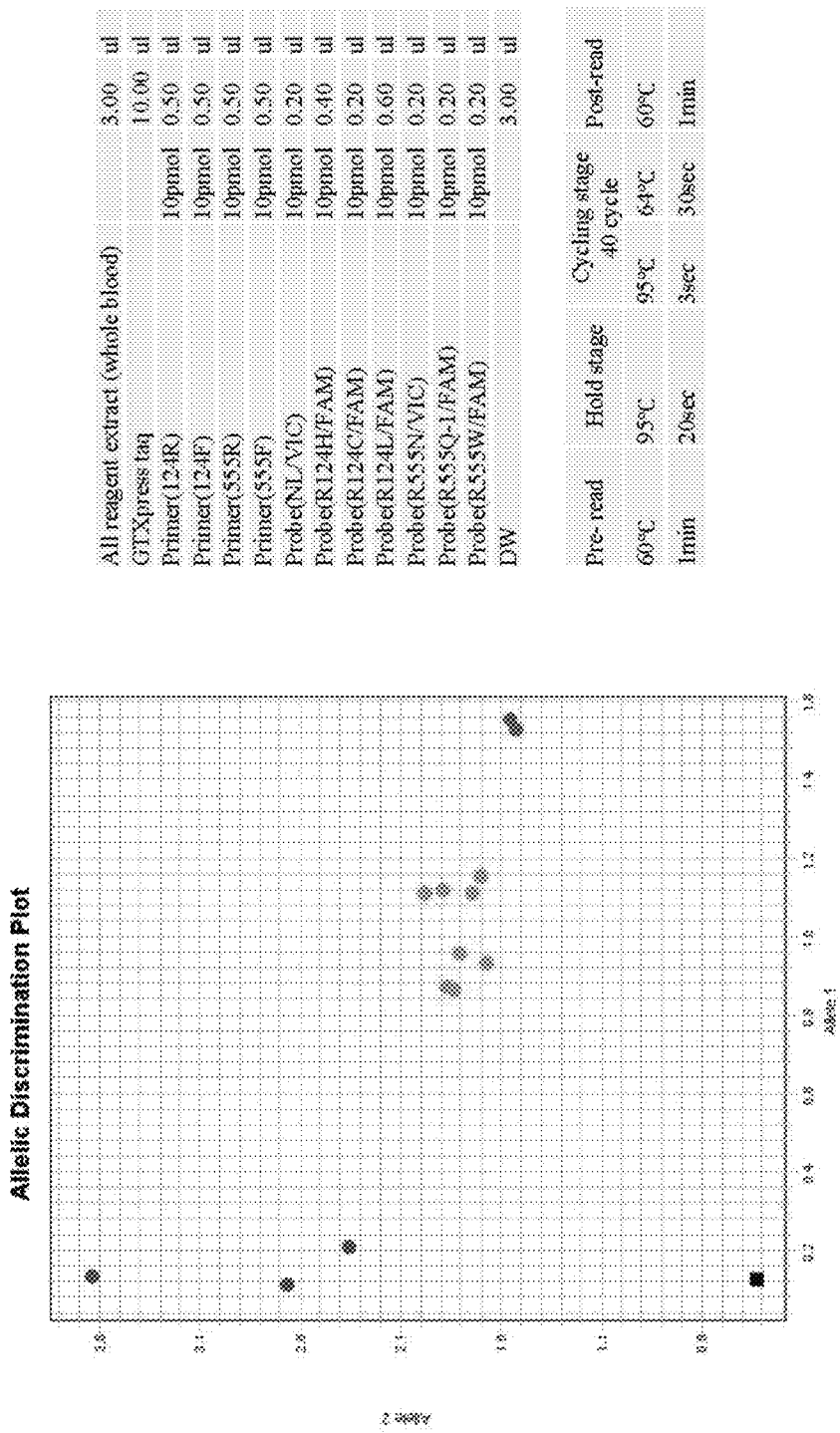
Figure 6A:
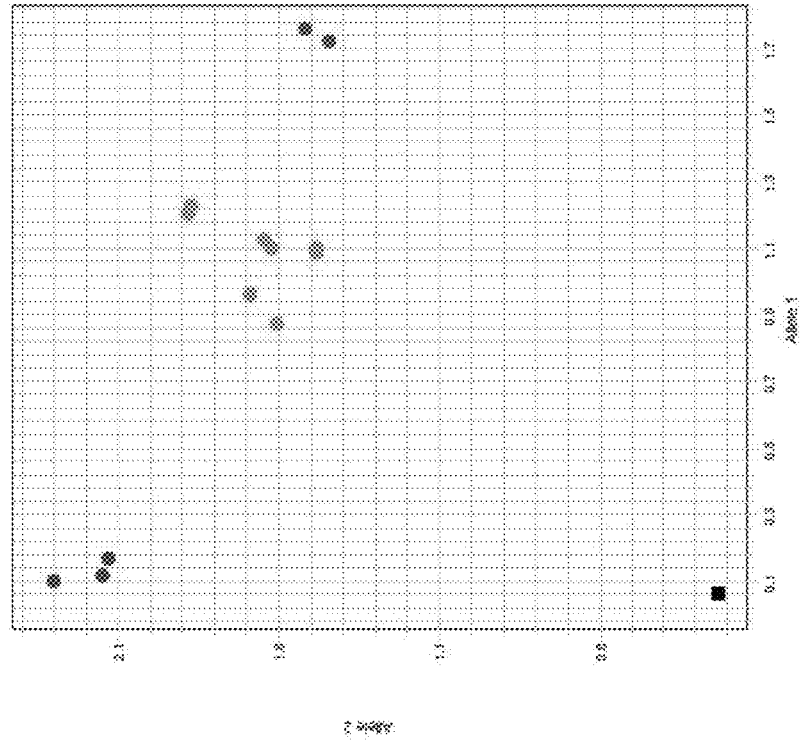
Figure 6C:
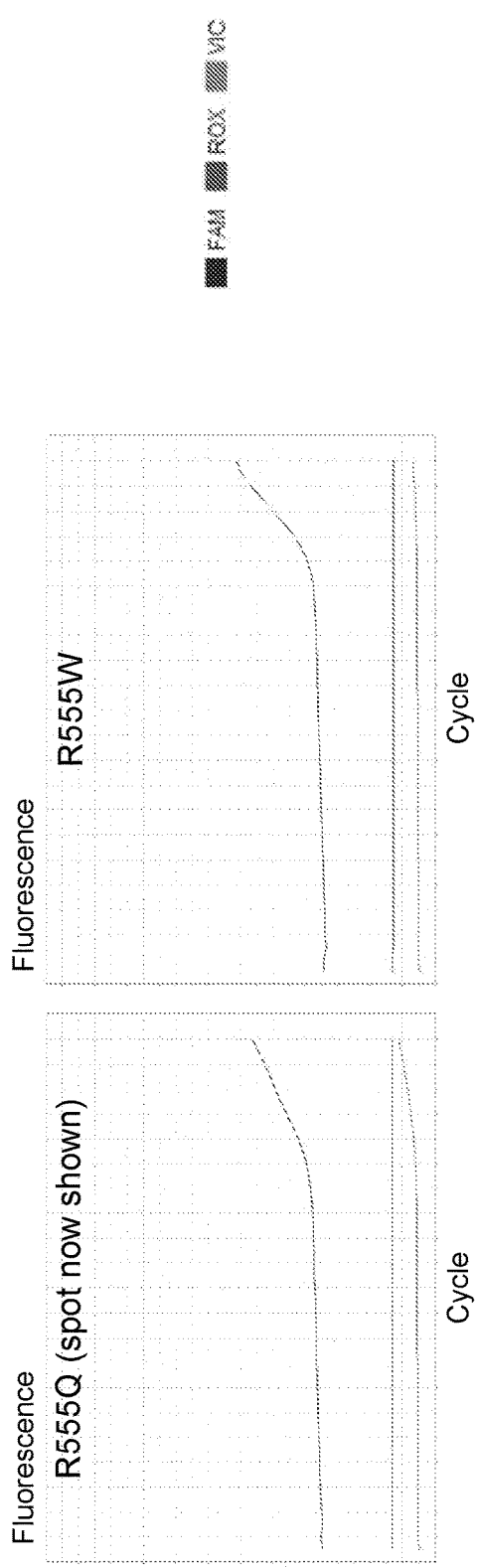
Figure 7:
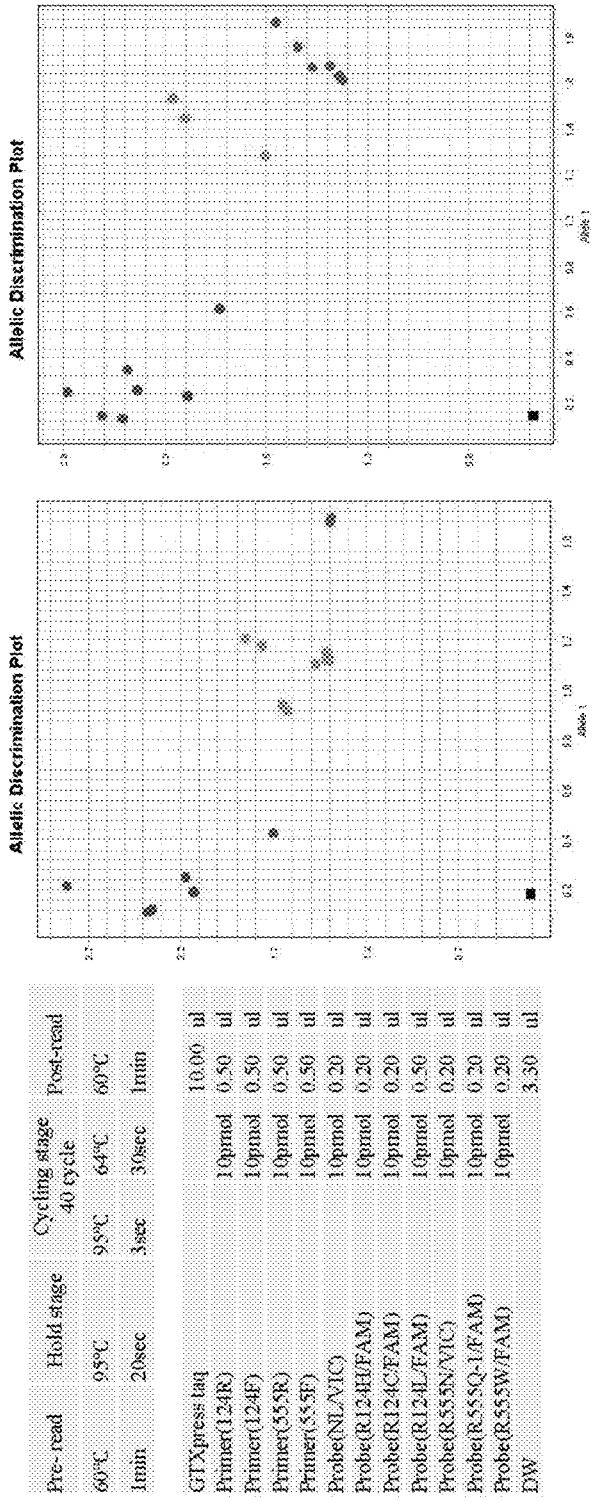
FIG. 7 provides experimental data regarding detection of the R124C, R124H, R124L, R555W and R555Q mutants using the probes described in FIG. 4.
Figure 8:
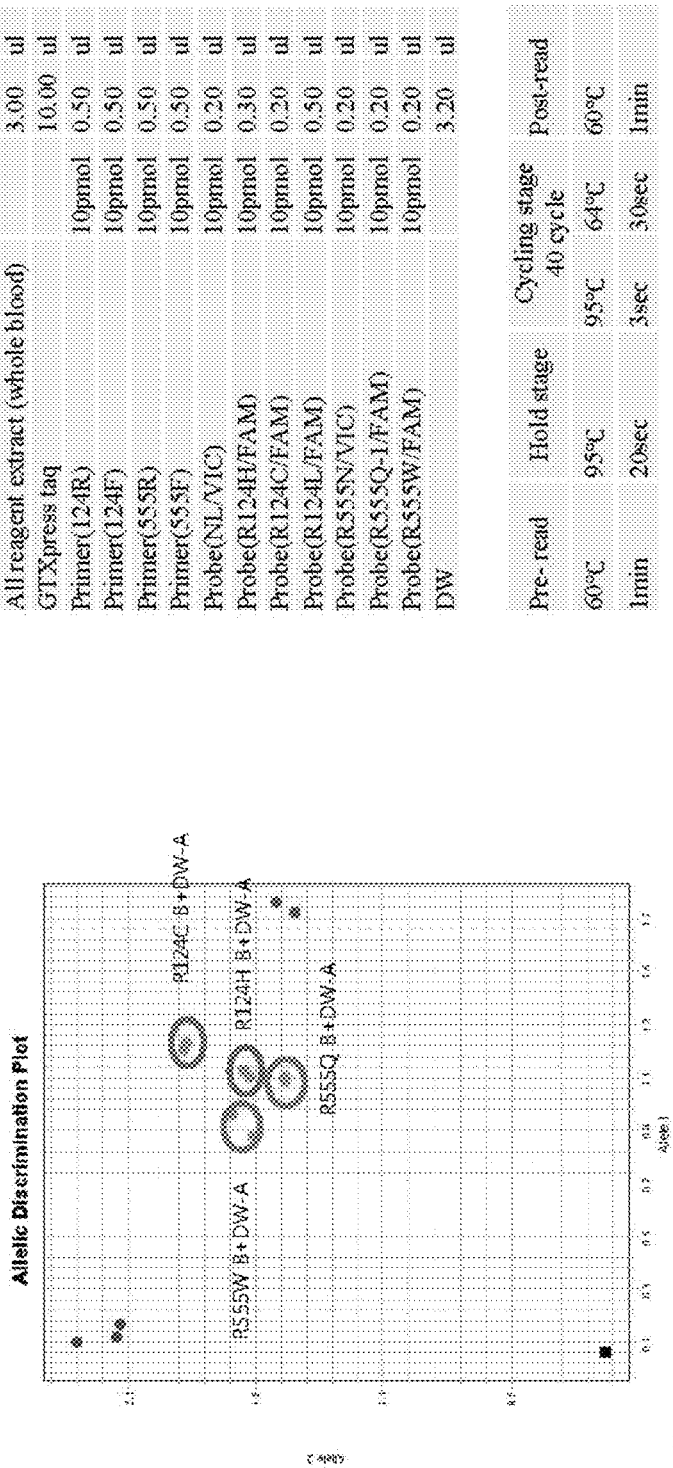
FIG. 8 provides experimental data regarding detection of the R124C, R124H, R124L, R555W and R555Q mutants using the probes described in FIG. 4. In particular, FIG. 8 provides an allelic discrimination plot run using the indicated reagent mixture and indicated cycling conditions (right-hand panel). The designation "B" in the allelic discrimination plot (left-hand panel) indicates samples were pre-treated with lysis buffer prior to performing the Real-Time PCR assay. The designation "DW-A" in the allelic discrimination plot (left-hand panel) indicates samples were pre-treated with distilled water prior to performing the Real-Time PCR assay. The circles surrounding the different sample dots show the two matched samples, "B" and "DW-A" respectively, for each of the alleles detected (see, the left-hand panel); there are two dots within each circle, one for sample "B" and one for sample "DW-A".

In some embodiments, the disclosure provides improved methods for isolating genomic samples used in real-time PCR single nucleotide polymorphism detection assays. In some embodiments, the improved method 100 uses a combination of steps outlined in FIG. 1.

In some embodiments, the method includes providing a sample of cells from a subject. In some embodiments, the cells are collected by contacting a cellular surface of a patient with a substrate capable of reversibly immobilizing the cells onto a substrate.

The disclosed methods are applicable to a variety of cell types obtained from a variety of samples. In some embodiments, the cell type for use with the disclosed methods include but is not limited to epithelial cells, endothelial cells, connective tissue cells, skeletal muscle cells, endocrine cells, cardiac cells, urinary cells, melanocytes, keratinocytes, blood cells, white blood cells, buffy coat, hair cells (including, e.g., hair root cells) and/or salival cells. In some embodiments, the cells are epithelial cells. In some embodiments, the cells are subcapsular-perivascular (epithelial type 1); pale (epithelial type 2); intermediate (epithelial type 3); dark (epithelial type 4); undifferentiated (epithelial type 5); and large-medullary (epithelial type 6). In some embodiments, the cells are buccal epithelial cells (e.g., epithelial cells collected using a buccal swap). In some embodiments, the sample of cells used in the disclosed methods include any combination of the above identified cell types.

In some embodiments, the method includes providing (102) a sample of cells from a subject. In some embodiments, the cells provided are buccal epithelial cells.

The cell sample is collected by any of a variety of methods which allow for reversible binding of the subjects cells to the substrate. In some embodiments, the substrate is employed in a physical interaction with the sample containing the subject's cells in order to reversibly bind the cells to the substrate. In some embodiments, the substrate is employed in a physical interaction with the body of the subject directly in order to reversibly bind the cells to the substrate. In some embodiments, the sample is a buccal cell sample and the sample of buccal cells is collected by contacting a buccal membrane of the subject (e.g., the inside of their cheek) with a substrate capable of reversibly immobilizing cells that are dislodged from the membrane. In such embodiments, the swab is rubbed against the inside of the subject's cheek with a force equivalent to brushing a person's teeth (e.g., a light amount of force or pressure). Any method which would allow the subject's cells to be reversibly bound to the substrate is contemplated for use with the disclosed methods.

In some embodiments, the sample is advantageously collected in a non-invasive manner and as such sample collection is accomplished anywhere and by almost anyone. For example, in some embodiments the sample is collected at a physician's office, at a subject's home, or at a facility where LASIK surgery is performed or to be performed. In some embodiments the patient, the patient's doctor, nurses or a physician's assistant or other clinical personnel collects the sample.

In some embodiments the substrate is made of any of a variety of materials to which cells are reversibly bound. Exemplary substrates include those made of rayon, cotton, silica, an elastomer, a shellac, amber, a natural or synthetic rubber, cellulose, BAKELITE, NYLON, a polystyrene, a polyethylene, a polypropylene, a polyacrylonitrile, or other materials or combinations thereof. In some embodiments, the substrate is a swab having a rayon tip or a cotton tip.

The tip of the substrate (e.g., the tip of the rayon swab or cotton swab) is then agitated in a lysis solution from about 10 seconds to 60 seconds (1 minute), or about 20 seconds to 60 seconds, about 20 seconds to about 45 seconds, or about 20 seconds to about 30 seconds, about 15 seconds to about 60 seconds, about 15 seconds to about 45 seconds, or about 15 seconds to about 30 seconds, about 10 seconds to about 60 seconds, about 10 seconds to about 45 seconds, or about 10 seconds to about 30 seconds, about 10 seconds to about 15 seconds or about 10 seconds to about 20 seconds. In some embodiments, the agitation occurs for about 60 seconds or about 1 minute. In some embodiments, the agitation occurs for less than a minute (e.g., less than 60 seconds). In some embodiments, the agitation occurs for no more than 15 seconds, 20 seconds, 30 seconds, 45 seconds, 60 seconds, 90 seconds, 120 seconds or more. In some embodiments, the agitation occurs for no more than 45 seconds. In some embodiments, the agitation occurs for no more than 30 seconds. In some embodiments, the agitation occurs for no more than 20 seconds. In some embodiments, the agitation occurs for no more than 15 seconds.

In some embodiments, agitation includes any movement of the substrate in the lysis solution. In some embodiments, the tip of the substrate (e.g., the tip of the rayon swab or cotton swab) is moved gently in the lysis solution, such that a plurality of buccal cells remains affixed to the substrate for isolation at a later time and/or subsequent time. Such movement in the lysis solution includes swirling motions, side to side motions, up and down motions and/or dipping motions, or any other movement of the substrate in the lysis solutions that results in a plurality of buccal cell remain affixed to the tip while allowing for some buccal cells to be dispersed into the lysis solution.

In some embodiments, the agitation step is performed at room temperature, for instance, temperatures between about 15° C. and about 30° C., about 18° C. and about 28° C., about 18° C. and about 25° C. or about 20° C. and about 25° C.

After agitation, the substrate (e.g., a swab with a rayon tip or cotton tip) is removed and, in some embodiments, stored for use later, in case re-testing or further (e.g., different or additional) testing is needed. In some embodiments, the substrate (e.g., buccal swab with a rayon tip or cotton tip) is placed in a container and stored frozen. In some embodiments, the substrate (e.g., buccal swab with a rayon tip or cotton tip) is refrigerated. In some embodiments, the substrate is stored at any of a variety of temperatures and for any of a variety of times while still remaining useful for one or more additional extractions.

In some embodiments, the substrate containing the sample is stored for 0 weeks, 1 week, 2 weeks, 3 weeks, 4 weeks, 5 weeks, 6 weeks, 7 weeks, 8 weeks, 9 weeks, 10 weeks, 11 weeks or 12 weeks or more. In some embodiments, the substrate containing the sample is stored for and/or is capable of being stored for 0 weeks to 12 weeks, 1 week to 12 weeks, 2 weeks to 12 weeks, 3 weeks to 12 weeks, 4 weeks to 12 weeks, 5 weeks to 12 weeks, 6 weeks to 12 weeks, 7 weeks to 12 weeks, 8 weeks to 12 weeks, 9 weeks, 10 weeks to 12 weeks, or 11 weeks to 12 weeks. In some embodiments, the substrate containing the sample is stored for 1, 2, 3, 4, 5, 6, 8, 10, 12, 14, 16, 18, 20, 22, 24, 30, or 36 months or more. In some embodiments, the substrate containing the sample is stored for 1 month to 36 months, 2 months to 36 months, 3 months to 36 months, 4 months to 36 months, 5 months to 36 months, 6 months to 36 months, 7 months to 36 months, 8 months to 36 months, 9 months to 36 months, 10 months to 36 months, 12 months to 36 months, 14 months to 36 months, 16 months to 36 months, 18 months to 36 months. In some embodiments, the substrate containing the sample is stored for 1 month to 30 months, 2 months to 30 months, 3 months to 30 months, 4 months to 30 months, 5 months to 30 months, 6 months to 30 months, 7 months to 30 months, 8 months to 30 months, 9 months to 30 months, 10 months to 30 months, 12 months to 30 months, 14 months to 30 months, 16 months to 30 months or 18 months to 30 months. In some embodiments, the substrate containing the sample is stored for 1 month to 24 months, 2 months to 24 months, 3 months to 24 months, 4 months to 24 months, 5 months to 24 months, 6 months to 24 months, 7 months to 24 months, 8 months to 24 months, 9 months to 24 months, 10 months to 24 months, 12 months to 24 months, 14 months to 24 months, 16 months to 24 months, 18 months to 24 months. In some embodiments, the substrate containing the sample is stored for 1 month to 22 months, 2 months to 22 months, 3 months to 22 months, 4 months to 22 months, 5 months to 22 months, 6 months to 22 months, 7 months to 22 months, 8 months to 22 months, 9 months to 22 months, 10 months to 22 months, 12 months to 22 months, 14 months to 22 months, 16 months to 22 months, 18 months to 22 months. In some embodiments, the substrate containing the sample is stored for 1 month to 20 months, 2 months to 20 months, 3 months to 20 months, 4 months to 20 months, 5 months to 20 months, 6 months to 20 months, 7 months to 20 months, 8 to 20 months, 9 to 20 months, 10 months to 20 months, 12 months to 20 months, 14 months to 20 months, 16 months to 20 months, 18 months to 20 months. In some embodiments, the substrate containing the sample is stored for 1 month to 18 months, 2 months to 18 months, 3 months to 18 months, 4 months to 18 months, 5 months to 18 months, 6 months to 18 months, 7 months to 18 months, 8 months to 18 months, 9 months to 18 months, 10 months to 18 months, 12 months to 18 months, 14 months to 18 months, 16 months to 18 months or 17 months to 18 months. In some embodiments, the substrate containing the sample is stored for 1 month to 12 months, 2 months to 12 months, 3 months to 12 months, 4 months to 12 months, 5 months to 12 months, 6 months to 12 months, 7 months to 12 months, 8 months to 12 months, 9 months to 12 months, 10 months to 12 months or 11 months to 12 months.

In some embodiments, the substrate containing the sample is stored at about 2° C., about 3° C., about 4° C., about 5° C., about 6° C., about 7° C., or about 8° C. In some embodiments, the substrate containing the sample is stored at about 2° C. to about 8° C., about 3° C. to about 8° C., about 4° C. to about 8° C., about 5° C. to about 8° C., about 6° C. to about 8° C. or about 7° C. to about 8° C. In some embodiments, the substrate containing the sample is stored at about −25° C., about −24° C., about −23° C., about −22° C., about −21° C., about −20° C., about −19° C., about −18° C., about −17° C., about −16° C. or about −15° C. In some embodiments, the substrate containing the sample is stored at about −25° C. to about −15° C., about −22° C. to about −17° C., about −20° C. to about −15° C. or about −25° C. to about −20° C. In some embodiments, the substrate containing the sample is stored at about −90° C., about −89° C., about −88° C., about −87° C., about −86° C., about −85° C., about −84° C., about −83° C., about −82° C., about −81° C., about −80° C., about −79° C., about −78° C., about −77° C., about −76° C., about −75° C., about −74° C., about −73° C., about −72° C., about −71° C., about −70° C., about −69° C., about −68° C., about −67° C., about −66° C. or about −65° C. In some embodiments, the substrate containing the sample is stored at about −90° C. to about −65° C., about −85° C. to about −65° C., about −80° C. to about −65° C., about −75° C. to about −65° C. or about −70° C. to about −65° C. In some embodiments, the substrate containing the sample is stored at −90° C. to −65° C.

In some embodiments, the substrate containing the sample is freeze-thawed one or more times (e.g., after being frozen, the substrate containing the sample is thawed, used according to the present methods and re-frozen) and or used in the present methods. In some embodiments, the substrate containing the sample is freeze-thawed 1, 2, 3, 4, 5, 6, 7, 8, 9, 10, 11, 12, 13, 14, 15, 16, 17, 18, 19, 20 or more times. In some embodiments, the substrate containing the sample is used in the present methods 1, 2, 3, 4, 5, 6, 7, 8, 9, 10, 11, 12, 13, 14, 15, 16, 17, 18, 19, 20 or more times. In some embodiments, the substrate containing the sample is freeze-thawed 1 to 20 times, 2 to 20 times, 3 to 20 times, 4 to 30 times, 5 to 20 times, 6 to 20 times, 7 to 20 times, 8 to 20 times, 9 to 20 times, 10 to 20 times, 11 to 20 times, 12 to 20 times, 13 to 20 times, 14 to 20 times, 15 to 20 times, 16 to 20 times, 17 to 20 times, 18 to 20 times, 19 to 20 times, 5 to 15 times, 5 to 10 times, 1 to 10 times or 1 to 5 times. In some embodiments, the substrate containing the sample is used in the present methods 1 to 20 times, 2 to 20 times, 3 to 20 times, 4 to 30 times, 5 to 20 times, 6 to 20 times, 7 to 20 times, 8 to 20 times, 9 to 20 times, 10 to 20 times, 11 to 20 times, 12 to 20 times, 13 to 20 times, 14 to 20 times, 15 to 20 times, 16 to 20 times, 17 to 20 times, 18 to 20 times, 19 to 20 times, 5 to 15 times, 5 to 10 times, 1 to 10 times, 1 to 5 times, 1 to 4 times, 1 to 3 times or 1 to 2 times.

In some embodiments, the substrate containing the sample is stored for 1 week at room temperature or about 15° C. to about 30° C. In some embodiments, the sample is stored for about 1, 2 or 3 weeks at about 2° C. to about 8° C. or about 4° C. In some embodiments, the substrate containing the sample is stored for about 1, 2, 3, 4, 5, 6, 7, 8, 9, 10, 11 or 12 months at about −25° C. to about −15° C. or about −20° C. In some embodiments, the substrate containing the sample is stored for about 1, 2, 3, 4, 5, 6, 7, 8, 9, 10, 11 or 12 months at about −90° C. to about −65° C. or about −80° C.

Advantageously and surprisingly, it was found that the reduced number of cells extracted from the substrate is countered by increased extraction of nucleic acids from individual cells. In some embodiments, increased extraction is accomplished by incubating the cells for a longer time as compared to standard practices, incubating the cells at an elevated temperature as compared to standard practices, or a combination of both.

In some embodiments, the increased extraction of nucleic acids of cells is accomplished by performing the extraction incubation for an increased or longer period of time as compared to standard practice. In some embodiments, the extraction incubation is performed for about 45 minutes, e.g., 45±5, 45±10, 45±15, or 45±20 minutes. In some embodiments, the extraction incubation is performed for about 25 minutes to about 65 minutes, about 30 minutes to about 60 minutes, about 35 minutes to about 55 minutes, about 45 minutes to about 65 minutes, about 45 minutes to about 55 minutes, or about 40 minutes to about 50 minutes. In some embodiments, the extraction incubation time is about 25 minutes, about 30 minutes, about 35 minutes, about 40 minutes, about 45 minutes, about 50 minutes, about 55 minutes, about 60 minutes or about 65 minutes.

In some embodiments, the increased the extraction of nucleic acids of cells is accomplished by performing the extraction incubation at an increased or higher temperature as compared to standard practice. In some embodiments, the extraction incubation is performed at about 45° C., e.g., 45±2° C., 45±5° C., or 45±10° C. In some embodiments, the extraction incubation temperature is about 35° C. to about 55° C., about 40° C. to about 50° C. or about 43° C. to about 47° C. In some embodiments, the extraction temperature is about 43° C., about 44° C., about 45° C., about 46° C., about 47° C., about 48° C., about 49° C., about 50° C., about 51° C., about 52° C., about 53° C., about 54° C. or about 55° C. In some embodiments, more than one extraction temperature is used. For example in some embodiments, standard temperatures are used for a portion of the extraction and an elevated temperature is used for another portion of the extraction.

In some embodiments, substantially small numbers of cells are released from the substrate for subsequent lysis according to the present systems and methods. In some embodiments, at least 1 cell, at least 2 cells, at least 5 cells, at least 10 cells, at least 15 cells, at least 20 cells, at least 50 cells, at least 75 cells, at least 100 cells, at least 125 cells, at least 150 cells, at least 175 cells, at least 200 cells, at least 250 cells, at least 300 cells, at least 350 cells, at least 400 cells, at least 450 cells, at least 500 cells or more are released from the substrate during agitation.

In some embodiments, about 1 ng/µL to about 50 ng/µL, about 1 ng/µL to about 40 ng/µL, about 1 ng/µL to about 30 ng/µL, about 1 ng/µL to about 20 ng/µL, about 1 ng/µL to about 10 ng/µL, about 1 ng/µL to about 5 ng/µL, about 1 ng/µL to about 4 ng/µL, about 1 ng/4 to about 3 ng/4 or about 1 ng/µL to about 2 ng/4 of nucleic acid with a purity of about 0.55 to 2.00, about 0.6 to about 2.00, about 0.7 to about 2.00 about 0.8 to about 2.00, about 0.9 to about 2.00, about 1.0 to about 2.00 about 1.1 to about 2.00, about 1.2 to about 2.00, about 1.3 to about 2.00, about 1.4 to about 2.00, about 1.5 to about 2.00 about 1.6 to about 2.00 about 1.7 to about 2.00 about 1.8 to about 2.00 or about 1.9 to about 2.00 is employed (obtained) from a single subject with the described methods. In some embodiments, 1 ng/µL to 50 ng/4 with a purity of about 0.55 to 2.00 is employed (obtained) from a single subject with the described methods.

IV. Lysis Solutions

A variety of lysis solutions have been described and are known to those of skill in the art. Any of these well known lysis solutions can be employed with the present methods in order to isolate nucleic acids from a sample. Exemplary lysis solutions include those commercially available, such as those sold by INVITROGEN®, QIAGEN®, LIFE TECHNOLOGIES® and other manufacturers, as well as those which can be generated by one of skill in a laboratory setting. Lysis buffers have also been well described and a variety of lysis buffers can find use with the disclosed methods, including for example those described in Molecular Cloning (three volume set, Cold Spring Harbor Laboratory Press, 2012) and Current Protocols (Genetics and Genomics; Molecular Biology; 2003-2013), both of which are incorporated herein by reference for all purposes.

Cell lysis is a commonly practiced method for the recovery of nucleic acids from within cells. In many cases, the cells are contacted with a lysis solution, commonly an alkaline solution comprising a detergent, or a solution of a lysis enzyme. Such lysis solutions typically contain salts, detergents and buffering agents, as well as other agents that one of skill would understand to use. After full and/or partial lysis, the nucleic acids are recovered from the lysis solution.

In some embodiments, cells are resuspended in an aqueous buffer, with a pH in the range of from about pH 4 to about 10, about 5 to about 9, about 6 to about 8 or about 7 to about 9.

In some embodiments, the buffer salt concentration is from about 10 mM to about 200 mM, about 10 mM to about 100 mM or about 20 mM to about 80 mM.

In some embodiments, the buffer further comprises chelating agents such as ethylenediaminetetraacetic acid (EDTA) or ethylene glycol tetraacetic acid (EGTA).

In some embodiments, the lysis solution further comprises other compounds to assist with nucleic acid release from cells such as polyols, including for example but not limited to sucrose, as well as sugar alcohols such as maltitol, sorbitol, xylitol, erythritol, and/or isomalt. In some embodiments, polyols are in the range of from about 2% to about 15% w/w, or about 5% to about 15% w/w or about 5% to about 10% w/w.

In some embodiments, the lysis solutions further comprises surfactants, such as for example but not limited to Triton X-100, SDS, CTAB, X-114, CHAPS, DOC, and/or NP-40. In some embodiments such surfactants are in the range of from about 1% to about 5% w/w, about 1% to about 4% w/w, or about 1% to about 3% w/w.

In embodiments, the lysis solution further comprises chaotropes, such as for example but not limited to urea, sodium dodecyl sulfate and/or thiourea. In some embodiments, the chaotrope is used at a concentration in the range of from about 0.5 M to 8 M, about 1 M to about 6 M, about 2 M to about 6 M or about 1 M to about 3 M.

In some embodiments, the lysis solution further comprises one or more additional lysis reagents and such lysis reagents are well known in the art. In some embodiments, such lysis reagents include cell wall lytic enzymes, such as for example but not limited to lysozyme. In some embodiments, lysis reagents comprise alkaline detergent solutions, such as 0.1 aqueous sodium hydroxide containing 0.5% sodium dodecyl sulphate.

In some embodiments, the lysis solution further comprises aqueous sugar solutions, such as sucrose solution and chelating agents such as EDTA, for example the STET buffer. In certain embodiments, the lysis reagent is prepared by mixing the cell suspension with an equal volume of lysis solution having twice the desired concentration (for example 0.2 sodium hydroxide, 1.0% sodium dodecyl sulphate).

In some embodiments, after the desired extent of lysis has been achieved, the mixture comprising lysis solution and lysed cells is contacted with a neutralizing or quenching reagent to adjust the conditions such that the lysis reagent does not adversely affect the desired product. In some embodiments, the pH is adjusted to a pH of from about 5 to about 9, about 6 to about 8, about 5 to about 7, about 6 to about 7 or about 6.5 to 7.5 to minimize and/or prevent degradation of the cell contents, including for example but not limited to the nucleic acids. In some embodiments, when the lysis reagent comprises an alkaline solution, the neutralizing reagent comprises an acidic buffer, for example an alkali metal acetate/acetic acid buffer. In some embodiments, lysis conditions, such as temperature and composition of the lysis reagent are chosen such that lysis is substantially completed while minimizing degradation of the desired product, including for example but not limited to nucleic acids.

In some embodiments, a first, second, third, fourth, fifth, sixth, seventh, eighth, ninth, tenth, eleventh, twelfth, thirteenth, fourteenth, fifteenth or twentieth lysis solution is employed with the methods. In some embodiments, the volume of lysis buffer used is about 10 µL, about 20 µL, about 30 µL, about 40 µL, about 50 µL, about 60 µL, about 70 µL, about 80 µL, about 90 µL, about 100 µL, about 120 µL, about 130 µL, about 140 µL, about 150 µL, 160 µL, about 170 µL, about 180 µL, about 190 µL, about 200 µL, about 220 µL, about 230 µL, about 240 µL, about 250 µL, about 260 µL, about 270 µL, about 280 µL, about 290 µL, about 300 µL, about 320 µL, about 330 µL, about 340 µL, about 350 µL, about 360 µL, about 370 µL, about 380 µL, about 390 µL, about 400 µL, about 450 µL, about 500 µL, about 550 µL, about 600 µL, about 650 µL, about 700 µL, about 750 µL, about 800 µL, about 850 µL, 900 µL, 950 µL, 1000 µL, 1500 µL or 2000 µL. In some embodiments, the lysis buffer is between about 10 µL and about 1000 µL, about 10 µL and about 800 µL, about 10 µL and about 600 µL, about 10 µL and about 400 µL, about 20 µL and about 400 µL, about 50 µL and about 300 µL, about 50 µL and about 200 µL, about 50 µL and about 400 µL, about 100 µL and about 400 µL, about 10 µL and about 300 µL or about 100 µL and about 200 µL.

Any combination of the above can be employed by one of skill, as well as combined with other known and routine methods, and such combinations are contemplated by the present invention.

V. Purification of Nucleic Acids from Lysis Buffer

In some embodiments, the nucleic acids, including for example but not limited to genomic DNA, are isolated from lysis buffer prior to performing subsequent analysis. In some embodiments, the nucleic acids are isolated from the lysis buffer prior to the performance of additional analyses, such as for example but not limited to real-time PCR analyses. Any of a variety of methods useful in the isolation of small quantities of nucleic acids are used by various embodiments of the disclosed methods. These include but are not limited to precipitation, gel filtration, density gradients and solid phase binding. Such methods have also been described in for example, Molecular Cloning (three volume set, Cold Spring Harbor Laboratory Press, 2012) and Current Protocols (Genetics and Genomics; Molecular Biology; 2003-2013), incorporated herein by reference for all purposes.

Nucleic Acid precipitation is a well know method for isolation that is known by those of skill in the art. A variety of solid phase binding methods are also known in the art including but not limited to solid phase binding methods that make use of solid phases in the form of beads (e.g., silica, magnetic), columns, membranes or any of a variety other physical forms known in the art. In some embodiments, solid phases used in the disclosed methods reversibly bind nucleic acids. Examples of such solid phases include so-called "mixed-bed" solid phases are mixtures of at least two different solid phases, each of which has a capacity to nucleic acids under different solution conditions, and the ability and/or capacity to release the nucleic acid under different conditions; such as those described in US Patent Application No. 2002/0001812, incorporated by reference herein in its entirety for all purposes. Solid phase affinity for nucleic acids according to the disclosed methods can be through any one of a number of means typically used to bind a solute to a substrate. Examples of such means include but are not limited to, ionic interactions (e.g., anion-exchange chromatography) and hydrophobic interactions (e.g., reversed-phase chromatography), pH differentials and changes, salt differentials and changes (e.g., concentration changes, use of chaotropic salts/agents). Exemplary pH based solid phases include but are not limited to those used in the INVITROGEN ChargeSwitch Normalized Buccal Kit magnetic beads, to which bind nucleic acids at low pH (<6.5) and releases nucleic acids at high pH (>8.5) and mono-amino-N-aminoethyl (MANAE) which binds nucleic acids at a pH of less than 7.5 and release nucleic acids at a pH of greater than 8. Exemplary ion exchange based substrates include but are not limited to DEA-SEPHAROSE™, Q-SEPHAROSE™, and DEAE-SEPHADEX™ from PHARMACIA (Piscataway, N.J.), DOWEX® I from The Dow Chemical Company (Midland, Mich.), AMBERLITE® from Rohm & Haas (Philadelphia, Pa.), DUOLITE® from Duolite International, In. (Cleveland, Ohio), DIALON TI and DIALON TII.

Any individual method is contemplated for use alone or in combination with other methods, and such useful combination are well known and appreciated by those of skill in the art.

VI. Nucleic Acid Analyses

The disclosed methods are used to isolate nucleic acids, such as genomic DNA (gDNA) for a variety of nucleic acid analyses, including genomic analyses. In some embodiments, such analysis includes detection of variety of genetic mutations, which include but are not limited to one or more deletions, insertions, transitions and transversions. In some embodiments, the mutation is a single-nucleotide polymorphism (SNP).

A variety of methods for analyzing such isolated nucleic acids, for example but not limited to genomic DNA (gDNA) are known in the art and include PCR methods, such as real-time PCR analysis, microarray analysis, hybridization analysis and nucleic acid sequence analysis, as well as a variety of other methods where nucleic acid compositions are analyzed and which are known to those of skill in the art. See, for example, Molecular Cloning (three volume set, Cold Spring Harbor Laboratory Press, 2012) and Current Protocols (Genetics and Genomics; Molecular Biology; 2003-2013).

a. Real-Time PCR

For the design of Real-Time PCR assays, several parts are coordinated, including the DNA fragment that is flanked by the two primers and subsequently amplified, often referred to as the amplicon, the two primers and the detection probe or probes to be used.

Real-time PCR relies on the visual emission of fluorescent dyes conjugated to short polynucleotides (termed "detection probes") that associate with genomic alleles in a sequence-specific fashion. Real-time PCR probes differing by a single nucleotide can be differentiated in a real-time PCR assay by the conjugation and detection of probes that fluoresce at different wavelengths. Real-Time PCR finds use in detection applications (diagnostic applications), quantification applications and genotyping applications.

Several related methods for performing real-time PCR are disclosed in the art, including assays that rely on TAQMAN® probes (U.S. Pat. Nos. 5,210,015 and 5,487,972, and Lee et al., *Nucleic Acids Res.* 21:3761-6, 1993), molecular beacon probes (U.S. Pat. Nos. 5,925,517 and 6,103,476, and Tyagi and Kramer, *Nat. Biotechnol.* 14:303-8, 1996), self-probing amplicons (scorpions) (U.S. Pat. No. 6,326,145, and Whitcombe et al., *Nat. Biotechnol.* 17:804-7, 1999), Amplisensor (Chen et al., *Appl. Environ. Microbiol.* 64:4210-6, 1998), Amplifluor (U.S. Pat. No. 6,117,635, and Nazarenko et al., *Nucleic Acids Res.* 25:2516-21, 1997, displacement hybridization probes (Li et al., *Nucleic Acids Res.* 30:E5, 2002), DzyNA-PCR (Todd et al., *Clin. Chem.* 46:625-30, 2000), fluorescent restriction enzyme detection (Cairns et al., *Biochem. Biophys. Res. Commun.* 318:684-90, 2004) and adjacent hybridization probes (U.S. Pat. No. 6,174,670 and Wittwer et al., *Biotechniques* 22:130-1, 134-8, 1997).

In some instances, real-time PCR can result in detection of a variety of gene mutations, including for example but not limited to SNPs. In some embodiments, detection of SNPs in specific gene candidates is performed using real-time PCR, based on the use of intramolecular quenching of a fluorescent molecule by use of a tethered quenching moiety. Thus, according to exemplary embodiments, real-time PCR methods also include the use of molecular beacon technology. The molecular beacon technology utilizes hairpin-shaped molecules with an internally-quenched fluorophore whose fluorescence is restored by binding to a DNA target of interest (See, e.g., Kramer, R. et al. *Nat. Biotechnol.* 14:303-308, 1996). In some embodiments, increased binding of the molecular beacon probe to the accumulating PCR product is used to specifically detect SNPs present in genomic DNA.

One of the many suitable genotyping procedures is the TAQMAN® allelic discrimination assay. In some instances of this assay, an oligonucleotide probe labeled with a fluorescent reporter dye at the 5' end of the probe and a quencher dye at the 3' end of the probe is utilized. The proximity of the quencher to the intact probe maintains a low fluorescence for the reporter. During the PCR reaction, the 5' nuclease activity of DNA polymerase cleaves the probe, and separates the dye and quencher. This results in an increase in fluorescence of the reporter. Accumulation of PCR product is detected directly by monitoring the increase in fluorescence of the reporter dye. The 5' nuclease activity of DNA polymerase cleaves the probe between the reporter and the quencher only if the probe hybridizes to the target and is amplified during PCR. The probe is designed to straddle a target SNP position and hybridize to the nucleic acid molecule only if a particular SNP allele is present.

By way of example, to amplify the Avellino corneal dystrophy associated SNP located in exon 4 of the TGFβI gene, forward and reverse PCR primer pairs (SEQ ID NOs:1 to 24 in FIG. 2) were constructed as described in U.S. Patent Publication No. 2012/0077200. In some embodiments, any of the forward and reverse primer pairs disclosed therein are used in the improved methods disclosed herein. In a preferred embodiment, the forward and reverse primer pair of SEQ ID NO:1 (forward) and SEQ ID NO:2 (reverse) are used in the improved methods provided herein.

In order to detect the guanine-to-adenine mutation in exon 4 of TGFβI gene, fluorescently labeled real-time PCR probe pairs for the detection of the wild type ("G") and Avellino corneal dystrophy-associated mutant ("A") allele having nucleotide sequences according to SEQ ID NOs: 25 to 42, as shown in FIG. 3, were constructed as described in U.S. Patent Publication 2012/0077200. In some embodiments, any of the wild type and mutant probes are used in the improved methods disclosed herein. In a preferred embodiment, the wild type and mutant probe pair of SEQ ID NO:25 (wild type) and SEQ ID NO:26 (mutant) are used in the improved methods provided herein. To differentiate the wild type allele from the disease-associated allele, the wild type probes were labeled with VIC, and the mutant probes were labeled with FAM. The minor groove binder (MGB) was attached to the probe so as to facilitate binding to a complementary gene fragment.

b. Real-Time PCR Cycles

Real-time PCR methods include a variety of steps or cycles as part of the methods for amplification. These cycles include denaturing double-stranded nucleic acids, annealing a forward primer, a reverse primer and a detection probe to the target genomic DNA sequence and synthesizing (i.e., replicating) second-strand DNA from the annealed forward primer and the reverse primer. This three step process is referred to herein as a cycle.

In some embodiments, about 10, 15, 20, 25, 30, 35, 40, 45, 50, 55, or 60 cycles are employed. In some embodiments, about 10 to about 60 cycles, about 20 to about 50 or about 30 to about 40 cycles are employed. In some embodiments, 40 cycles are employed.

In some embodiments, the denaturing double-stranded nucleic acids step occurs at a temperature of about 80° C. to 100° C., about 85° C. to about 99° C., about 90° C. to about 95° C. for about 1 second to about 5 seconds, about 2 seconds to about 5 seconds, or about 3 seconds to about 4 seconds. In some embodiments, the denaturing double-stranded nucleic acids step occurs at a temperature of 95° C. for about 3 seconds.

In some embodiments, the annealing a forward primer, a reverse primer and a detection probe to the target genomic DNA sequence step occurs at about 40° C. to about 80° C., about 50° C. to about 70° C., about 55° C. to about 65° C. for about 15 seconds to about 45 seconds, about 20 seconds to about 40 seconds, about 25 seconds to about 35 seconds. In some embodiments, the annealing a forward primer, a reverse primer and a detection probe to the target genomic DNA sequence step occurs at about 60° C. for about 30 seconds.

In some embodiments, the synthesizing (i.e., replicating) second-strand DNA from the annealed forward primer and the reverse primer occurs at about 40° C. to about 80° C., about 50° C. to about 70° C., about 55° C. to about 65° C. for about 15 seconds to about 45 seconds, about 20 seconds to about 40 seconds, about 25 seconds to about 35 seconds. In some embodiments, the annealing a forward primer, a reverse primer and a detection probe to the target genomic DNA sequence step occurs at about 60° C. for about 30 seconds.

In some embodiments, it was found that about 1 μL, about 2 μL, about 3 μL, about 4 μL or about 5 μL of a genomic DNA sample prepared according to the present methods described herein, are combined with only about 0.05 μL, about 0.10 μL about 0.15 μL, about 0.20 μL, about 0.25 μL or about 0.25 μL of a 30×, 35×, 40×, 45×, 50× or 100× real-time PCR assay mix and distilled water to form the PCR master mix. In some embodiments, the PCR master mix has a final volume of about 5 μL, about 6 μL, about 7 μL, about 8 μL, about 9 μL, about 0 μL, about 11 μL, about 12 μL, about 13 μL, about 14 μL, about 15 μL, about 16 μL, about 17 μL, about 18 μL, about 19 μL or about 20 μL or more. In some embodiments, it was found that 2 μL of a genomic DNA sample prepared as described above, are combined with only about 0.15 μL of a 40× real-time PCR assay mix and 2.85 μL of distilled water in order to form the PCR master mix.

While exemplary reactions are described herein, one of skill would understand how to modify the temperatures and times based on the probe design. Moreover, the present methods contemplate any combination of the above times and temperatures.

c. PCR Primers and Primer Design

In some embodiments, primers are tested and designed in a laboratory setting. In some embodiments, primers are designed by computer based in silico methods. Primer sequences are based on the sequence of the amplicon or target nucleic acid sequence that is to be amplified. Shorter amplicons typically replicate more efficiently and lead to more efficient amplification as compared to longer amplicons.

In designing primers, one of skill would understand the need to take into account melting temperature ($T_m$; the temperature at which half of the primer-target duplex is dissociated and becomes single stranded and is an indication of duplex stability; increased $T_m$ indicates increased stability) based on GC and AT content of the primers being designed as well as secondary structure considerations (increased GC content can lead to increased secondary structure). $T_M$'s can be calculated using a variety of methods known in the art and those of skill would readily understand such various methods for calculating $T_M$; such methods include for example but are not limited to those available in online tools such as the $T_M$ calculators available on the World Wide Web at promega.com/techserv/tools/biomath/calc11.htm. Primer specificity is defined by its complete sequence in combination with the 3' end sequence, which is the portion elongated by Taq polymerase. In some embodiments, the 3' end should have at least 5 to 7 unique nucleotides not found anywhere else in the target sequence, in order to help reduce false-priming and creation of incorrect amplification products. Forward and reverse primers typically bind with similar efficiency to the target. In some instances, tools such as NCBI BLAST (located on the World Wide Web at ncbi.nlm.nih.gov) are employed to performed alignments and assist in primer design.

Those of skill in the art would be well aware of the basics regarding primer design for a target nucleic acid sequence and a variety of reference manuals and texts have extensive teachings on such methods, including for example, Molecular Cloning (three volume set, Cold Spring Harbor Laboratory Press, 2012) and Current Protocols (Genetics and Genomics; Molecular Biology; 2003-2013) and Real-Time PCR in Microbiology: From Diagnostics to Characterization (Ian M. MacKay, Calster Academic Press; 2007); PrimerAnalyser Java tool available on the World Wide Web at primerdigital.com/tools/PrimerAnalyser.html and Kalendar R, et al. (*Genomics*, 98(2): 137-144 (2011)), all of which are incorporated herein in their entireties for all purposes.

An additional aspect of primer design is primer complexity or linguistic sequence complexity (see, Kalendar R, et al. (*Genomics*, 98(2): 137-144 (2011)). Primers with greater linguistic sequence complexity (e.g., nucleotide arrangement and composition) are typically more efficient. In some embodiments, the linguistic sequence complexity calculation method is used to search for conserved regions between compared sequences for the detection of low-complexity regions including simple sequence repeats, imperfect direct or inverted repeats, polypurine and polypyrimidine triple-stranded cDNA structures, and four-stranded structures (such as G-quadruplexes). In some embodiments, linguistic complexity (LC) measurements are performed using the alphabet-capacity L-gram method (see, A. Gabrielian, A. Bolshoy, *Computer & Chemistry* 23:263-274 (1999) and Y. L. Orlov, V. N. Potapov, Complexity: an internet resource for analysis of DNA sequence complexity, *Nucleic Acids Res.* 32: W628-W633(2004)) along the whole sequence length and calculated as the sum of the observed range (xi) from 1 to L size words in the sequence divided by the sum of the expected (E) value for this sequence length. Some G-rich (and C-rich) nucleic acid sequences fold into four-stranded DNA structures that contain stacks of G-quartets (see, the World Wide Web at quadruplex.org). In some instances, these quadruplexes are formed by the intermolecular association of two or four DNA molecules, dimerization of sequences that contain two G-bases, or by the intermolecular folding of a single strand containing four blocks of guanines (see, P. S. Ho, *PNAS*, 91:9549-9553 (1994); I. A. Il'icheva, V. L. Florent'ev, *Russian Journal of Molecular Biology* 26:512-531(1992); D. Sen, W. Gilbert, *Methods Enzymol.* 211:191-199 (1992); P. A. Rachwal, K. R. Fox, *Methods* 43:291-301 (2007); S. Burge, G. N. Parkinson, P. Hazel, A. K. Todd, K. Neidle, *Nucleic Acids Res.* 34:5402-5415 (2006); A. Guédin, J. Gros, P. Alberti, J. Mergny, *Nucleic Acids Res.* 38:7858-7868 (2010); O. Stegle, L. Payet, J. L. Mergny, D. J. MacKay, J. H. Leon, *Bioinformatics* 25:i374-i382 (2009); in some instances, these are eliminated from primer design because of their low linguistic complexity, LC=32% for $(TTAGGG)_4$.

These methods include various bioinformatics tools for pattern analysis in sequences having GC skew, (G−C)/(G+C), AT skew, (A−T)/(A+T), CG-AT skew, (S−W)/(S+W), or purine-pyrimidine (R−Y)/(R+Y) skew regarding CG content and melting temperature and provide tools for determining linguistic sequence complexity profiles. For example the GC skew in a sliding window of n, where n is a positive integer, bases is calculated with a step of one base, according to the formula, (G−C)/(G+C), in which G is the total number of guanines and C is the total number of cytosines for all sequences in the windows (Y. Benita, et al., *Nucleic Acids Res.* 31:e99 (2003)). Positive GC-skew values indicated an overabundance of G bases, whereas negative GC-skew values represented an overabundance of C bases. Similarly, other skews are calculated in the sequence. Such methods, as well as others, are employed to determine primer complexity in some embodiments.

According to non-limiting example embodiments, real-time PCR is performed using exonuclease primers (TAQMAN® probes). In such embodiments, the primers utilize the 5' exonuclease activity of thermostable polymerases such as Taq to cleave dual-labeled probes present in the amplification reaction (See, e.g., Wittwer, C. et al. Biotechniques 22:130-138, 1997). While complementary to the PCR product, the primer probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal. Non-limiting examples of fluorescent probes include the 6-carboxy-flourescein moiety and the like. Exemplary quenchers include Black Hole Quencher 1 moiety and the like.

A variety of PCR primers can find use with the disclosed methods. Exemplary primers include but are not limited to those described herein. Primers for use in the disclosed methods are also found in U.S. Patent Publication No. 20120077200, which is hereby incorporated by reference for all purposes. In some embodiments, the PCR primers for use in the methods of the present disclosure include but are not limited to the following listed in Table 1 and find use in the detection of the TGFβI gene. Tables 2 and 3 provide biophysical parameters for each primer, as calculated using the World Wide Web at primerdigital.com/tools/PrimerAnalyser.html.

TABLE 1

Exemplary Primers for the TGFβI gene

| Primer Name | SEQ ID NO: | Primer Sequence |
|---|---|---|
| ACD Fw primer | SEQ ID NO: 1 | 5'-TCC ACC ACC ACT CAG CTG TA |
| ACD Re primer | SEQ ID NO: 2 | 5'-CCA TCT CAG GCC TCA GCT T (60 bp) |
| AV Fw primer | SEQ ID NO: 3 | 5'-TGC AGC CCT ACC ACT CTC AA |
| AV Re primer | SEQ ID NO: 4 | 5'-AGG CCT CGT TGC TAG G (150 bp) |
| Real Fw primer | SEQ ID NO: 5 | 5'-TAG TCT CTT ATT CTA ATA GA |
| Real Re primer | SEQ ID NO: 6 | 5'-GCT GCA GAC TCT GTG TTT AA (860 bp) |
| ACD Fw2 primer | SEQ ID NO: 7 | 5'-CCA TCC CTC CTT CTG TCT TCT G |
| ACD Re2 primer | SEQ ID NO: 8 | 5'-CGG GCC CCT CCA TCT C (140 bp) |
| ACD Fw3 primer | SEQ ID NO: 9 | 5'-CAG AGA AGG GAG GGT GTG GTT |
| ACD Re3 primer | SEQ ID NO: 10 | 5'-GGG CGA AGA TGG TGA AGC T (190 bp) |

TABLE 1-continued

Exemplary Primers for the TGFβI gene

| Primer Name | SEQ ID NO: | Primer Sequence |
|---|---|---|
| ACD Fw4 primer | SEQ ID NO: 11 | 5'-TCC TCG TCC TCT CCA CCT GTA |
| ACD Re4 primer | SEQ ID NO: 12 | 5'-AGC TGG CAA GGA GGC CC |
| ACD Fw5 primer | SEQ ID NO: 13 | 5'-TTT GGG CTT TCC CAC ATG C |
| ACD Re5 primer | SEQ ID NO: 14 | 5'-GGC AGA CGG AGG TCA TCT CA |
| ACD Fw6 primer | SEQ ID NO: 15 | 5'-GTA GTA CCG TGC TCT CTG |
| ACD Re6 primer | SEQ ID NO: 16 | 5'-AGT TCC CCA TAA GAA TCC CCC |
| ACD Fw7 primer | SEQ ID NO: 17 | 5'-GGC TGG ACC CCC AGA GG |
| ACD Re7 primer | SEQ ID NO: 18 | 5'-ACC CCT CGG GGA AGT AAG G |
| ACD Fw8 primer | SEQ ID NO: 19 | 5'-AAC CTT TAC GAG ACC CTG GGA |
| ACD Re8 primer | SEQ ID NO: 20 | 5'-GAC TCC CAT CCA TCA TGC CC |
| ACD Fw9 primer | SEQ ID NO: 21 | 5'-AGT CGT TGG ATC CAC CAC CA |
| ACD Re9 primer | SEQ ID NO: 22 | 5'-GAC GTC ATT TCC TAC TGT TTC AGG |
| ACD Fw10 primer | SEQ ID NO: 23 | 5'-CCC CCC AGA AAC AGC CTG |
| ACD Re10 primer | SEQ ID NO: 24 | 5'-TTC TAA GGG GTT AAG GAG AAA GCT T |
| GCD1 Fw primer | SEQ ID NO: 43 | 5'-ACA CAG TCT TTG CTC CCA CAA A |
| GCD1 Re primer | SEQ ID NO: 44 | 5'-ACT TAA GTT GGT CTT TAC CCA AGA GTC T |

TABLE 2

Biophysical Parameters for Forward Primers

| Forward Primer | Length | Tm1 | Tm2 | GC Content | % Complexity | PCR Effic. |
|---|---|---|---|---|---|---|
| SEQ ID NO: 1 | 19 | 55.4 | 57.8 | 57.9 | 70 | 70 |
| SEQ ID NO: 3 | 20 | 57.1 | 58 | 55 | 81 | 66 |
| SEQ ID NO: 5 | 20 | 40.2 | 45.7 | 25 | 73 | 38 |
| SEQ ID NO: 7 | 22 | 55.9 | 60.2 | 54.5 | 62 | 43 |
| SEQ ID NO: 9 | 21 | 57.5 | 60.2 | 57.1 | 64 | 40 |
| SEQ ID NO: 11 | 21 | 57.6 | 60.2 | 57.1 | 66 | 57 |
| SEQ ID NO: 13 | 19 | 55.4 | 55.7 | 52.6 | 81 | 80 |
| SEQ ID NO: 15 | 18 | 50.6 | 55.3 | 55.6 | 75 | 66 |
| SEQ ID NO: 17 | 17 | 57.8 | 62.2 | 76.5 | 74 | 60 |
| SEQ ID NO: 19 | 21 | 56.6 | 58.2 | 52.4 | 82 | 73 |
| SEQ ID NO: 21 | 20 | 57.4 | 58 | 55 | 78 | 46 |
| SEQ ID NO: 23 | 18 | 56.5 | 59.9 | 66.7 | 69 | 69 |
| Avg | 19.67 | 54.96 | 57.80 | 56.05 | 72.69 | 59.85 |
| Median | 20 | 56.55 | 58.1 | 55.3 | 73.5 | 63 |
| Std Dev | 1.50 | 5.00 | 4.24 | 11.78 | 6.84 | 14.10 |

TABLE 3

Biophysical Parameters for Reverse Primers

| Reverse Primer | Length | Tm1 | Tm2 | GC Content | % Complexity | PCR Effic. |
|---|---|---|---|---|---|---|
| SEQ ID NO: 2 | 19 | 55.5 | 57.8 | 57.9 | 72 | 52 |
| SEQ ID NO: 4 | 16 | 52.1 | 54.5 | 62.5 | 78 | 78 |
| SEQ ID NO: 6 | 20 | 52.4 | 53.9 | 45 | 84 | 41 |
| SEQ ID NO: 8 | 16 | 55.2 | 59.6 | 75 | 63 | 53 |
| SEQ ID NO: 10 | 19 | 56.5 | 57.8 | 57.9 | 78 | 69 |
| SEQ ID NO: 12 | 17 | 58.5 | 59.8 | 70.6 | 74 | 66 |
| SEQ ID NO: 14 | 20 | 57.6 | 60.1 | 60 | 84 | 74 |
| SEQ ID NO: 16 | 21 | 54.9 | 58.2 | 52.4 | 71 | 51 |
| SEQ ID NO: 18 | 19 | 56.6 | 60 | 63.2 | 78 | 60 |
| SEQ ID NO: 20 | 20 | 56.5 | 60.1 | 60 | 65 | 65 |
| SEQ ID NO: 22 | 24 | 55.5 | 58.7 | 45.8 | 88 | 67 |
| SEQ ID NO: 24 | 25 | 55.3 | 57.2 | 40 | 74 | 40 |
| Avg | 19.69 | 55.61 | 58.13 | 57.33 | 76.54 | 60.69 |
| Median | 19.5 | 55.5 | 58.45 | 58.95 | 76 | 62.5 |
| Std Dev | 2.77 | 1.86 | 2.10 | 10.33 | 7.52 | 12.30 |

In some embodiments, the real-time PCR primers for use with the disclosed methods have a linguistic sequence complexity of at least 70%, at least 72%, at least 75%, at least 77%, at least 80%, at least 82%, at least 85%, at least 88%, at least 90%, at least 92%, at least 95%, at least 97% or at least 99%.

d. Detection Probe Design and Detection Probes

A variety of detection probes can find use with the disclosed methods and are employed for genotyping and or for quantification. Detection probes commonly employed by those of skill in the art include but are not limited to hydrolysis probes (also known as TAQMAN® probes, 5' nuclease probes or dual-labeled probes), hybridization probes, and Scorpion primers (which combine primer and detection probe in one molecule). In some embodiments, detection probe design is determined by one of skill in the art based on the desired probe target such that the probe is compatible with the PCR primers employed (e.g., primers and probes should not interfere with one another's functions in the real-time PCR assay). In some embodiments, probes are designed to have higher $T_m$'s than the primers in order to promote efficient signal production. $T_m$'s are calculated using any of a variety of methods known in the art and those of skill would readily understand such various methods for calculating Tm; such methods include for example those available in online tools such as the calculators available on the World Wide Web at promega.com/techserv/tools/biomath/calc11.htm. In some embodiments, the increased Tm of the detection probe provides that the detection probe has bound before the primers are elongated by the polymerase.

In some embodiments, detection probes contain various modifications. In some embodiments, detection probes include modified nucleic acid residues, such as but not limited to 2'-O-methyl ribonucleotide modifications, phosphorothioate backbone modifications, phosphorodithioate backbone modifications, phosphoramidate backbone modifications, methylphosphonate backbone modifications, 3' terminal phosphate modifications and/or 3' alkyl substitutions.

In some embodiments, the detection probe has increased affinity for a target sequence due to modifications. Such detection probes include detection probes with increased length, as well as detection probes containing chemical modifications. Such modifications include but are not limited to 2'-fluoro (2'-deoxy-2'-fluoro-nucleosides) modifications, LNAs (locked nucleic acids), PNAs (peptide nucleic acids), ZNAs (zip nucleic acids), morpholinos, methylphosphonates, phosphoramidates, polycationic conjugates and 2'-pyrene modifications. In some embodiments, the detector probes contains one or more modifications including 2' fluoro modifications (aka, 2'-Deoxy-2'-fluoro-nucleosides), LNAs (locked nucleic acids), PNAs (peptide nucleic acids), ZNAs (zip nucleic acids), morpholinos, methylphosphonates, phosphoramidates, and/or polycationic conjugates.

In some embodiments, the detection probes contain detectable moieties, such as those described herein as well as any detectable moieties known to those of skill in the art. Such detectable moieties include for example but are not limited to fluorescent labels and chemiluminescent labels. Examples of such detectable moieties can also include members of FRET pairs. In some embodiments, the detection probe contains a detectable entity.

Examples of fluorescent labels include but are not limited to AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); 6-FAM (6-Carboxyfluorescein; aka FAM; including TAQMAN® FAM™); TAQMAN VIC®; 5(6)-FAM cadaverine; 5-FAM cadaverine; 5(6)-FAM ethylenediamme; 5-FAM ethylenediamme; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4',5'-dichloro-2',7'-dimethoxyfluorescein); 5-CR1 1O (5-Carboxyrhodamine 110); 6-CR1 1O (6-Carboxyrhodamine 110); 5-CR6G (5-Carboxyrhodamine 6G); 6-CR6G (6-Carboxyrhodamine 6G); 5(6)-Caroxyrhodamine 6G cadaverine; 5(6)-Caroxyrhodamine 6G ethylenediamme; 5-ROX (5-Carboxy-X-rhodamine); 6-ROX (6-Carboxy-X-rhodamine); 5-TAMRA (5-Carboxytetramethylrhodamine); 6-TAMRA (6-Carboxytetramethylrhodamine); 5-TAMRA cadaverine; 6-TAMRA cadaverine; 5-TAMRA ethylenediamme; 6-TAMRA ethylenediamme; 5-TMR C6 maleimide; 6-TMR C6 maleimide; TR C2 maleimide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof.

Examples of chemiluminescent labels include but are not limited to those labels used with Southern Blot and Western Blot protocols (see, for e.g., Sambrook and Russell, Molecular Cloning: A Laboratory Manual, (3rd ed.) (2001); incorporated by reference herein in its entirety). Examples include but are not limited to -(2'-spiroadamantane)-4-methoxy-4-(3"-phosphoryloxy)phenyl-1,2-dioxetane (AMPPD); acridinium esters and adamantyl-stabilized 1,2-dioxetanes, and derivatives thereof.

The labeling of probes is known in the art. The labeled probes are used to hybridize within the amplified region during amplification. The probes are modified so as to avoid them from acting as primers for amplification. The detection probe is labeled with two fluorescent dyes, one capable of quenching the fluorescence of the other dye. One dye is attached to the 5' terminus of the probe and the other is attached to an internal site, so that quenching occurs when the probe is in a non-hybridized state.

Typically, real-time PCR probes consist of a pair of dyes (a reporter dye and an acceptor dye) that are involved in fluorescence resonance energy transfer (FRET), whereby the acceptor dye quenches the emission of the reporter dye. In general, the fluorescence-labeled probes increase the specificity of amplicon quantification.

Real-time PCR that are used in some embodiments of the disclosed methods also include the use of one or more hybridization probes (i.e., detection probes), as determined by those skilled in the art, in view of this disclosure. By way of non-limiting example, such hybridization probes include but are not limited to one or more of those provided in the described methods. Exemplary probes, such as the HEX channel and/or FAM channel probes, are understood by one skilled in the art.

According to example embodiments, detection probes and primers are conveniently selected e.g., using an in silico analysis using primer design software and cross-referencing against the available nucleotide database of genes and genomes deposited at the National Center for Biotechnology Information (NCBI). Some additional guidelines may be used for selection of primers and/or probes in some embodiments. For example, in some embodiments, the primers and probes are selected such that they are close together, but not overlapping. In some embodiments, the primers may have the same (or close $T_M$) (e.g., between about 58° C. and about 60° C.). In some embodiments, the $T_M$ of the probe is approximately 10° C. higher than that selected for the $T_M$ of the primers. In some embodiments, the length of the probes and primers is selected to be between about 17 and 39 base pairs, etc. These and other guidelines are used in some instances by those skilled in the art in selecting appropriate primers and/or probes.

Probes for use in the methods of the present invention include but are not limited to the following exemplary probes listed in Table 4.

TABLE 4

Exemplary Probes for the TGFβI gene

| Probe Name | SEQ ID NO: | Probe Sequence |
|---|---|---|
| Normal probe 1 | SEQ ID NO: 25 | VIC-CAC GGA CCG CAC GGA-NFQ (15 bp) |
| Mutant probe 1 | SEQ ID NO: 26 | FAM-CAC GGA CCA CAC GGA-NFQ |
| Normal probe 2 | SEQ ID NO: 27 | VIC-ACA CGG ACC GCA CG-NFQ |
| Mutant probe 2 | SEQ ID NO: 28 | FAM-ACA CGG ACC ACA CG-NFQ (14 bp) |
| Normal probe 3 | SEQ ID NO: 29 | VIC-TAC ACG GAC CGC A-NFQ |
| Mutant probe 3 | SEQ ID NO: 30 | FAM-TAC ACG GAC CAC A-NFQ (13 bp) |
| Normal probe 4 | SEQ ID NO: 31 | VIC-CTG TAC ACG GAC CGC ACG-NFQ |
| Mutant probe 4 | SEQ ID NO: 32 | FAM-CTG TAC ACG GAC CAC ACG-NFQ (18 bp) |
| Normal probe 5 | SEQ ID NO: 33 | VIC-CTG TAC ACG GAC CGC ACG GAG-NFQ |
| Mutant probe 5 | SEQ ID NO: 34 | FAM-CTG TAC ACG GAC CAC ACG GAG-NFQ (21 bp) |
| Normal probe 6 | SEQ ID NO: 35 | VIC-GCT GTA CAC GGA CCG CAC GGA GAA-NFQ |

TABLE 4-continued

Exemplary Probes for the TGFβI gene

| Probe Name | SEQ ID NO: | Probe Sequence |
|---|---|---|
| Mutant probe 6 | SEQ ID NO: 36 | FAM-GCT GTA CAC GGA CCA CAC GGA GM-NFQ |
| Normal probe 7 | SEQ ID NO: 37 | VIC-ACC GCA CGG AGA AGC-NFQ |
| Mutant probe 7 | SEQ ID NO: 38 | FAM-ACC ACA CGG AGA AGC-NFQ |
| Normal probe 8 | SEQ ID NO: 39 | VIC-ACC GCA CGG AGA AGC TGA GGC-NFQ |
| Mutant probe 8 | SEQ ID NO: 40 | FAM-ACC ACA CGG AGA AGC TGA GGC-NFQ |
| Normal probe 9 | SEQ ID NO: 41 | VIC-ACC GCA CGG AGA AGC TGA GGC CTG-NFQ |
| Mutant probe 9 | SEQ ID NO: 42 | FAM-ACC ACA CGG AGA AGC TGA GGC CTG-NFQ |
| Normal Probe 10 | SEQ ID NO: 45 | VIC-CAC CAA GAG AAC GGA-NFQ |
| Mutant Probe 10 | SEQ ID NO: 46 | FAM-CAC CAA GAG AAT GG-NFQ |
| Normal Probe 10a | SEQ ID NO: 47 | VIC-CAC CAA GAG AAC GGA G-MGB NFQ |
| #TGFBI R124C | SEQ ID NO: 48 | FAM-CAC GGA CTG CAC GGA-MGB NFQ |
| #TGFBI R124L | SEQ ID NO: 49 | FAM-CAC GGA CCT CAC GGA-MGB NFQ |
| #TGFBI R555Q-1 | SEQ ID NO: 50 | FAM-AC CAA GAG AACA GA G--MGB NFQ |

VII. Diagnostic Tests

In some embodiments, diagnostic testing is employed to determine one or more genetic conditions by detection of any of a variety of mutations. In some embodiments, diagnostic testing is used to confirm a diagnosis when a particular condition is suspected based on for example physical manifestations, signs and/or symptoms as well as family history information. In some embodiments, the results of a diagnostic test assist those of skill in the medical arts in determining an appropriate treatment regimen for a given patient and allow for more personalized and more effective treatment regimens. In some embodiments, a treatment regimen include any of a variety of pharmaceutical treatments, surgical treatments, lifestyles changes or a combination thereof as determined by one of skill in the art.

The nucleic acids obtained by the disclosed methods are useful in a variety of diagnostic tests, including tests for detecting mutations such as deletions, insertions, transversions and transitions. In some embodiments, such diagnostics are useful for identifying unaffected individuals who carry one copy of a gene for a disease that requires two copies for the disease to be expressed, identifying unaffected individuals who carry one copy of a gene for a disease in which the information could find use in developing a treatment regimen, preimplantation genetic diagnosis, prenatal diagnostic testing, newborn screening, genealogical DNA test (for genetic genealogy purposes), presymptomatic testing for predicting adult-onset disorders such as Huntington's disease, presymptomatic testing for estimating the risk of developing adult-onset cancers and Alzheimer's disease, conformational diagnosis of a symptomatic individual, and/or forensic/identity testing. In some embodiments, the present methods find use in the detection of corneal dystrophy. In some embodiments, corneal dystrophy is detected for example through detection of Avellino corneal dystrophy-related SNPs, such as those that result in R124 mutations in the TGFβI gene (including for example but not limited to an R124H mutation caused by a G to A transition at nucleotide 418 of TGFβI gene also referred to as a C(G/A)C SNP). In some embodiments, corneal dystrophy is detected for example through detection of granular corneal dystrophy-related SNPs, such as those that result in R555 mutations in the TGFβI gene (including for example but not limited to an R555W mutation caused by a C to T transition at nucleotide 1663 of TGFβI gene also referred to as a (C/T)GG SNP). In some embodiments, corneal dystrophy is detected for example through detection of lattice dystrophy-related SNPs, such as those that result in R124 and/or 626 mutations in the TGFβI gene (including for example but not limited to an R124C mutation caused by a C to T transition at nucleotide 417 of TGFβI gene also referred to as a (C/T)GC SNP or a H626P mutation caused by an A to C transition at nucleotide 1924 of TGFβI gene. In some embodiments, corneal dystrophy is detected for example through detection of Reis-Buckler corneal dystrophy-related SNPs, such as those that result in R124 mutations in the TGFβI gene (including for example but not limited to an R124L mutation caused by a G to T transition at nucleotide 418 of TGFβI gene also referred to as a C(G/T)C SNP). In some embodiments, corneal dystrophy is detected for example through detection of Thiel-Behnke corneal dystrophy-related SNPs, such as those that result in R555 mutations in the TGFβI gene (including for example but not limited to an R555Q mutation caused by a G to A transition at nucleotide 1664 of TGFβI gene also referred to as a C(G/A)G SNP).

In some embodiments, newborn screening includes any genetic screening employed just after birth in order to identify genetic disorders. In some embodiments, newborn screening finds use in the identification of genetic disorders so that a treatment regimen is determined early in life. Such tests include but are not limited to testing infants for phenylketonuria and congenital hypothyroidism.

In some embodiments, carrier testing is employed to identify people who carry a single copy of a gene mutation. In some cases, when present in two copies, the mutation can cause a genetic disorder. In some cases, one copy is sufficient to cause a genetic disorder. In some cases, the presence of two copies is contra-indicated for a particular treatment regimen, such as the presence of the Avellino mutation and pre-screening prior to performing surgical procedures in order to ensure the appropriate treatment regiment is pursued for a given patient. In some embodiments, such information is also useful for individual contemplating procreation and assists individuals with making informed decisions as well as assisting those skilled in the medical arts in providing important advice to individual patients as well as patients' relatives.

In some embodiments, predictive and/or presymptomatic types of testing are used to detect gene mutations associated with a variety of disorders. In some cases, these tests are helpful to people who have a family member with a genetic disorder, but who may exhibit no features of the disorder at the time of testing. In some embodiments, predictive testing identifies mutations that increase a person's chances of developing disorders with a genetic basis, including for example but not limited to certain types of cancer. In some embodiments, presymptomatic testing is useful in determining whether a person will develop a genetic disorder, before any physical signs or symptoms appear. The results of predictive and presymptomatic testing provides information about a person's risk of developing a specific disorder and help with making decisions about an appropriate medical treatment regimen for a patient as well as for a patient's relatives. Predictive testing is also employed, in some embodiments, to detect mutations which are contra-indicated with certain treatment regimens, such as the presence of the Avellino mutation being contra-indicated with performing LASIK surgery and/or other refractive procedures, such as but not limited to Phototherapeutic keratectomy (PTK) and/or Photorefractive keratectomy (PRK). For example, patients exhibiting the Avellino mutation should not undergo LASIK surgery or other refractive procedures.

In some embodiments, diagnostic testing also includes pharmacogenomics which includes genetic testing that determines the influence of genetic variation on drug response. Information from such pharmacogenomic analyses finds use in determining and developing an appropriate treatment regimen. Those of skill in the medical arts employ information regarding the presence and/or absence of a genetic variation in designing appropriate treatment regimen.

In some embodiments, diseases whose genetic profiles are determined using the methods of the present disclosure include but are not limited to ophthalmic disorders, cancer, diabetes mellitus, hypertension, schizophrenia, and most common congenital malformations, such as cleft lip, cleft palate, neural tube defects, Achondroplasia, Alpha-1 Antitrypsin Deficiency, Antiphospholipid Syndrome, Autism, Autosomal Dominant Polycystic Kidney Disease, Charcot-Marie-Tooth, Colon cancer, Cri du chat, Crohn's Disease, Cystic fibrosis, Dercum Disease, Down Syndrome, Duane Syndrome, Duchenne Muscular Dystrophy, Factor V Leiden Thrombophilia, Familial Hypercholesterolemia, Familial Mediterranean Fever, Fragile X Syndrome, Gaucher Disease, Hemochromatosis, Hemophilia, Holoprosencephaly, Huntington's disease, Klinefelter syndrome, Marfan syndrome, Myotonic Dystrophy, Neurofibromatosis, Noonan Syndrome, Osteogenesis imperfecta, Parkinson's disease, Phenylketonuria, Poland Anomaly, Porphyria, Progeria, Retinitis Pigmentosa, Severe Combined Immunodeficiency (SCID), Sickle cell disease, Spinal Muscular Atrophy, Tay-Sachs, Thalassemia, Trimethylaminuria, Turner Syndrome, Velocardiofacial Syndrome, WAGR Syndrome, Wilson Disease, as well as any other disease with a genetic component. Opthalmic disorders and/or disorders that include an ophthalmic component include but are not limited to chalazion, stye, trichiasis, entropion, ectropion, lagophthalmos, bleharitis, dacryocystitis, orbital cellulitis, ptergium, pterygiumcorneal dystrophy, conjuctivitis, ophthalmia neonatorum, bacterial corneal ulcer, fungal corneal ulcer, glaucoma, Fuchs Dystrophy, keratoconus, Advanced Macular Degeneration, Retinitis pigmentosa, cataracts, retinal disorecers, macular degeneration, diabetic eye problems (for example, diabetic retinopathy), blepharophimosis-ptosis-epicanthus-inversus syndrome (BPES), oculocutaneous albinism, Marfan syndrome, Stickler syndrome, and CHARGE (coloboma, heart anomalies, atresia of the choanae, retardation of growth and development, genital/urinary anomalies, ear abnormalities or deafness) syndrome. Corneal dystrophies include but are not limited to Avellino corneal dystrophy, granular corneal dystrophy, lattice type I corneal dystrophy, Fuchs Dystrophy, Thiel-Behnke and Reis-bucklers corneal dystrophy. Cancers include but are not limited to carcinoma, sarcoma, blastoma, lymphoma, leukemia germ cell tumors, and cancers of unknown origin. In some embodiments, the cancer include but is not limited to head and neck, skin, colon, oral, glioblastoma, breast, laryngeal, esophageal, endothelial, endometrial, ovarian, lung, urogenital, rectal, prostate, kidney, melanoma, renal, pancreatic, gastrointestinal, blood, liver, uterine and brain as well as viral induced cancers such as papilloma virus-induced cancer.

In some embodiments, the present methods find use in development of personalized medicine treatment regimens by providing the genomic DNA which is used in determining the genetic profile for an individual. In some embodiments, such genetic profile information is employed by those skilled in the art in order determine and/or develop a treatment regimen. In some embodiments, the presence and/or absence of various genetic variations and mutations identified in nucleic acids isolated by the described methods are used by those of skill in the art as part of a personalized medicine treatment regimen or plan. For example, in some embodiments, information obtained using the disclosed methods is compared to databases or other established information in order to determine a diagnosis for a specified disease and or determine a treatment regimen. In some cases, the information regarding the presence or absence of a genetic mutation in a particular patient is compared to a database or other standard source of information in order to make a determination regarding a proposed treatment regimen. In some cases, the presence of a genetic mutation indicates pursuing a particular treatment regimen. In some cases the absence of a genetic mutation indicates not pursuing a particular treatment regimen.

In some embodiments, information regarding the presence and/or absence of a particular genetic mutation is used to determine the treatment efficacy of treatment with the therapeutic entity, as well as to tailor treatment regimens for treatment with therapeutic entity. In some embodiments, information regarding the presence and/or absence of a genetic mutation is employed to determine whether to pursue a treatment regimen. In some embodiments, information regarding the presence and/or absence of a genetic mutation is employed to determine whether to continue a treatment regimen. In some embodiments, the presence and/or absence of a genetic mutation is employed to determine whether to discontinue a treatment regimen. In other embodiments, the presence and/or absence of a genetic mutation is employed to determine whether to modify a treatment regimen. In some embodiments the presence and/or absence of a genetic mutation is used to determine whether to increase or decrease the dosage of a treatment that is being administered as part of a treatment regimen. In other embodiments, the presence and/or absence of a genetic mutation is used to determine whether to change the dosing frequency of a treatment administered as part of a treatment regimen. In some embodiments, the presence and/or absence of a genetic mutation is used to determine whether to change the number of dosages per day, per week, times per day of a treatment. In some embodiments the presence and/or absence of a genetic mutation is used to determine whether to change the dosage amount of a treatment. In some embodiments, the presence and/or absence of a genetic mutation is determined prior to initiating a treatment regiment and/or after a treatment regimen has begun. In some embodiments, the presence and/or absence of a genetic mutation is determined and compared to predetermined standard information regarding the presence or absence of a genetic mutation.

In some embodiments, a composite of the presence and/or absence of more than one genetic mutation is generated using the disclosed methods and such composite includes any collection of information regarding the presence and/or absence of more than one genetic mutation. In some embodiments, the presence or absence of 2 or more, 3 or more, 4 or more, 5 or more, 6 or more, 7 or more, 8 or more, 9 or more, 10 or more, 20 or more, 30 or more or 40 or more genetic mutations is examined and used for generation of a composite. Exemplary information in some embodiments includes nucleic acid or protein information, or a combination of information regarding both nucleic acid and/or protein genetic mutations. Generally, the composite includes information regarding the presence and/or absence of a genetic mutation. In some embodiments, these composites are used for comparison with predetermined standard information in order to pursue, maintain or discontinue a treatment regimen.

In some embodiments, corneal dystrophy is detected for example through detection of 2, 3, 4 or 5 SNPs selected from but not limited to Avellino corneal dystrophy-related SNPs, granular corneal dystrophy-related SNPs, lattice dystrophy-related SNPs, Reis-Buckler corneal dystrophy-related SNPs, and/or Thiel-Behnke corneal dystrophy-related SNPs. In some embodiments, corneal dystrophy is detected for example through detection of an Avellino corneal dystrophy-related SNP, in combination with a granular corneal dystrophy-related SNP, a lattice dystrophy-related SNP, a Reis-Buckler corneal dystrophy-related SNP, and/or a Thiel-Behnke corneal dystrophy-related SNP. In some embodiments, corneal dystrophy is detected for example through detection of a granular corneal dystrophy-related SNP in combination with an Avellino corneal dystrophy-related SNP, a lattice dystrophy-related SNPs, a Reis-Buckler corneal dystrophy-related SNPs, and/or a Thiel-Behnke corneal dystrophy-related SNP. In some embodiments, corneal dystrophy is detected for example through detection of a lattice dystrophy-related SNP in combination with an Avellino corneal dystrophy-related SNP, a granular corneal dystrophy-related SNP, a Reis-Buckler corneal dystrophy-related SNP, and/or a Thiel-Behnke corneal dystrophy-related SNP. In some embodiments, corneal dystrophy is detected for example through detection of a Reis-Buckler corneal dystrophy-related SNP in combination with an Avellino corneal dystrophy-related SNP, a granular corneal dystrophy-related SNP, a lattice dystrophy-related SNP, and/or a Thiel-Behnke corneal dystrophy-related SNP. In some embodiments, corneal dystrophy is detected for example through detection of a Thiel-Behnke corneal dystrophy-related SNP in combination with an Avellino corneal dystrophy-related SNP, a granular corneal dystrophy-related SNP, a lattice dystrophy-related SNP and/or a Reis-Buckler corneal dystrophy-related SNP.

In some embodiments, corneal dystrophy is detected for example through detection of 2, 3, 4, 5 and/or 6 SNPs selected from Avellino corneal dystrophy-related SNPs. In some embodiments, the SNPs include SNPs that result in mutations at positions 124, 555 and/or 626 of the polypeptide encoded by the human TGFβI gene. These mutations include those that result in R124 mutations in the TGFβI gene (including for example but not limited to an R124H mutation caused by a G to A transition at nucleotide 418 of TGFβI gene also referred to as a C(G/A)C SNP), granular corneal dystrophy-related SNPs, such as those that result in R555 mutations in the TGFβI gene (including for example but not limited to an R555W mutation caused by a C to T transition at nucleotide 1663 of the TGFβI gene also referred to as a (C/T)GG SNP), lattice dystrophy-related SNPs, such as those that result in R124 mutations in the TGFβI gene (including for example but not limited to an R124C mutation caused by a C to T transition at nucleotide 417 of TGFβI gene also referred to as a (C/T)GC SNP), Reis-Buckler corneal dystrophy-related SNPs, such as those that result in R124 mutations in the TGFβI gene (including for example but not limited to an R124L mutation caused by a G to T transition at nucleotide 418 of TGFβI gene also referred to as a C(G/T)C SNP) and/or Thiel-Behnke corneal dystrophy-related SNPs, such as those that result in R555 mutations in the TGFβI gene (including for example but not limited to an R555Q mutation caused by a G to A transition at nucleotide 1664 of TGFβI gene also referred to as a C(G/A)G SNP). In some embodiments, corneal dystrophy is detected for example through detection of Avellino corneal dystrophy-related SNPs, such as those that result in R124 mutations in the TGFβI gene (including for example but not limited to an R124H mutation caused by a G to A transition at nucleotide 418 of TGFβI gene also referred to as a C(G/A)C SNP) in combination with a granular corneal dystrophy-related SNPs, such as those that result in R555 mutations in the TGFβI gene (including for example but not limited to an R555W mutation caused by a C to T transition at nucleotide 1663 of TGFβI gene also referred to as a (C/T)GG SNP). In some embodiments, corneal dystrophy is detected for example through detection of Avellino corneal dystrophy-related SNPs, such as those that result in H626P mutations in the TGFβI gene (including for example but not limited to an H626P mutation caused by an A to C transition at nucleotide 1924 of TGFβI gene).

In some embodiments, corneal dystrophy is detected for example through detection of 2, 3, 4, 5 and/or 6 of R124C, R124H, R124L, R555W, R555Q and/or H626P. In some embodiments, corneal dystrophy is detected for example through detection of 2, 3, 4 and/or 5 of R124C, R124H, R124L, R555W, and/or R555Q. In some embodiments, corneal dystrophy is detected for example through detection of R124C in combination with one or more of R124H, R124L, R555W and/or R555Q. In some embodiments, corneal dystrophy is detected for example through detection of R124H in combination with one or more of R124C, R124L, R555W and/or R555Q. In some embodiments, corneal dystrophy is detected for example through detection of R555W in combination with one or more of R124C, R124H, R124L and/or R555Q. In some embodiments, corneal dystrophy is detected for example through detection of R555Q in combination with one or more of R124C, R124H, R124L and/or R555W. In some embodiments, R124H is detected in combination with R555W. In some embodiments, corneal dystrophy is detected for example through detection of H262P in combination with one or more of R124C, R124H, R124L, R555W and/or R555Q. In some embodiments, R124C, R124H, R124L, R555W and/or R555Q are all detected. In some embodiments, R124C, R124H, R124L, R555W, R555Q and/or H626P are all detected.

VIII. Diagnostic Kits

In some embodiments, any or all of the reagents described above are packaged into a diagnostic kit. Such kits include any and/or all of the primers, probes, buffers and/or other reagents described herein in any combination. In some embodiments, the kit includes reagents for detection of 2, 3, 4, 5 and/or 6 of R124C, R124H, R124L, R555W, R555Q and/or H626P. In some embodiments, the kit includes reagents for detection of 2, 3, 4, and/or 5 of R124C, R124H, R124L, R555W and R555Q. In some embodiments, the kit includes reagents for detection of R124C, R124H, and R124L. In some embodiments, the kit includes reagents for detection of R555W and R555Q. In some embodiments, the kit includes reagents for detection of R124C. In some embodiments, the kit includes reagents for detection of R124H. In some embodiments, the kit includes reagents for detection of R124L. In some embodiments, the kit includes reagents for detection of R555W. In some embodiments, the kit includes reagents for detection of R555Q.

In some embodiments, the kit includes primers and probes for detection of 2, 3, 4, 5 and/or 6 of R124C, R124H, R124L, R555W, R555Q and/or H626P. In some embodiments, the kit includes primers and probes for detection of 2, 3, 4, and/or 5 of R124C, R124H, R124L, R555W and R555Q. In some embodiments, the kit includes primers and probes for detection of R124C, R124H, and R124L. In some embodiments, the kit includes primers and probes for detection of R555W and R555Q. In some embodiments, the kit includes primers and probes for detection of R124C. In some embodiments, the kit includes primers and probes for detection of R124H. In some embodiments, the kit includes primers and probes for detection of R124L. In some embodiments, the kit includes primers and probes for detection of R555W. In some embodiments, the kit includes primers and probes for detection of R555Q. In some embodiments, the kit includes primers and probes for detection of H626P.

In some embodiments, the reagents in the kit are included as lyophilized powders. In some embodiments, the reagents in the kit are included as lyophilized powders with instructions for reconstitution. In some embodiments, the reagents in the kit are included as liquids. In some embodiments, the reagents are included in plastic and/or glass vials or other appropriate containers. In some embodiments the primers and probes are all contained in individual containers in the kit. In some embodiments, the primers are packaged together in one container, and the probes are packaged together in another container. In some embodiments, the primers and probes are packaged together in a single container.

In some embodiments, the kit further includes control gDNA and/or DNA samples. In some embodiments the control DNA sample included is TGFBI R124 normal. In some embodiments the control DNA sample included corresponds to the mutation being detected, including R124C, R124H, R124L, R555W, R555Q and/or H626P. In some embodiments, a control DNA sample corresponding to TGFBI R124 normal and a mutant DNA sample corresponding to R124C, R124H, R124L, R555W, R555Q and/or H626P are included. In some embodiments, a control DNA sample corresponding to TGFBI R124 normal and a mutant DNA sample corresponding to R124C, R124H, R124L, R555W and/or R555Q are included. In some embodiments, a control DNA sample corresponding to TGFBI R124 normal and a mutant DNA sample corresponding to R124C, R124H and/or R124L are included. In some embodiments, a control DNA sample corresponding to TGFBI R124 normal and a mutant DNA sample corresponding to R555W and/or R555Q are included. In some embodiments, a control DNA sample corresponding to TGFBI R124 normal and a mutant DNA sample corresponding to R124C are included. In some embodiments, a control DNA sample corresponding to TGFBI R124 normal DNA and a mutant DNA sample corresponding to R124H are included. In some embodiments, a control DNA sample corresponding to TGFBI R124 normal and a mutant DNA sample corresponding to R124L are included. In some embodiments, a control DNA sample corresponding to TGFBI R124 normal DNA and a mutant DNA sample corresponding to R555W are included. In some embodiments, a control DNA sample corresponding to TGFBI R124 normal and mutant DNA sample corresponding to R555Q are included. In some embodiments, a control DNA sample corresponding to TGFBI R124 normal and mutant DNA sample corresponding to H626P are included. In some embodiments, the concentration of the control DNA sample is 5 ng/µL, 10 ng/µL, 20 ng/µL, 30 ng/µL, 40 ng/µL, 50 ng/µL, 60 ng/µL, 70 ng/µL, 80 ng/µL, 90 ng/µL, 100 ng/µL, 110 ng/µL, 120 ng/µL, 130 ng/µL, 140 ng/µL, 150 ng/µL, 160 ng/µL, 170 ng/µL, 180 ng/µL, 190 ng/µL or 200 ng/µL. In some embodiments, the concentration of the control DNA sample is 50 ng/µL, 100 ng/µL, 150 ng/µL or 200 ng/µL. In some embodiments, the concentration of the control DNA sample is 100 ng/µL. In some embodiments, the control DNA samples have the same concentration. In some embodiments, the control DNA samples have different concentrations.

In some embodiments, the kit can further include buffers, for example, GTXpress TAQMAN® reagent mixture, or any equivalent buffer. In some embodiments, the buffer includes any buffer described herein.

In some embodiments, the kit can further include reagents for use in cloning, such as vectors (including, e.g., M13 vector).

In some embodiments, the kit further includes reagents for use in purification of DNA.

In some embodiments, the kit further includes instructions for using the kit for the detection of corneal dystrophy in a subject. In some embodiments, these instructions include various aspects of the protocols described herein.

EXAMPLES

Example 1

DNA Extraction (DNA Extract all Reagents, ThermoFisher)

DNA was extracted from oral epithelium or hair root or whole blood as described below and in line with the disclosures provided herein.

For DNA extraction from oral epithelium or hair root, the sample was first pre-treated in 1×PBS 300 µL. Next, 30 µL Lysis solution was added to tube and the mixture vortexed. The mixture was then incubated at 95° C. for 3 min. Next, 30 µL of DNA Stabilizing Solution (from Life Technologies/Thermo Scientific, USA) was added and the mixture vortexed. The mixture was then centrifuged at 13,000 RPM for 1 min.

For DNA extraction from whole blood, the sample was first pre-treated in 1×PBS 300 µL, starting with 3 µL of whole blood. Next, 30 µL of lysis solution was added to tube and the mixture vortexed. The mixture was then incubated at 95° C. for 3 min. Next, 30 µL of DNA Stabilizing Solution (from Life Technologies/Thermo Scientific, USA) was added and the mixture vortexed. The mixture was then centrifuged at 13,000 RPM for 1 min.

After the above procedures were completed, the DNA concentration was read using a commercially available Tecan® Infinite® 200 PRO NanoQuant. For quantitation, 100 µL of eluents were pipetted into a clear 96 well plate. Next, 100 µL of prepared blank solution was added to well H12. Concentrations were then read using the manufacturer's instructions provided with the NanoQuant.

Reaction mixtures were prepared using the probes and primers described below in Tables 5 and 6.

TABLE 5

Probe Sequences

| PROBE | SEQUENCE |
|---|---|
| TGFBI R124Normal (SEQ ID NO: 25) | VIC-CAC GGA CCG CAC GGA-MGB NFQ |
| TGFBI R124H (SEQ ID NO: 26) | FAM-CAC GGA CCA CAC GGA-MGB NFQ |
| TGFBI R124C (SEQ ID NO: 48) | FAM-CAC GGA CTG CAC GGA-MGB NFQ |
| TGFBI R124L (SEQ ID NO: 49) | FAM-CAC GGA CCT CAC GGA-MGB NFQ |
| TGFBI R555Normal (SEQ ID NO: 45) | VIC-CAC CAA GAG AAC GGA-MGB NFQ |
| TGFBI R555W (SEQ ID NO: 46) | FAM-CAC CAA GAG AAT GG-MGB NFQ |
| TGFBI R555Q (SEQ ID NO: 50) | FAM-AC CAA GAG AAC AGA G-MGB NFQ |

TABLE 6

Primer Sequences

| PRIMER | SEQUENCE |
|---|---|
| TGFBI 124 F (SEQ ID NO: 1) | TCC ACC ACC ACT CAG CTG TA |
| TGFBI 124 R (SEQ ID NO: 2) | CCA TCT CAG GCC TCA GCT T |
| TGFBI 555 F (SEQ ID NO: 43) | ACA CAG TCT TTG CTC CCA CAA A |
| TGFBI 555 R (SEQ ID NO: 44) | ACT TAA GTT GGT CTT TAC CCA AGA GTC T |

The components and ratios used in an exemplary reaction mixture are shown below in Table 7.

TABLE 7

| Reaction Mixture | | |
|---|---|---|
| All reagent extract (whole blood) | | 3.00 μl |
| GTXpress TaqMan ® | | 10.00 μl |
| Primer (124R) (reverse) | 10 pMol | 0.50 μl |
| Primer (124F) (forward) | 10 pMol | 0.50 μl |
| Primer (555R) (reverse) | 10 pMol | 0.50 μl |
| Primer (555F) (forward) | 10 pMol | 0.50 μl |
| Probe (NL/VIC) | 10 pMol | 0.20 μl |
| Probe (R124H/FAM) | 10 pMol | 0.30 μl |
| Probe (R124C/FAM) | 10 pMol | 0.20 μl |
| Probe (R124L/FAM) | 10 pMol | 0.50 μl |
| Probe (R555N/VIC) | 10 pMol | 0.20 μl |
| Probe (R555Q-1/FAM) | 10 pMol | 0.20 μl |
| Probe (R555W/FAM) | 10 pMol | 0.20 μl |
| DW | | 3.20 μl |

Exemplary PCR cycling conditions are shown below in Table 8.

TABLE 8

| PCR Cycling | | | | |
|---|---|---|---|---|
| Pre-read | Hold stage | Cycling Stage 40 Cycle | | Post-read |
| 60° C. | 95° C. | 95° C. | 64° C. | 60° C. |
| 1 min | 20 sec | 3 sec | 30 sec | 1 min |

The above protocols were used to generate the Real-Time PCR data provided in FIGS. 4-8.

REFERENCES

All headings and section designations are used for clarity and reference purposes only and are not to be considered limiting in any way. For example, those of skill in the art will appreciate the usefulness of combining various aspects from different headings as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

TGFβI gene sequence (NCBI Reference number NG 012646.1):

```
  1 gcttgcccgt cggtcgctag ctcgctcggt gcgcgtcgtc ccgctccatg gcgctcttcg
 61 tgcggctgct ggctctcgcc ctggctctgg ccctgggccc cgccgcgacc ctggcgggtc
121 ccgccaagtc gccctaccag ctggtgctgc agcacagcag gctccggggc cgccagcacg
181 ggtaagccga gccgcctggc caggggctgc ggaaggtcag gtagtcgggg ctcggagcgc
241 aagccgctgg gggcattgaa ctgggctggg ggcgcagggg acaaagcccg aactaaaaac
301 cttgcagcat ggagcgctcg gacaccagcc ctgcacgcgg tggaaggaga gagggaggga
361 ggtggaggac catggaggga aagcgggagg ccgccgcttt gtagaaggga gtggggaagt
```

-continued

```
 421   ggaccagaga ctttcgacgc aggccaagag cctgagacgg acagcgcttt cagcttctcc
 481   tcccagccac tgcagaaagg gggaaatggc aactctttgg ccataatcac cgtgggaggg
 541   tgccaagggc aaagcccacc cagcagtaca cctattccaa cccagccagg cccccggcca
 601   gcgactccag acaagaacct gggccacaca cggtggcagc atctaaggtg ccccaggctc
 661   ctgtgctcct ggccaggccc tgcactcaga cactgctggc acccgacact gctctctggg
 721   tacagcaagg gcaatgtggc acttcttgtc ctgcccgatg aagagcagga gaatgcactg
 781   ggccctcaca cacactgttc aaatgggaa actgagtcct gagtggttcc actttcccac
 841   agtcctgaag tgtgcactgg agccaggatt ggagtctgtc ttaaagtaat agctgggttt
 901   gtaaatgtag acactatca ttgcaggaat tcctttgaga ccctgaagat gtgttggctt
 961   taggagacaa actcaagcag aaggtctggt ctgatagtgg ccctaatact gacccaggca
1021   gaggcaggca acatttctac ctcaaaaacc aggccatacc tgcgtcacaa atacccaggc
1081   tttgctgcag cttccagcct acctggttgc accaacttct ttttcataac taggtaaaac
1141   tatatatgag tagaatcttg tagtgactcc tcagaggaag cctaaatacc atcgggtct
1201   ggcgttcaca cccacaagca atgcccaaac ctccaagaga ctgggcagat ctgtgctcaa
1261   atcaaaactc attgttgggg gtgatagagt tgacttcaca ggccctgaaa gtcttggctc
1321   cttgcactag gagtgctctg ggtacgggta caggctgccc cttgtagggc atagttgctc
1381   ttgtttcctc tacttgtggc tttatggtct aggcctttca ggagtttggg gctctggcgg
1441   agagggcctg ctgggagcac atctggccac cctgcagagt gaaatcaaac caggcctggc
1501   tgcaacctca cacccctcct ggaaagagga gaatactggg gatatcctgg ggtctttctg
1561   gaagtgggag aatcagcttt gacttgggca gtgtgcagaa tagagtgagg gggatgtca
1621   gaaagatgag agggatatga ggcctcaaca tcaaaatgca agcacctggc atttttatta
1681   tctctgccca cctctccgtt ggtctctctg cctttcctgc caatgaattg tgttatgttt
1741   gggtgcctca atttgcctag gagggttcta tttcttctgt atcttcgcca ctaagtcagg
1801   agaagatcct tatagcatgc cctgcaacag tgtcacctgt aagggcatct ctctgcacag
1861   ccacagtgaa ggatcctcaa aggtattgag ggctttccat caagagccat ctttacagca
1921   aacctctttc ccttcagagc ccagaagagt gctgaccagc tggaaaacag ggttttttc
1981   ttaaatgcag atgctcttga ttatgagttc cagatattag atcaacttcc ccaccatacc
2041   cctgcaggca aagcctctta attagcttcc tgcagcacag ctggaaaggc ctattgtaat
2101   ctgtgatggg cagagtaatc taagaagtca caggagcacc cctgtcccag tagaatctgg
2161   atgcgcaggc acatgaacca tggcaaaatg gttgcaggca cagttgtatt tactctgatc
2221   taactgtccc tgttaatgcc acagggctgc ctggcctggc acacagggct gtggcgcctt
2281   gtgcaaatgg ataacgttgt tctagctcca gcctttcatt caaagtgaaa actgttagaa
2341   agggaaggaa aactttgcta ttttaaggaa ttgtagcgtg ctgcctgata tgaaggaaga
2401   aataacagct gtgccttgct tgtgcgcagc actcgattgc cgcttttgct ttcgacctca
2461   ccacaacaca gtgagatcta ctgttcatgt tcccatttta caggaggtga aactgcagct
2521   tagtgaggta gagagtgact tagttcagac acagaatgct gttgggagag taataactat
2581   gatatggtct cttgactccc agctatatct gtgttgctat agggaagggg aaaaataata
2641   ctgaaagaga agtaaaaata caatcacact tccaaacatc aaccaccaaa aactgaactg
2701   aatttcctga agcacttggt tttcaaatct aagctgaaca tcaatgcgtg tattcttgag
2761   gcccagaagc aacttgctca tttcaattaa gcttcagcat gaacttccta tgtacacagc
```

-continued

```
2821  ccacccacac tccccgatgt gagaaggaga gggtcacagc cgcccccagc ctctgctgct 2881  gccacaagga cagcagcagt ggaaacattc agcaaggaa tgttggagcc acatccacaa 2941  gagactcact gaagattcgc caaacgccta cggaaagtgg cagggaattc attgacagta 3001  attgtttcct gcttgatcag attgaagagc ttctgggatt ctgtaacaat aaataggacc 3061  gggggctgga gtatggccag caaggactct tcaggggtta ttcagggact gtctaacctg 3121  tgaatcctag gcagcaaaca gaaaccaggt attcagaaat ctggaggatt tggtcaggcc 3181  cagctaggac tagggaggca tgggcctctg ctggctgtgg tcccttctcc agccttcact 3241  tctcttgtcc ctagatcctt acatggattc attaatgctc attgtccctc ctgggcccac 3301  tcactttcac ctgttgaaca aaaaactggc caagaggtga cagtcatatc accgcagaag 3361  agacagggca gagaaatgaa ggggcagaat ggactcccac ccaaaagcct gactctgaat 3421  atttgagaat tgttcaagtt cctgcagagg aatcatgatg gggacagtag gtgtagtttt 3481  tactgcaata ttggtgtctt cttaacaaat acgctgcaca tcaagtgatg tctgtggatg 3541  gcattcttaa agtaacaggg aaattgatgt taaagaaata cttcatcctt gggtgatac 3601  ctgaagttct ctgagcttgg aggtcttgtg aaagccctca gtattgtttg ttttatttgc 3661  tttcctctga cttgtgattc agtcagatgc atgcctgcct ctggctcagg aagatcaacc 3721  ctctcctgac tgaccacgcc tctcctgact gaccacgtag cacagcagct tcctttccct 3781  aggggctcct aatgaagctt tcacaatcac ctggcctgag cacagttggg gtcaggactt 3841  ggtatacttg aaaaaaacat gcaaaccaa aatcctgtgg ttctggaaaa ggcttcttag 3901  cagaaccccc agacatttac actctgcttt ttcacagggt ccctgaggat tctttggatc 3961  tgggtagttt ggggagcagt attttcaaca agttcatttc gtgctccttc tacaccctgc 4021  ctggatgcta ggccccatct agaatgtgaa caacagaaca aggcagaaca cttgtcctca 4081  aggttctgtt gagtgttaga tgcagagaag agacaccccc cacctccccg catcacttac 4141  aggaattctg tttgaaccc aacatcaaat aaggaccgta tccactgtca gaggatggga 4201  agcagcatgt catctgggac attggagaaa ggctcctggg ggaagtggga cttgagctgt 4261  gatctaagta atgaacaact gagagttaaa tggagagca tccctatca gggtcctgag 4321  agcaaccagc catggtttaa accagctata aagcctcggg tttataggat agacagtaac 4381  aatggcttgt ctttgggagc caagcagctg gtccaggcat gcagagcatg tctgtatgga 4441  gagctgcctg agagatgctt ttgtttacac ttatcaattg cccatgtcaa agaaggatat 4501  gtacatgaag ttacatcagt atgtaagaga gattttaaca atttttgcag gggaagcttt 4561  catggggct gatgggaatc taggtaaaca gaaccaaagt ctaaacccaa gatatcccca 4621  gtaccaagac tgaaatgact ctctcctcta tctctagaaa gttccagtga cccaaggagg 4681  caaacacgat gggagtcatt aaagtggggt ggacgtgctg atcatcttcc taattctgct 4741  gcttttgttt tcagccccaa cgtgtgtgct gtgcagaagg ttattggcac taataggaag 4801  tacttcacca actgcaagca gtggtaccaa aggaaaatct gtggcaaatc aacgtgagta 4861  tctgtaacca gccaggagac caagctgtat gcacgctggc tgcagttccc cagggcctgg 4921  gccagccttc tagaaggtca ggttgcctaa aaagccatga agatgcatgt gcgaacatgt 4981  ctgggacctg cgtgctaggg agtggcattt ttaggaagct ggccaatttt gttttgcatt 5041  tttaaggctg ctgacaagac ttggagacat ttttcagggc tggtttgggt tgcaagaaa 5101  catgaaacac tgcgtgtgtg tgtgtgtgtg tgtgtttctc aatcctcata aataataca 5161  gatatgcagt ggagaagcca ccagcatgtg actctggaaa agaaagccca ttggtgaatc 5221  tgtactaaag aatgccatcc ctatcttaca gtcctaaggt aaacacccca aaaagactta
```

-continued

```
5281   gagcactaaa catatgcaga ttatgagaca gcatagcata taatatttgc acagacttcc
5341   tcattcaaac cctagctcta cctgggccag tcgattcatc tttagaaccc tccattgctt
5401   tacctgaaaa gttcgtataa caaaaggacc caccttatgg ggttgttaca aggattgaat
5461   gaaataatgt acataagaga ctgaatatgg tgcccagcat atatcagtgc tcaataaatg
5521   ctagctacta ttattattat caccctagat ttgcaaatct agaccacaca agcagaagta
5581   agagtgccaa cggggtgtgg accagtgtgg ttacaatagg gcttgttgat gtctgtttca
5641   gcaaggaggg aggcagcttt taccccactg cccagctccc tggtggaatc aggtgcatgt
5701   tctaacaatt ctggggaaac ctaatctgtt ttggcactgt caacagatct caaagctggc
5761   tgtctcctat agctaggaag atgtgtatga caaatctcct gagccacttg tgaaggcctg
5821   accttcctcc tgtctccata cataatggga tgattaagaa actctaagcc actctcttaa
5881   gcacttttca atgttaggga tttttaagtt tattgttgtg acattgcttt tgagcagaca
5941   tctcctccaa tttaatagcc aactgaaaga agagaaaatg ctctttcctt aaactgtatg
6001   tggaaataaa tattccaatg tgtgaccctg attatgttag gcaattagca atcctaatat
6061   gaattgaggg aagttgggat tcatggcaca gctggggaga taccagcagt ccctgggagc
6121   ctgtccaggg caggtccatg gcagcttgct ccatgcctga ttgacagccc agcctgcaag
6181   ctaaaagttg agtgagctag gaggacacac tgccaagatt cagctaacag acacccagcg
6241   atattcttgc tgctatgaac aaaaggagac tatgcaaatt atacaccacc cattcttcca
6301   ggatgcctga cttaaaaaat aagaaaaaag atgggccggg cacagtggct cacgcctgta
6361   atcccaacac tttgggaggc cgaggtgggc ggatcacaag gtcaggagac agagaccatc
6421   ctggctaaca tggtgaaacc ccgtctctac taaaaaaata caaaaatatt agcgggcgtg
6481   gtggcgggca cctgtagtcc cagctactcg ggaggctgag gcaggagaat ggcgtgaacc
6541   tgggaggcgg agcttgcagt gagccaagat cgtgccactg cagtccagcc tgggtgacag
6601   agtgagacac cgtctcaaaa aaaaaaaaaa aaaagaaaa gaaaccttt agtactgatt
6661   gattttttcc catgtgtgta tattatctac tcaaattaac aattaattac ttaattaaac
6721   acaaagccag gcctcaccta attgcttctt ggaaggtgac cagagtgcta gtgccaagca
6781   aacaactctt ctatatctca agagccctgg gcttcagagg gccatctttt ttgttaattc
6841   aagtttctct gaaaatggag acccgtttat gatgacaagc tggctacagg gtagcatctg
6901   ccacactgtt tcgggggtgc cgctgggctg aagcatttgc ccagctagtt aacaatagct
6961   cgataacatt ccctatcagt gtccaggctg agaatactgt cagtgatgag tcgccttggc
7021   tcttgtacct gtatctttgt gtgccaggac aaggcacaag caacagagct gtgtgttgcc
7081   aaaatgttcc tgatgagcag gtcaaccct cggggggcagg tttggatatg ataatgtggt
7141   gatgtggtgg cgcagctccc ttacccagtg agcacaaggg gagtcctcta ggaaaaggaa
7201   gaaatgtctg gatgaggtgg ggagatgggg ttcagagtgg actcaggcaa agcccgatgc
7261   ccagtcccag ctgttggcct agtctcacaa agccagaagg atatgacatt tacattcaac
7321   tcttgaattt gtggccactg ctttgggcaa cttcaaagag agaaaatgaa gatagaaaaa
7381   tattatttga tataaaactt ctaggacaag agaggcccctt cctggaacat tacatgtagt
7441   attaggaagg tggagctgcc ctggaaaaga tccagagaac tcagagagag aagaggtgg
7501   aacccatctc tgttcttgta gagagctcag taagagtggc ttggcagggc tcctgtgtac
7561   ctgagaccaa gaccagtgag gaggctactg tctgaccacc atacggtcag aattcagtgc
7621   catgggtggt caggtgggaa ggggagagga ctgtgctggc tggagttgat gttatcctgg
```

-continued

```
 7681  ggaaagtagg tccctagatg cctttagttg agtgaggagc agactgggaa atgggagcac
 7741  agtagtggtt ggggcaaaaa ggactgtctc tgcatgaggt ccataggcag ttggaatttt
 7801  ctcagcaaga ctccagagaa ggaggctgga gcagaggtgt atgttgggat gaaaaggagt
 7861  aaagtatcat gggggaggag gcagctcagg ttgtcaaggg tcaagaaacc agaaggagaa
 7921  tttcaccttg gaagcagaca acgggtacca agcatacagg ggaatacttt gtggtgagag
 7981  gtcacacaga gatacaggag ccgacctggt gagacaggag cctggagcca cctgcctgct
 8041  tttgtgaggc cccagactcc actgctatca tcaggtgaag ctctgttgcc tgcacacaaa
 8101  agcttttctg catttacaaa gagagaaggg cctgagtttc tggtgcaatg cgtcaagctg
 8161  acatatggac tttattacag gaagtggtta ccagtgggtc cctatttagt ggctgttatt
 8221  gtgaatttta ttgttcggaa attcacttta gcatttattt cagatcctaa atagcaccgg
 8281  agtgatacaa tggctaatca aacaaagagg gctgtgggga gcagacagtc agcatccccc
 8341  tctgtgattt caggccctgg tttgattagt agccataaaa tttttttacgt gtggcacttt
 8401  gagcaaaggt gcaggaaatt gtggtcagga agcctggctg cctctcgaca ggcttccttt
 8461  gtgctagccc cagggagagg aggcctattt aacagccaag tccaagttga catcatggga
 8521  ctggaatagt catagcagga gctcagacat cataaacgtg gcataggagg gctggtgga
 8581  ggagctagcg ggtatgggtg gcagctattc attccaaaag tcttgaaatt gtttcacgag
 8641  caacacattt cacaagtgcg aagcccttct ctggagccaa gatgagctgg cagagcactc
 8701  ctgtttctct agtagcaagt gttcctttgc ccaggggcaa aaatattaat actccttcag
 8761  cactgcatta atgcttaaag atttaacttt taaagagatc agctggtgca tggtcgagct
 8821  tttccatcag ctggcagggc ttttttcagta ggtgtccttc tgggcagggc actggggaca
 8881  gctgacgtga aggtgaagaa gagctgtcgt tttcctcccct tatatcccac aaccttggtc
 8941  ccaagaggaa aaaaagaag atggtgagaa gtcatccaag cagaccccag acccatacta
 9001  gtgcctcctt tcctgtttca tatccctgtg cagccagctg ggatctcttg aataatctgc
 9061  tctggggggca ctgagattgg acatacacca aacagcggag atcgaccaaa cgcctctgtt
 9121  gggcagtgtt tcctgagggt tctgtcccat tctgtaaact aggaggctga ctagctgaca
 9181  aggaatttta ttctgttggg tatttacatg aacctatgtg ccacctgggg taagaccctg
 9241  tggtaggtag aaacatgact tcccaaaaat gtccacatcc taatctctaa ttctgtaaat
 9301  atattcccttt actggaaaaa gagactttgc aggtgtgatt aaattaagga tcataagagg
 9361  gagagattat ccaggattat ttgatgagtc taatataatc atcagggtac ttaaaagagg
 9421  gaggcaggct gtgcctggtg gttcacgcct ttaatcccag cactttggga gactgaggcg
 9481  agcgggtcac gaggacagga gttggagacc agcctgacca acatggtgaa actcccctc
 9541  tagtaaaaaa aaaaatacaa aaattagcca ggcatggtgg tacacacctg taatcccagc
 9601  tactcaggag gctgaggcgg gagaattgct tgaacccagg aggcagaggt tgtggtgagc
 9661  tgagatcgca ccactgccct ccagcctggg caacagagca agactccatc tcaaaaaaaa
 9721  aaaaagaggg aggcagtggg atcagagtca gagaaggcaa cgtgatgatg aaagctgaca
 9781  tttgagtgat gcaaccacaa gccaaggaat gcaggcagct tctcaaagct ggaaaggacg
 9841  agcaatggat tcttccctac agcctctgtg aggaatgcag cctttgattt taacccccata
 9901  aggccgattt ctgactctag cctctgaat tgtaagataa tttgcatgat ctcaagccac
 9961  taaatttgtg gtaatttgtc acagaaagca atgggaagcc aacacaggcc ttatttgttg
10021  acttatagat gcattttttct ttatttcaat gtactttat caatggtctc atgtagggta
10081  ttgctttcaa tgaagatatt aacatagttt caactttaag gtttatatct ggagtttctt
```

-continued

```
10141   tagaagcttc acaactgacc acttagtaaa cagtaagcat ctgttaagtg cttctcatat
10201   gtaagttcat tcaattctca caatcacact ataagataaa tatgattatt agcccattta
10261   cagatgagga gacaggctca aaagactttt atgcaacctg gtcaaagtca ttcactggta
10321   agctgaggag gtctgtccac ttccttttgc tgcccccagg gggtatcaag cctggcagtt
10381   agtgtcagcg acttaggagg tgaacaagtg agcaggcctg taggacctgg ctaaactgcc
10441   ccaggtctct gtctacagcc tcaaacctgt ggctgtgggt cccagagaca aggcctcctc
10501   agcatcagag aaggatgcct ttgtctcagg gtcatcaacc ttctccaggt tgctcacccc
10561   ctgctgtaaa ggggatcccc aagaccgctc atcagacaag gagcttggga actgaggaga
10621   cacagtcagc ctccaggagt gcccaaaatg ccctcacatg ctgcatacag attgccacaa
10681   ataaagtaca tccacattct gaagactctg tcctcatcac caaccaggct ggcccctggt
10741   gagggctgta gtggttgagg cctttgttgg tagacagtag gttaaagcaa gccatgattt
10801   tctattggga ggcttcagaa tcagctcagc tgtgtttcca agaccaggag ggcagaaagc
10861   aaaccatccc aggcaagcag tccatgggcc atgtcagatg tctagacgtt atgggtctgt
10921   gtttgctctg ccattcctct cggaaactat gatgcccgt atggtttacc ttcagtcaca
10981   ggtgactggc ctacagggcc attccttgtt ccaacgactt ctcgagtata attaatcccc
11041   aggcatttac ggccagagca gccggccaaa tccgtgaagt gcagtggttg ttttaaatta
11101   tattaacttc ttggaaactt attttaggga gagaaaactc agtacttctc tctatccaat
11161   cttgagtaaa aatgttagaa gggactggtg gagagcctcc cagacatccc tacacataga
11221   ctttgggttg acattatctc tttgcacctt ccttgaaact ttcttctaaa ttaggtgcct
11281   tccctaattt aggcaccttc ccagtactag tctgtgacct gttaggaacc aggccacaca
11341   gcaggagttg agtggcaggg agtgagcatt attgcctgag ctccgcctcc tgtcagatca
11401   gcagtggcat tagattctca tagcagtccg aatactattg tgaactgtgc gtgtaaggga
11461   tctagcttgt gcattcctta tgagaatcta atgcccgatg gtctgagatg aagagtttc
11521   ataccaaaac caccccttcc ccctgccacc atctggggaa atattgtcta ccacgaaact
11581   gatccctggt gccaaaaagg ttggggaccg ctgtcctaag ggatctgctt tttctgacct
11641   gaggttttc tttattagac tgtatctggc tgaggagaag cctgaagcct ttaatcggaa
11701   cagctttggc tgatgagatt agattcagaa accaacagat tggtcttttc tatgcaggga
11761   agcctaggaa ctgggggct atggctggga agcccctat tgtttccatc ctttcctatg
11821   ttcatcctgg aggaatggca tcagacccat gcctctgtga ttgctcccag cccatccaac
11881   cacagcatct atgttctgcc tgggaccagg gccagggagc atggcacact gagctgagta
11941   taaggagagt ggagcaggcc actgccagcc cagaaaattt tggtcaaagt tgcctgaaat
12001   cttctcagcc ttcgattcac agctgctctc tgctgctctg gggccatgca gaccagttca
12061   gaaaagagtt aatttgttgg ggcagttgga ggcaggtgga ctgccagctt tgacaccttc
12121   ccagcccaca ggctgctgca ctggggctga aggcgtggct aaccctgca cacctagaga
12181   gtgacagaga tgccagactg ggcagcagga aggcaagagg attaagagag agcttcctgg
12241   ctgaaagcca cactcggtta accaggaaaa agcccttggc acgagaagac tcagtggcct
12301   gagggactga gccttggttg ttggcatgt gctgcataag ccatccatgt gtgacagtag
12361   agtgtagtcc agccactgtg ggacatgggt gctgaaagac cacatggaga ggaacagtga
12421   gtgctgacaa gggctagcct tgatacttt ggagacaccc cctgtgtctt ctagatgtca
12481   gactttccaa atctgtctgc tatcctccaa acgtgcattt tcaagagcaa tggaaaaagg
```

```
-continued
12541  attggacttg atggaatgca gcaagagtcc taggtctgtt actacctacc tatgacctta
12601  agaaactcct tcaccoctca gaacccttac agctttcttt ctgattctat cctgagttac
12661  tctactccaa gctgagactt ttctgcttag atctatccct tcctcctaaa cccccaacct
12721  ccatttctcc tggtgtcttt ctttacacac ccctcagcat acacacacac ctagccacag
12781  gaaccaatga gttaatattt gaggagttgg ttttctttg tcctcaatga gatcctggtg
12841  aggccacttg agctgttcag ctcccttgcg gtattttggg gatggaactc agaagccaac
12901  aatatagaaa aagagtcttt ggccagcttt cccaggggct ccatgccata gagagtactg
12961  cacccgtgtg cacaggggggc cctgacatga ggactttgag gataacacta ttcctccaac
13021  tctgcttcag catctccatg gatttccaca cagacacttt aggaaagaaa ctaagtttgg
13081  ggggacttga cctaatccca catcacagcc ccagtaatac agccctggaa tttatcacag
13141  aaagcctaga atcccatgca tatcccatgc atatgcatcc ctagtcctat gggttcaagg
13201  cttggagctc tccctggatt tagctgggaa aagttggcag acagttcttc tctgtcttct
13261  agaaatatgg actagaatcg tgagtgtgag attgcaagta acttttaaaa tcatctagtt
13321  taacttcacc ccatttcata gaccaagaaa ctgagaccag agagagaaat ggactttcaa
13381  gttcaccctg ctagttactg atggatcaca agtcaaatct cctgattcta gcactgtttc
13441  tcttacacca caccaccttt gaaagtgtgt caatcaaatc ttactttagt tgcagaggat
13501  gactttagtt tctgaagata aaattgtgag tcaatcaaga tgagtcccaa gacaatagcc
13561  tgtttagccc ttataagttc agggatgaaa ggttagaaag aaacaggatg gaaggaggac
13621  tggagaaaaa acaaaagag gaaggaagga ggaggaagca acaggaaaa aaaagaatg
13681  tgcatagctt gtcactcctc agtcatttcc tgggagccca tttctagcaa agtgacagct
13741  gcaactccct ggccacctga gcatcttagc tgatctgtct ctgaaacacc ccctggagaa
13801  cagatgaatc aggcttcatc ttcgcttaac taagtcttcc ctgagacgac tccatttaaa
13861  tgaacaagag caggatttcc tgggcacact gagagcacct tccagaggcc cctccagagc
13921  cctaaagcct gtatttcttc cagtcggcct gtttctttcc tggtgatgtc attaaacgcc
13981  ctttgagagt cccacagtga gcagttctgc ggtaaaaccc gctgcaatta agtctgagt
14041  cctttcctgt ctcaaagggc atattcatat agaagaaagg aaaaggaagg actggctgtt
14101  tgcatttggt tccaggcctg ttgagtagag gtcgtgctca ctccaccgaa ggtacagggt
14161  agccttcagc agaacctggg gatttggttt taagcaagtc tttcttaggt gtgggctttc
14221  agaacacttc cttccttgca atattatttg aaattctcag tgttttagcc gtccccagaa
14281  tattggttcg ttaaagctgt gtatttcaga tctccagaca gtggtcactg tttgtatatt
14341  ttcaatttca aaccagaaaa caaaagttct tattgattac ttttttttatt taaaaaataa
14401  aaagtaagta tcttcgtaag aggagctttg ttttaatttt aaagtttaaa atttgattgt
14461  gaagacagag aaaaacttga tgattgtaga tatattcccc tctttggcta ttcaatcaga
14521  gaactagaaa atcatgagag atttaatgac cactgcctga tacacatatg tgttttacag
14581  atgaggaaac tgagacccag agagatgatg aaattggctg aggatggccc agctggtcag
14641  tgaaagactc agagccagag ctggtgcagg gctcttttcta ttccttcctg ttccctttca
14701  ggaacactca ccatcggctt tcctgtgaat aatgttgaga taaaatcctt ggtgcattat
14761  gttttctagt cacaacattg actaggctgc cagagtcctc tgttctccca gttggttggc
14821  tgtaggtgtt ggcagccgcc aggagcattc tacagaacag aggaggagtg agactctcct
14881  tgctcaggaa aggcagacct atgacttagc aaataactcc taagaggaga gtgtttcacc
14941  caccattcct cttccttggc tgtggaggca acttagtgga gagggccag atgacctgtg
```

-continued

```
15001  aggaacagtg aagccctgcc taacacaatg tatggttgtc ttgttacaga gtcatcagct
15061  acgagtgctg tcctggatat gaaaaggtcc ctggggagaa gggctgtcca gcaggtgaat
15121  gaatcctccg ggccttgcct gttggtgtgg gtggaaggga atggtgggag agaggagtac
15181  ccacataaaa ggcagcagag tgtgaatggg ggcagtggca caaggacatg gcattctccc
15241  cacgtgccca ctggccccag gctctatgcg aggggctgag gaatggaagc tggaaacagc
15301  gcatttcctg agctgctcct cctggcctcc ttaccacact ggtggagtag actccaactg
15361  tggcctgtcc atgcccttcc cagcaggcac aggctcaggc tcaggctctt ggcctctgcc
15421  tctggctggg agtgattcta aacacatcca gcagggtcag cctgatagcc catcagtttc
15481  cgatcagctc tgctagagag ccgatgggat gtgggaggag ggggtcactg gtgggctggc
15541  aaccccaagc catccccatc tccctctgtg tctaaacttg gccctttgga gttcggtagg
15601  gagaagagcc ataggccagg tgggctcacc cagagtcagc agagagtccc acaaatggtt
15661  gcactgggcg aaagacagca tggcacctgt gaattttatt agagcttttc ttttagtgct
15721  acacacaagt gactgtacag gggagttagt attttgtttt aattttgaaa tagagtcatc
15781  ttttggtatc tgcgggggat tgattctagg acccattcta ggatgccata tcctcagatg
15841  ttcaagtccc tgatataaag tggtatagta tttgcatgta atctatgcat attcttccat
15901  gtactttaaa tcatctcaag attacttata ataccaaata taatgtaaat cctatgtaag
15961  tagttgttat accctctttt aaattttgt attatctttt attgtatttc aaaaaatatt
16021  tttggtccat gtttagttga atctgtgggt gaagaaccca cagatacgaa gggccaactg
16081  tattggctat ttttttagtt aagaatgtga gactgaggcc aggcgcagtg gctcatgcct
16141  ttgattccag cacttttggga ggccaagagg ggacgatcac ctgagccaag aattcgagac
16201  cagcagcccg tgcaacatag tgagaccttg tctcttaaag attgtgagac tgggctgggc
16261  acggtggctc acgcctgtaa tcctagcact ttgggaggcc aaggcaggtg gatcaactga
16321  ggtcaggagt ttgagatcag cctggctaac atagtgaaac tctgtctcta ctaaaaatac
16381  aaaaaaatta gctgggtgtg gtggtgggcg cctataatcc cagctactca ggaggctgag
16441  gcaggagaat cgcttgtatc caggaggcgg aggttgcagt gagctgagat agggccgttg
16501  cactccagcc tgggcaagaa gagcaaaact ccatctcaaa ataaataaa taaataaata
16561  aataaatcat gagactgaga cataacagga aggagggcaa tttggttggt tccaaggttc
16621  ctagagtatg tgatgggaga ggttggtgcg ggtggggcca tggaggtact gactcaagtg
16681  gagggacagg tggggaaatg ggatgggaaa agaagattga ccttagaagg ggagctcaac
16741  ctctgaaccc taatttcaga cccttcaaaa tgaatattaa gctcattttg gtctaagaaa
16801  caaaaaacaa atgaacatga aactcatttt ggtcttataa ggtctgagaa accccttcta
16861  aacttcaagc tgctttaaga aataacattt tattacctgc aaatacacac agtactttgg
16921  agatttataa tagtctctta ttctaataga agccattagg gaaccagttt caataaacag
16981  gtaaatctgt aagactagtt tgtaattagg atatctgttt ccagtgtcca ttcctgcctc
17041  tgttatctaa atgtctggga acaagagctg tgctctgctg tgtttaaaat gattaaaaat
17101  caccaattag ttgagttcac gtagacaggc atttgactta ttgagttgtt ttaagaagac
17161  tataacaagc cttaagcccc ccagaaacag cctgtctttg ggctttccca catgcctcct
17221  cgtcctctcc acctgtagat gtaccgtgct ctcgtcaga gaaggagggg tgtggttggg
17281  ctggaccccc agaggccatc cctccttctg tcttctgctc ctgcagccct accactctca
17341  aacctttacg agaccctggg agtcgttgga tccaccacca ctcagctgta cacggaccgc
```

-continued

```
17401  acggagaagc tgaggcctga gatggagggg cccggcagct tcaccatctt cgccectagc
17461  aacgaggcct gggcctcctt gccagctgtg agatgacctc cgtctgcccg ggggactctt
17521  atggggaact gccttacttc cccgaggggt gggcatgatg aatgggagtc tgcagtcatt
17581  tcctactgtt tcaggaagct ttctccttaa ccccttagaa aaggctgtgg aacttgagct
17641  aaaatatgtc ttaccaggtt gcgtctaatg cccccgttc cctactgggc agaaagactt
17701  gggtgcttcc tgaggaggga tccttggcag aagagaggcc tgggctcacg agggctgaga
17761  acatgtttcc cagagttgca aggacccatc tcttaaacac agagtctgca gcccctaact
17821  gacaccctgt ccttcctcct aggaagtgct ggactccctg gtcagcaatg tcaacattga
17881  gctgctcaat gccctccgct accatatggt gggcaggcga gtcctgactg atgagctgaa
17941  acacggcatg accctcacct ctatgtacca gaattccaac atccagatcc accactatcc
18001  taatggggta ggggatcccc agccatactg catggcccctt ggtgcataat gaacccattt
18061  ctgttccatg tgtgggctgg tttctggggt ttaagctgta gacaacccac cctctttgtg
18121  cctgcttctc cttgggccct ctattccaca gcttgtggaa cccacatttt gctactgtgt
18181  ttgaaaacac tgttttctcc tcccggggct ttgggactat gcctctgttg tgttgactgc
18241  tcatccttgc tgcttctctg ggcagattgt aactgtgaac tgtgcccggc tgctgaaagc
18301  cgaccaccat gcaaccaacg gggtggtgca cctcatcgat aaggtcatct ccaccatcac
18361  caacaacatc cagcagatca ttgagatcga ggacaccttt gagacccttc gggtaaggga
18421  ctgccctggg tggaggccca ggcttgggac acattgcctc caagaggggg cctagcagga
18481  actcttctgc aggagaggta gaggatggct cctgtagggg aacatagagc aggttccct
18541  gaatgccctt gaacatggag aattcattga ccagacattc agcttgacct aacctgtgaa
18601  attctccatc ttctttataa agtgttccct tccttgcctc ccctggaaag gtcagtggtg
18661  tgtggctgca gcagcacagt gtcctctgag ccctggacct gcactgtggc ttccagaggt
18721  ggcagttccc acatgggta ctagaataaa tggcctatca ggctgtgtgt gctttgggat
18781  cacatgtccc caccctagga ccctggttcc aaccatacgc atgttctctt ggagcccaga
18841  acagcagaga agccaccagt gtggacacag aagtcaaggg tctgatttcc agcctggctt
18901  ctgactgctc tggggccgca ggaatacggt tccttccccc atgcccagca ggcatttgtc
18961  ttacaactgg agggggaaggc atgttcctct tggcaaggac tgctcaggag aagtggagg
19021  caggctgccc tgtcagggtt tttgccttga ttcaaggaga acttcctaac cacaaaggat
19081  acaagtggga gtgaggcgga ccctccctag agatctccaa cacagagaga caaacacgct
19141  ggggctggct ggcactgaca ggcctcgcag gtgtggatgg ctgttagctg ggagcttcgc
19201  tgtctaagct cctctcccat gcttttcttc tgggttgctc gaaggacggg ggtctgcaag
19261  aaaatgatgt tcccacatag ttggcagcac gtgaacagca attgatccct ttgcatcacc
19321  tcctcttact gtttagattt ggtaaatatt tcttccttcc ctcttctgac cctccatttt
19381  gccgatcttt ccttcttata acacatactt actaggtacc tgctacttcc cgggtgggcc
19441  tatgtgccag gagtatagag gtgaacaagg aaggcaaagt tctattctca gtagagctaa
19501  tactctatct ggagagagac aacaaacaaa tcaacaaggt agccagggc tgtgataatt
19561  tatgtcaagt gggcaggtaa atcgggagtg acagtagtgc agggaggatt ggaaagtcag
19621  ggagttctct ctggaggagg tggcttttga tctgcagcct aaaggatgag aatgggtcca
19681  ttatacaaaa tgctggggca agagcacacc cagtagaggg gagagtaata gcaaaggctc
19741  agggcaggaa gggcaaggga gaggccagtg ggtgaggtca catgtgaagg gcatacaatg
19801  ggcaaagaca aggccagagt ggccaggccc aatcctccag gacttgcaga cctgggaaag
```

-continued

```
19861  agtgcatctc catcctggga gcagcaggaa accactcagg cctttagaag atccttctgg
19921  cagctgtgta gagaatgggt ggtgtgatcc ttccatgcat gggctcatgt acgtgattac
19981  cagtaactgt cgagtgacag tgtgaggagg gctgcaagcc atgagtgtag gcacagcaga
20041  cagactcacc tttgtctggc ggtgagatgg ggtgggaagt gtgccaagtt gacctcccaa
20101  agaaatgata ttttagtgga agaatgaata gaatcagaga agcaaagtaa gagggaagag
20161  cagagaggac agcagggaca aggacttggg ggcaggaaga ggaaaggcag gttaaggaca
20221  tgaaagatgg ccaggctggc tggagctcag gcccagcaag gcccctggg ggccatggtc
20281  atgggtgagc ttgggtttgg cttctgtttt cgtcttgggc ttctgtgaaa gcctcgagcc
20341  cttgcgggga accagtgaag ctgtgtgtgc atcttctgtg gggagtgcca gagtcttcag
20401  ggagcactcc atcttctctc ctccccacag gctgctgtgg ctgcatcagg gctcaacacg
20461  atgcttgaag gtaacggcca gtacacgctt ttggccccga ccaatgaggc cttcgagaag
20521  atccctagtg agactttgaa ccgtatcctg ggcgaccag aagccctgag aggtgagcat
20581  cctttggctc ctgctgctgc ctcatttgtg cagctagatt gagcccaaga cctgctctgg
20641  tccaagatga acataccacc tgccatgagg tgaccctcag gatatccact gcagccatgg
20701  gctggggtca tcctgtcctg ttgcttcagc taaccgtgtc tctagcagcc acactactct
20761  gagggctgac tacagaatcc agcagctttt gtctgggaga gctggactga agagaggcat
20821  agctggagac ccatagctgg ccctggccag aaacagggag agtgaaaggc tggaatagcc
20881  aaggccagag caaggctaat aggtagagca acagcttaca ggtgtggggg tggcagatac
20941  tggcaccctt gaaatggatt cctcatgccc acgcttcact attcttctct gtggctaggg
21001  gatttatgga taaaccaaaa ttacagttaa aaaccagcca taggccaggc acagtgactc
21061  acgcctttaa tatcagcact ttgggaggac aaggtgggcg gatcacctga gatctggaat
21121  ttgagaccag cctggccaac atggcgaaac cccatctcta ctaaaaatac aaaaattagc
21181  tgggcatggt ggtgggcacc tgtaatccca gttactcagg ggctgaggca ggagaaccac
21241  ttgaacccag gaggtggagg ttgcagtgag ccaagcttgc accactgcac tccagcctgg
21301  gtgacacagc gacactccgt ctcaagaaaa aaaaaaaaa aaacagttat agtagtcaac
21361  ttttgactct ccatttcaga tttcgtcatg ccctcctcaa tgagctgcta agttaggcag
21421  tgcattgatt attgctgcag gagagggaag gaaggagcta acgtgttttc acatgttttc
21481  cttttggaga tgagaaagga ggactctgcc ttcccctac cctgcccctt tctactccag
21541  gacctctgaa aggccatgag cacaaagctg ctgcctgagt cccctgaaat gcagggtacg
21601  ccccaggtct ctgatgtacc ccaccacact tttcctctca acatattcc aggatcactt
21661  gatttctttt gaatctattt aaacccaccg tgtcaatgtg ctatataaaa tgtctaatgc
21721  atttcagaca ccctatacat ctatacattt aaagtgttct ccttctatct gtgcagggat
21781  gggaaaggc atatttctga agcacagat gggaagacgg gatttgttcc gtgtccaggt
21841  gattatggta cctctatgcg cctggccggc actgggaca gaggccatga aaatgaatac
21901  agcacagcct ttgcctccaa gaaacttaag acctagtaga aatggcaggc tttaaaacag
21961  gttgttggga tctgatttgg tgagtgcaat gacagagata ctcacagcac aaaatgggga
22021  atgagggcgg gcattgggac acacatagcc ttaaggggcc caaaggcttt tagaactgta
22081  ttccctatta aacatgatt tgcacagagc acattctttg ctttggagac ctcagaactc
22141  cttactatag gccgggcatg gttataatcc cagcactttg ggaagccaag gcgggcagat
22201  cacttgaggc tgagagttca agaccagcct ggccaacatg gtaaaacccc gtctctacta
```

-continued

```
22261  aaaatacaaa aattagctgg gtgtggtggt ggccacctgt aatcccagct actcaggagg
22321  ctgaggtagg agaatcactt gaacctggga ggcagaagtt gcaataagcc cagatcatgc
22381  cactgcactc cagcctgggc aacaaagcta gactctctca aagaaaaaa acaaaacaaa
22441  acaaaacaaa acaaaaaaaa ctccttatta taaactgtaa gaaaaaaaag gcccctactt
22501  cgtccctttt gcaaatctgc cttttcctac tcactaacca gctggttcag agcaaggaca
22561  ctctgtttgg tgccatcgct gcagactgga aggaagaggt ccttgcccca cacccaacag
22621  tctcctgctg ttaccggcag gttggcaggc aggcaggcga gaagcagcca gggctggtgg
22681  tgtgtccagt ttgaagacta gtttccagcc ctggccctgc tcaccctcca agtgggccctg
22741  gcaggttcct ctaccacatc gtggacttca ccttccttct ctaagaagct caatccccaa
22801  ggcctcattc ccataggcct tctcacccttt tttctttccc tctggctgaa tgtggccagc
22861  acgggcttcc aaggccatca actcgtctgc agcagcccca tgccttgcag ggcctcagag
22921  cttcctcctg cctatgacag tgtggttttg gttcccacac ttgggatcag attgaaactc
22981  gcctccgtgg tgagaatatg ggacatagac cctcggtgac cttggtgagc agcagtccag
23041  gccacctgct cagcctgggg ttgggggggg ctcctcctcc ttgactggtc cttgcatttg
23101  cctccatcca gcctgtctgg gctctccgag gcaatggaga ccagcaggag tcacgatggg
23161  tcaggagccc cctttgggcc tcagccctgc cctgcccct aaagtagcac ttggataagc
23221  aaataaatta ttatacttac tatttatggg tgtggtgaat gggatggcaa aggccaagtc
23281  ttactgatca ccaaacctta agatatatcc tggcagctag tagacccttg ggctaaatga
23341  acagaaaact ggacaaataa agtgtacaca ataactcaa agctgtcatt tgtacacttt
23401  tcgtcttttc ctactacagt ttacattttt ataaaggtga gtagatttct aaaatcccgt
23461  ggtaggctct cttgagtttt tcttgtatcc ctgaagttca gctacaaata agctaatcac
23521  taacatttgt tgagcattta ctctgttgtc aggccccgtg ccgagtgctt taggttcaga
23581  atttcatgtc atccccacag cagccctagg agatgaatgc aattcttatg tccacttgac
23641  tgataaggaa gttgaggttc aaagaggcta aatgactctc ccagggtccc acagctggaa
23701  agtggccaca gggccccagc tggttttcta gggcagcagg cagaaggcga ggaggatctg
23761  ggccctgtgg tgcccagcc tcatctgagg gtcctcatct gagagaacag gatcctcaca
23821  gcatgggcag gctgcaagtg gtccctgagg ttatcgtgga gtggaccctg acttgacctg
23881  agtctgtttg gaccccagac ctgctgaaca accacatctt gaagtcagct atgtgtgctg
23941  aagccatcgt tgcgggggctg tctgtagaga ccctggaggg cacgacactg gaggtgggct
24001  gcagcgggga catgctcact atcaacggga aggcgatcat ctccaataaa gacatcctag
24061  ccaccaacgg ggtgatccac tacattgatg agctactcat cccagactca ggtaggccag
24121  gcctccgggg gccttggccc tgcctggccc accatctctt ctgccatcct ttgtggcggg
24181  ggagggaaa ttcagagatc tttgggcgac ttccctgcct ggacccagct cacagcttct
24241  cggccactgc aaatgtgtgg gttgtgacca gactgatgtg tcttgagctt caggcttgca
24301  agtgcagtgg agaggcagtg gggagctatt gaaggggtct ggggacagac tcaatcacag
24361  aggcctttca gaagatctgc ctgctgtgca tgggcaaaga gggccacttg ctgacctcag
24421  agcatgtgct ttctcagtag tgcccaagct gtcccatggt cactgaccca gttagaatga
24481  ctgaatggac tttggcttgt gtctcattag gaatcctagc cccattctag tcttccagtg
24541  agatctgtcc atgagtgaag gaatctcaca ggaaaaaaca aaatgcttct atgggtgtgg
24601  ttgctggcct tatctacacc acagaagcca tcacacagac tgtctttctt cccattgtta
24661  gaatgtgccc tgaccaagca gcccacaggg cctgggacag aggctgatct ctgcctaact
```

```
24721  gagctcacct ctcctccctc tcctcctgac tggttagatt ttctaggtga ctgttcccct
24781  gatgacacaa gcccgctggg ccccagcagt gtttagaggg gttgttgact cacgagatga
24841  cattcctgct gatgtgtgtc atgccctggg gtggatgaat gataaatgaa aacagcgctt
24901  ttaacttttg aacccacttt ctccttcctt gtagccaaga cactatttga attggctgca
24961  gagtctgatg tgtccacagc cattgacctt ttcagacaag ccggcctcgg caatcatctc
25021  tctggaagtg agcggttgac cctcctggct cccctgaatt ctgtattcaa aggtaacatg
25081  gggaaggcat ccctgttaga ttgtccctgg aggcagcttc cccacccctg tcacctccac
25141  aacactctcc gatttacagc accccatggg acattagaac ttccactcag ctcaaccaaa
25201  agcagatgtg acttcagcag aaacttcaga ggctctgttg tttcattagg cagtgcagag
25261  aatgcctttg gggagccgtt cctcagaact caagacttga catctgggag gcagccgttc
25321  ctcagaactc aagacttgac atctgggaga gcagagcatt cccttgcctt tctatttgca
25381  gggtcacttg ccaatgtata gtcaagaggt cagagtgagg gtacagctga gctgcagccc
25441  caggaaggca gagaagggg ccaagttgtg tgcgtgcctg cccttccctc ttagggcaaa
25501  actccaaaca cccttgatta tctggatctt ctttaattct ccatagaaga taccagatgt
25561  taaggaatat tggcagcttc acttggtttc tcaatccctg tttccaaact caaggaggga
25621  tgggcttttt cactgtattt atctctcatc actctcttca ttgcaggagc acatctctct
25681  ggacctaacc atcacccttt cttgtagatg gaacccctcc aattgatgcc catacaagga
25741  atttgcttcg gaaccacata attaaagacc agctggcctc taagtatctg taccatggac
25801  agaccctgga aactctgggc ggcaaaaaac tgagagtttt tgtttatcgt aatgtaagtt
25861  ctgggtccta aatcatgctc tgggaagct ccttactgtg ggacttgtat tagtgtaaaa
25921  aaaaatgtcc tcaataagca ggagtttgca tgagaactgg ttgctgacaa ggaaggaaat
25981  aatttctgga aaatatagat aacaaaatga gatcctgcag aaggattgga atctcttttt
26041  ctggaggcct ttgagaataa accacacaat tatccaacct gtattgtgaa ggaataagtc
26101  cttcttgaat tcaggaatta acacctggga ggagggatgg agttcagact ctttctgagc
26161  ttatgagaag agaagcccc taaactaaaa tacagccctc cttggtccaa aaggtgcctt
26221  ctctcttctg ctgtatcttc tttgttttca aacccaacag ttaccctgga aatcaaaaag
26281  gaagtacaac tcaacatagc tcttgcctgg gaccaaccag caccatttgg ctaaagatgg
26341  ttatcatctg ttaaacaaag aaataaataa atgggttcaa cgtatttatt tcaacattgt
26401  caatggacct catgtgtaac tgatattctc attatgggac ctctgtgtga ctttattggg
26461  gcctctctaa ccgttctttc cttaaggaag accatttatt gttttatttc ctggagaaaa
26521  tacatcattt tatcccagcc ttaataaccc atcccagtgt atactccttc atcttcatgg
26581  ataatgaccc tgctacatgc tctgaacaaa tcaggaggcc cctcgtggaa gtataaccag
26641  tcctttcttt ctctgtccct cttctgtgca gagcctctgc attgagaaca gctgcatcgc
26701  ggcccacgac aagaggggga ggtacgggac cctgttcacg atggaccggg tgctgacccc
26761  cccaatgggg actgtcatgg atgtcctgaa gggagacaat cgctttaggt aattagttcc
26821  atccccgggt ggagcttctg cccagtggtc atgctggagt gggatgtggg gccccagcta
26881  tttgtcaagc tttcttctac cttggggatt caattaacac tagcagtgca ctgctgcgac
26941  cttccagact tgggatgggg aaaaggcaag ggtcgccttg aaagcttaca ttgggaagaa
27001  gggttacttc taagagtgta atcttcacat gcatgggaag cagggagggg ggactacatt
27061  tttatgactg aagtgcaagg aaaacatcac cctctcattg taaagctcca agtgagccaa
```

-continued

```
27121   gagcacatag tttacagtgc acgatgagcc tctcactctc tgcgcagtat ctgtttattg
27181   caactgaagc acccttgtga gtttgttttc ttgcccggct atctccattt ctgacttgct
27241   cattcacctt ggggtgctgt catattgaat gtttccctgt cactgacttc agccacctgc
27301   acaagggctt ggagaccaca cccctctgcc ctcccagaat catatccctg gaggctcagc
27361   tagtctctgg gtcagccata cctctgccct ttcttttccc tcctttctcc tgtggcctct
27421   gacgtctggc catttaacag agcttagcat ttttgctggg tgagagagc tggagcctgg
27481   aatcactccc tctttgtgca tacggagggc atgaaaacca aggtgtgtgc attccagtgg
27541   cctggactct actatcctca gtggtgaggt atttaaggaa atacctctc agcgtggtga
27601   ggtatttaag gaaaatacct gttgacaggt gacattttct gtgtgtgtat ctacagcatg
27661   ctggtagctg ccatccagtc tgcaggactg acggagaccc tcaaccggga aggagtctac
27721   acagtctttg ctcccacaaa tgaagccttc cgagccctgc accaagaga acggagcaga
27781   ctcttgggta agaccaact taagtacacg tctccatttt tctaaagtag tgatccctca
27841   gggccccagc agcaaacagt tggcacatca aggattgact tgaagggatt ttatgacaag
27901   actattagtg aaagagtggg cgggactaaa ggaactagca aaggatgagg ccaaccaggg
27961   actagcaacc ctgggaagcc tttactaccc ctaggcctgg gggaatggga ggatgagagc
28021   aggaaccagg gaggtcatga gccttggaca agggcacaga acagcagcca gagccatgtg
28081   cagccagcca ctgtcagaac catgcaaggg ggaccactca gcgcccagc ctccctctca
28141   gacagttgcc atctgggtct cttgttggct gatgcgagag caggagggag cccactgatg
28201   cagttcatag agctcagcct cctgggcagg aaaccgggca gagaggagta gaaaagaatt
28261   aagggtggct gcgaccagcc cagtcactga ggcacgtttc ccactggaga cctatgagca
28321   cagtgataat aaagccagtt acctgcactg actatccctc cagacaaaag ctttcccaag
28381   aagttagtca tggctctgag agatctagtt gaggatgttt ggcaggggat ctagtggtta
28441   cgggtggcta agaaaaatga ggaaggtaag agtatcttgc agcctgtgtt gggaggatta
28501   aataggatgc cacacacagg gccaggcaga cagcctggtc agtaatagcc atgacgatgg
28561   gggcggggg agcaggaatg ggagttgcag tgtttagctc agatgcatgc ctgtgagaga
28621   tgcttccact ctcacagaaa gatgagacca aggaaaagga ggaggaagag gaaggacctt
28681   gacaaccttt ggggcccaca ttgtctacac ctcccttcct gctctagagc agaatagaaa
28741   gttcaggttg caggcagctc taagttgaat tcgtgtcctg tttaattttc tttattgcta
28801   aatgaatgcc tgtgtctgtg atgctgacgt atgttcctaa ggagagggga gaagttcatt
28861   ctgaacataa acttttcatc ctctctctgt ccagcaagaa tggaatattc cccaagtggc
28921   ctgagccagc ttggcttct ttttgttttc aattatgtgg gagttgagga ggggatggg
28981   aaaagcttcc caaacacacc ctcccccagg cctgaggcac ccctggggga cagagagtgt
29041   tagaggttgg tacaggtgtt agagatattg aaaggacatc ccatgcaccc caggggctgg
29101   tgtggctctg tacttccagg caatattttg tggaagggga accttgtcag ctccaggttg
29161   tggatgtttg aaaatcagtt ggtacccagt ggctccatcc tctggcaggc atgtggattt
29221   gtcaataacc aagtgaactc tccaaaataa gttaaaactt cctcccttct cagtttcaag
29281   atgctggaaa tagctgttca taagccctgg ggaaatttag ccctttggct ggtaatggga
29341   gtatccgaga tgagagggca gctggaaact ttcggaatga cctcccacac ttaatttggg
29401   aaatgcctct gcacctttat gggcaaccag atgcctgccc cagttgctgg agacactgat
29461   gtgggctgaa aggaatgctg agacgtgacg aggagagatg ctgcggaggg aatatccccc
29521   tcagccctga cctcatcggc tccatggctc ctccacagta cagctgtcta ctctttaag
```

-continued

```
29581  ttctcccttc aggaaatagc catctcaaac agaatgtgca tttgagggca gaatgtgtaa
29641  atattgcact actgtgttat aaccgtcagg agccatgctg atgatgaaac gtcccagatg
29701  ccggtgctgg aaaggtccct ggctttccaa gcaaatattt atctcatgga aacatgagtc
29761  atactcacag aggagtatgg attaactcct tctcagcagc cagggagccc agcatcccag
29821  acagcatatt taacccagag gccaactgac tgctggggca gatttgtggt catgaacatg
29881  tgctttgtgt cctctgacca ttagacagat tgtgggtcac aacgttgagt atacagtggg
29941  agcttaataa gtgcttattc cctgggcagg gagttcttca tttcaggggt gaccacttac
30001  atcttctcct ctgggccctc cttgaccagg ctaattacca ttcttgggat taactctatc
30061  tccttttccc gcaacctgca ggagatgcca aggaacttgc caacatcctg aaataccaca
30121  ttggtgatga aatcctggtt agcggaggca tcgggccct ggtgcggcta aagtctctcc
30181  aaggtgacaa gctggaagtc agcttggtaa gtgtcctgca aatcaaaggc tggctaaatt
30241  tccccagggc agggctccag gacatatctc accccagga tggaattata cacacacaac
30301  cttcaagttg cagcccgaat ctctgagtgt aattcgtcca agaaaaaga gaaagagaa
30361  gagggtcttc agggaaatca agtgagatca tagttagaca tgagtaagaa cttccagatt
30421  tacaagggaa tagagcatct gatttggcat ctgagagagg ctattagatc ttccttctct
30481  taaggaggtt gtaggcaact agttatgtga ctgaagagat cagtctgtac tcacaccatc
30541  ccaccccca aacccagggc ttcactgagt tgtaccatga accagaccat cccaagaggc
30601  tttttgagtt ctgacacttg ctctgtgagc cttcccttgc tctgcacatt gatgatataa
30661  ctttgtaact gcactaagag tgttcctaaa gcagatagcc agccgagctc cagaaatctc
30721  cctggctgca cctgcagagg ccactgaccc ctctgtggag ggaccgctct tcagtgtgtg
30781  gctggcttct actctctgct cctctctctt ggtcttcagc catccattgc tcaccagttt
30841  ctcacgagga gcataggaag atatgcatgt agggaggtag gcacgggat gacttgtttg
30901  actttagcag gtcattcaag aatctcctcg cacctggttt cagatgctgg ggtcctgtct
30961  gtcacaggct tctgtgcctc ctaccccctt gagtttgtca catggccctt caggaaggcc
31021  tgagatagat ttgccctggg tgggcctcct atgagaaaat cttaagtgag cacccaggc
31081  aaaatggaaa gagcctttg cccagagcag gaagcctgtc ttccattcc agctgttcca
31141  cctacttagc ttaaaagagg cacttcgcct gtcttcagtc tcagtctcag tctcctcttc
31201  tgtggaatgg gacaataata tctactctcc ttatcataca ctgctgtgag gactgagtgg
31261  atcacacaaa aaagcattat gtaaattgca aagtgctaaa tccacacagg agatttgaat
31321  taatccacca cactgaaggt ctgtcaaggg cagggactgt ttcattcacc agagtatccc
31381  cagtctaaca caggacttgg catatgaaaa gtgttcagta ggccgggtgc agtggctcat
31441  gcctgtaatc ccagcacttt gggaggccaa agtgggcgga tcatctgagg tcaggagttc
31501  aagtccagcc tggccaacgt ggtgaaacca catctctact aaaaatacaa aattagctgg
31561  gcgtggtggc acatgcctgt aatcacagct actctggagg ctgaggcagg agaatcactt
31621  gaacccagga ggcggaggtt gcagtgagtc gagatcatgc cactgcactc cagcctgggc
31681  gacaagattg aaactccatc tcaaaacaa agaacaagga aaaaacgaa aactgttcag
31741  taaacacttg ctgaatgaat aaaataaata tataaatgta taaataaatg ctctactttc
31801  aaccactact ctgtttttct tttagaaaaa caatgtggtg agtgtcaaca aggagcctgt
31861  tgccgagcct gacatcatgg ccacaaatgg cgtggtccat gtcatcacca atgttctgca
31921  gcctccaggt aagtgtcgca tccccactga ctctgcagcc agtcctttc ttcatgtggc
```

-continued

```
31981  agttggtgga gagaagaaaa actgttctaa acaatgatga gaataacatg taattgtgat
32041  agttaaactg tgcctatgtg actgattgca gagtgaattg ggagctgttg gtttttgaatg
32101  caccacacta aggaatgtga ggacacattg ctctttgcgg agttgcccag ctatattagc
32161  tccctcgga cacagcccag ttttctgtat tcgcgtggat gctgtccgcg cgattcccag
32221  cactcctctt acagcatctc acctcagtgt atgttccttg cctccagtgc agttgaacct
32281  cagtcctgcc tctcctcatg tgtgcattca cctttcttgg tgctctctcc ccatgggcca
32341  agttctacca tgagttatga acattatgg agaaaacatg tctttggaaa tgtgagccag
32401  aaagcccacc agtgcccctc agtcacggtt gttatgaatg acatgctaat ggtttcactc
32461  tggtcaaacc tgccttttct ttcctcttca gccaacagac ctcaggaaag aggggatgaa
32521  cttgcagact ctgcgcttga gatcttcaaa caagcatcag cgttttccag ggtaagatgc
32581  ctgctaggtt tgcgcctagc ctgagcagcc tcaggtcctc tgtttgggcc atagaggagc
32641  ctctccagcc cctgtcttcc ttggctgctc cccagggctc tcttaaaact tctccccact
32701  cccactgagg catcctcagc cccagcctgt gtcaaattca gagtaaagaa ccaaggcaac
32761  tccctggctt tcatgggcca aagcgcaggc tttcacaccg aggcctctga gcctcagatc
32821  atggggaagt cactgctgga gagaacagac atagctctgg aagccatctg cccaagaggg
32881  cagcccatcc caagttcatc ttacagtggc caggcctgcc ctgagccggg gcctctgggt
32941  cactcttctg ctgtccatgg cattgcccat cctgggtgag gctggggctc tcctgggcac
33001  tgtatgtatt ctggatacag ggatactggg ctcgctatgt gtgtggagcc atcccttcct
33061  tgccccagcc ccacctccct ctcaaaccct ctctggctct ttctgagctt ccttttcctgc
33121  tcccagctt gcccagtgct cagtgcccca cttggctctt ttgctacttc gggtcaggtg
33181  gagcctcttg ggaatgtgaa gtgccttaca gaaagattgc acttcaagag gagaggctgc
33241  agggagccat cctaaaccca gaggcctgga gcttactgtg tcactttact tttgtacaca
33301  ggggtctcct tagtgccctc gagaaggatt cttggccctg agcttctact cctgaggcca
33361  cctctgtgca gccccagctc cctcaactct aggctgtagt ctcagtggga aagcctggct
33421  tgggggtctc ctaggaatgt ccacctgaag gcacacttga taggggcttg cacaacttat
33481  gtctgccaag gccacctgag gaactccctg gtgcctataa gttccacctt cccccttcctc
33541  ttcctcgccc cagcattttt tctgagtagg ggtggcaatg ggcaaagcca ttgtcataag
33601  cagttgcagg tataactttc actagaaaac ctgacacctt tgtgttttctt tcaggcttcc
33661  cagaggtctg tgcgactagg tgagtctggt ctgggtttga agtcattgca gacctgttta
33721  ggccttaccc ccaagcaagc ccaagcctgc catctgctgt atatagataa gaacatcatg
33781  gtgcagtaaa agaagcctgg ccttttggagt cagaacagca gggtgacttg gggtcagacc
33841  cagagcaccc catttccttc tctgtaagat gaggataata agagtaacaa cctttttaggg
33901  ttaaggtgag ttttcagctt aggaagtctg ggaatattgc aaagggcttg gcaggaaccc
33961  atggtgagga tctagttcca agttgatagg tacagaaaac cagaacatcg ggccttgagt
34021  aaagagtgaa gtttcacaaa ccacaaagca cctgctatgt gcaggagagc atggcagaag
34081  gaggctgctt ggccctggtc cttgagattc tgacagtgtc ctagacagac atggggagat
34141  ctgcacctat ttgacgttac caacttctct ttttcagccc ctgtctatca aaagttatta
34201  gagaggatga agcattagct tgaagcacta caggaggaat gcaccacggc agctctccgc
34261  caatttctct cagatttcca cagagactgt ttgaatgttt tcaaaaccaa gtatcacact
34321  ttaatgtaca tgggccgcac cataatgaga tgtgagcctt gtgcatgtgg gggaggaggg
34381  agagagatgt actttttaaa tcatgttccc cctaaacatg gctgttaacc cactgcatgc
```

-continued

```
34441    agaaacttgg atgtcactgc ctgacattca cttccagaga ggacctatcc caaatgtgga 34501    attgactgcc tatgccaagt ccctggaaaa ggagcttcag tattgtgggg ctcataaaac 34561    atgaatcaag caatccagcc tcatgggaag tcctggcaca gttttttgtaa agcccttgca 34621    cagctggaga atggcatca ttataagcta tgagttgaaa tgttctgtca aatgtgtctc 34681    acatctacac gtggcttgga ggcttttatg gggccctgtc caggtagaaa agaaatggta 34741    tgtagagctt agatttccct attgtgacag agccatggtg tgtttgtaat aataaaacca 34801    aagaaacata
```

TGFβI gene protein product (βIG-H3 protein sequence; NCBI Reference number NG 012646.1):

MALFVRLLALALALALGPAATLAGPAKSPYQLVLQHSRLRGRQH

GPNVCAVQKVIGTNRKYFINCKQWYQRKICGKSTVISYECCPGYEKVPGEKGCPAALP

LSNLYETLGVVGSTTTQLYTDRTEKLRPEMEGPGSFTIFAPSNEAWASLPAEVLDSLV

SNVNIELLNALRYHMVGRRVLTDELKHGMTLTSMYQNSNIQIHHYPNGIVTVNCARLL

KADHHATNGVVHLIDKVISTITNNIQQIIEIEDTFETLRAAVAASGLNTMLEGNGQYT

LLAPTNEAFEKIPSETLNRILGDPEALRDLLNNHILKSAMCAEAIVAGLSVETLEGTT

LEVGCSGDMLTINGKAIISNKDILATNGVIHYIDELLIPDSAKTLFELAAESDVSTAI

DLFRQAGLGNHLSGSERLTLLAPLNSVFKDGTPPIDAHTRNLLRNHIIKDQLASKYLY

HGQTLETLGGKKLRVFVYRNSLCIENSCIAAHDKRGRYGTLFTMDRVLTPPMGTVMDV

LKGDNRFSMLVAAIQSAGLTETLNREGVYTVFAPTNEAFRALPPRERSRLLGDAKELA

NILKYHIGDEILVSGGIGALVRLKSLQGDKLEVSLKNNVVSVNKEPVAEPDIMATNGV

VHVITNVLQPPANRPQERGDELADSALEIFKQASAFSRASQRSVRLAPVYQKLLERMK

H

---

What is claimed:

1. A reaction mixture for detecting corneal dystrophy in a human subject, the reaction mixture comprising:
- a first labeled detection probe consisting of a first nucleic acid sequence consisting of SEQ ID NO: 25 with a label attached to the first nucleic acid sequence,
- a second labeled detection probe consisting of a second nucleic acid sequence consisting of SEQ ID NO: 48 with a label attached to the second nucleic acid sequence,
- a third labeled detection probe consisting of a third nucleic acid sequence consisting of SEQ ID NO: 49 with a label attached to the third nucleic acid sequence, and
- a fourth labeled detection probe consisting of a fourth nucleic acid sequence consisting of SEQ ID NO: 42 with a label attached to the fourth nucleic acid sequence, wherein the only labeled detection probes in the reaction mixture are the first, the second, the third, and the fourth labeled detection probes.

2. The reaction mixture according to claim 1, further comprising at least a first amplification primer pair for amplifying and determining a TGFβI gene sequence from a biological sample from the subject.

3. The reaction mixture according to claim 2, wherein the first amplification primer pair comprises a first amplification primer and a second amplification primer, the first amplification primer comprises nucleotide sequence SEQ ID NO:1, and the second amplification primer comprises nucleotide sequence SEQ ID NO:2.

4. The reaction mixture according to claim 1, wherein one or more of the first, second, third, and fourth labeled detection probes is coupled with a first label, one or more of the first, second, third, and fourth labeled detection probes is coupled with a second label, and the first and second labels are different.

5. The reaction mixture according to claim 4, wherein the first label is VIC.

6. The reaction mixture according to claim 4, wherein the second label is FAM.

7. The reaction mixture according to claim 4, wherein one or more of the first, second, third, and fourth labeled detection probes further comprises a minor groove binder.

8. A method for detecting whether or not a human subject carries a mutation that causes corneal dystrophy comprising:
- (a) amplifying a first TGFβ1 gene sequence from a biological sample from a human subject using a reaction mixture comprising at least a first amplification primer pair and the reaction mixture of claim 1;
- (b) detecting whether or not a mutation is present in the first TGFβ1 gene sequence based on (i) the hybridization or (ii) lack of hybridization of the labeled detection probes in the reaction mixture.

9. The method of claim 8, wherein the first amplification primer pair comprises SEQ ID NO: 1 and SEQ ID NO: 2.

10. The method of claim 8, wherein one or more of the first, second, third, and fourth labeled detection probes is coupled with a first label, one or more of the first, second, third and fourth labeled probes is coupled with a second label, and the first and second labels are different.

11. The method of claim 10, wherein the first label is VIC.

12. The method of claim 10, wherein the second label is FAM.

* * * * *

SEQUENCE LISTING

<160> NUMBER OF SEQ ID NOS: 60

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
tccaccacca ctcagctgta                                              20

<210> SEQ ID NO 2
<211> LENGTH: 19
<212> TYPE: DNA
<213> ORGANISM: Artificial
<220> FEATURE:
<223> OTHER INFORMATION: primer

<400> SEQUENCE: 2
ccatctcagg cctcagctt                                               19

<210> SEQ ID NO 3
<211> LENGTH: 20
<212> TYPE: DNA
<213> ORGANISM: Artificial
<220> FEATURE:
<223> OTHER INFORMATION: primer

```
<400> SEQUENCE: 3
tgcagcccta ccactctcaa                                              20

<210> SEQ ID NO 4
<211> LENGTH: 16
<212> TYPE: DNA
<213> ORGANISM: Artificial
<220> FEATURE:
<223> OTHER INFORMATION: primer

<400> SEQUENCE: 4
aggcctcgtt gctagg                                                  16

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
tagtctctta ttctaataga                                              20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
gctgcagact ctgtgtttaa                                              20

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
ccatccctcc ttctgtcttc tg                                           22

<210> SEQ ID NO 8
<211> LENGTH: 16
<212> TYPE: DNA
<213> ORGANISM: Artificial
<220> FEATURE:
<223> OTHER INFORMATION: primer

<400> SEQUENCE: 8
cgggcccctc catctc                                                  16

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
cagagaaggg agggtgtggt t                                            21

<210> SEQ ID NO 10
```

```
<211> LENGTH: 19
<212> TYPE: DNA
<213> ORGANISM: Artificial
<220> FEATURE:
<223> OTHER INFORMATION: primer

<400> SEQUENCE: 10
gggcgaagat ggtgaagct                                          19

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
tcctcgtcct ctccacctgt a                                       21

<210> SEQ ID NO 12
<211> LENGTH: 17
<212> TYPE: DNA
<213> ORGANISM: Artificial
<220> FEATURE:
<223> OTHER INFORMATION: primer

<400> SEQUENCE: 12
agctggcaag gaggccc                                            17

<210> SEQ ID NO 13
<211> LENGTH: 19
<212> TYPE: DNA
<213> ORGANISM: Artificial
<220> FEATURE:
<223> OTHER INFORMATION: primer

<400> SEQUENCE: 13
tttgggcttt cccacatgc                                          19

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
ggcagacgga ggtcatctca                                         20

<210> SEQ ID NO 15
<211> LENGTH: 18
<212> TYPE: DNA
<213> ORGANISM: Artificial
<220> FEATURE:
<223> OTHER INFORMATION: primer

<400> SEQUENCE: 15
gtagtaccgt gctctctg                                           18

<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16
```
agttccccat aagaatcccc c                                           21

<210> SEQ ID NO 17
<211> LENGTH: 17
<212> TYPE: DNA
<213> ORGANISM: Artificial
<220> FEATURE:
<223> OTHER INFORMATION: primer

<400> SEQUENCE: 17
ggctggaccc ccagagg                                                17

<210> SEQ ID NO 18
<211> LENGTH: 19
<212> TYPE: DNA
<213> ORGANISM: Artificial
<220> FEATURE:
<223> OTHER INFORMATION: primer

<400> SEQUENCE: 18
acccctcggg gaagtaagg                                              19

<210> SEQ ID NO 19
<211> LENGTH: 21
<212> TYPE: DNA
<213> ORGANISM: Artificial
<220> FEATURE:
<223> OTHER INFORMATION: primer

<400> SEQUENCE: 19
aacctttacg agaccctggg a                                           21

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
gactcccatc catcatgccc                                             20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
agtcgttgga tccaccacca                                             20

<210> SEQ ID NO 22
<211> LENGTH: 24
<212> TYPE: DNA
<213> ORGANISM: Artificial
<220> FEATURE:
<223> OTHER INFORMATION: primer

<400> SEQUENCE: 22
gacgtcattt cctactgttt cagg                                        24

<210> SEQ ID NO 23
<211> LENGTH: 18
<212> TYPE: DNA

```
<213> ORGANISM: Artificial
<220> FEATURE:
<223> OTHER INFORMATION: primer

<400> SEQUENCE: 23 cccccccagaa acagcctg                                              18

<210> SEQ ID NO 24
<211> LENGTH: 25
<212> TYPE: DNA
<213> ORGANISM: Artificial
<220> FEATURE:
<223> OTHER INFORMATION: primer

<400> SEQUENCE: 24
ttctaagggg ttaaggagaa agctt                                       25

<210> SEQ ID NO 25
<211> LENGTH: 15
<212> TYPE: DNA
<213> ORGANISM: Artificial
<220> FEATURE:
<223> OTHER INFORMATION: probe

<400> SEQUENCE: 25
cacggaccgc acgga                                                  15

<210> SEQ ID NO 26
<211> LENGTH: 15
<212> TYPE: DNA
<213> ORGANISM: Artificial
<220> FEATURE:
<223> OTHER INFORMATION: probe

<400> SEQUENCE: 26
cacggaccac acgga                                                  15

<210> SEQ ID NO 27
<211> LENGTH: 14
<212> TYPE: DNA
<213> ORGANISM: Artificial
<220> FEATURE:
<223> OTHER INFORMATION: probe

<400> SEQUENCE: 27
acacggaccg cacg                                                   14

<210> SEQ ID NO 28
<211> LENGTH: 14
<212> TYPE: DNA
<213> ORGANISM: Artificial
<220> FEATURE:
<223> OTHER INFORMATION: probe

<400> SEQUENCE: 28
acacggacca cacg                                                   14

<210> SEQ ID NO 29
<211> LENGTH: 13
<212> TYPE: DNA
<213> ORGANISM: Artificial
<220> FEATURE:
<223> OTHER INFORMATION: probe

<400> SEQUENCE: 29
tacacggacc gca                                                    13
```

```
<210> SEQ ID NO 30
<211> LENGTH: 13
<212> TYPE: DNA
<213> ORGANISM: Artificial
<220> FEATURE:
<223> OTHER INFORMATION: probe

<400> SEQUENCE: 30
tacacggacc aca                                                        13

<210> SEQ ID NO 31
<211> LENGTH: 18
<212> TYPE: DNA
<213> ORGANISM: Artificial
<220> FEATURE:
<223> OTHER INFORMATION: probe

<400> SEQUENCE: 31
ctgtacacgg accgcacg                                                   18

<210> SEQ ID NO 32
<211> LENGTH: 18
<212> TYPE: DNA
<213> ORGANISM: Artificial
<220> FEATURE:
<223> OTHER INFORMATION: probe

<400> SEQUENCE: 32
ctgtacacgg accacacg                                                   18

<210> SEQ ID NO 33
<211> LENGTH: 21
<212> TYPE: DNA
<213> ORGANISM: Artificial
<220> FEATURE:
<223> OTHER INFORMATION: probe

<400> SEQUENCE: 33
ctgtacacgg accgcacgga g                                               21

<210> SEQ ID NO 34
<211> LENGTH: 21
<212> TYPE: DNA
<213> ORGANISM: Artificial
<220> FEATURE:
<223> OTHER INFORMATION: probe

<400> SEQUENCE: 34
ctgtacacgg accacacgga g                                               21

<210> SEQ ID NO 35
<211> LENGTH: 24
<212> TYPE: DNA
<213> ORGANISM: Artificial
<220> FEATURE:
<223> OTHER INFORMATION: probe

<400> SEQUENCE: 35
gctgtacacg gaccgcacgg agaa                                            24

<210> SEQ ID NO 36
<211> LENGTH: 24
<212> TYPE: DNA
<213> ORGANISM: Artificial
<220> FEATURE:
```

<223> OTHER INFORMATION: probe

<400> SEQUENCE: 36
gctgtacacg gaccacacgg agaa                                          24

<210> SEQ ID NO 37
<211> LENGTH: 15
<212> TYPE: DNA
<213> ORGANISM: Artificial
<220> FEATURE:
<223> OTHER INFORMATION: probe

<400> SEQUENCE: 37
accgcacgga gaagc                                                    15

<210> SEQ ID NO 38
<211> LENGTH: 15
<212> TYPE: DNA
<213> ORGANISM: Artificial
<220> FEATURE:
<223> OTHER INFORMATION: probe

<400> SEQUENCE: 38
accacacgga gaagc                                                    15

<210> SEQ ID NO 39
<211> LENGTH: 21
<212> TYPE: DNA
<213> ORGANISM: Artificial
<220> FEATURE:
<223> OTHER INFORMATION: probe

<400> SEQUENCE: 39
accgcacgga gaagctgagg c                                             21

<210> SEQ ID NO 40
<211> LENGTH: 21
<212> TYPE: DNA
<213> ORGANISM: Artificial
<220> FEATURE:
<223> OTHER INFORMATION: probe

<400> SEQUENCE: 40
accacacgga gaagctgagg c                                             21

<210> SEQ ID NO 41
<211> LENGTH: 24
<212> TYPE: DNA
<213> ORGANISM: Artificial
<220> FEATURE:
<223> OTHER INFORMATION: probe

<400> SEQUENCE: 41
accgcacgga gaagctgagg cctg                                          24

<210> SEQ ID NO 42
<211> LENGTH: 24
<212> TYPE: DNA
<213> ORGANISM: Artificial
<220> FEATURE:
<223> OTHER INFORMATION: probe

<400> SEQUENCE: 42
accacacgga gaagctgagg cctg                                          24

```
<210> SEQ ID NO 43
<211> LENGTH: 22
<212> TYPE: DNA
<213> ORGANISM: Artificial Sequence
<220> FEATURE:
<223> OTHER INFORMATION: primer

<400> SEQUENCE: 43
acacagtctt tgctcccaca aa                                              22

<210> SEQ ID NO 44
<211> LENGTH: 28
<212> TYPE: DNA
<213> ORGANISM: Artificial Sequence
<220> FEATURE:
<223> OTHER INFORMATION: primer

<400> SEQUENCE: 44
acttaagttg gtctttaccc aagagtct                                        28

<210> SEQ ID NO 45
<211> LENGTH: 15
<212> TYPE: DNA
<213> ORGANISM: Artificial Sequence
<220> FEATURE:
<223> OTHER INFORMATION: Normal Probe 10

<400> SEQUENCE: 45
caccaagaga acgga                                                      15

<210> SEQ ID NO 46
<211> LENGTH: 14
<212> TYPE: DNA
<213> ORGANISM: Artificial Sequence
<220> FEATURE:
<223> OTHER INFORMATION: Mutant Probe 10

<400> SEQUENCE: 46
caccaagaga atgg                                                       14

<210> SEQ ID NO 47
<211> LENGTH: 16
<212> TYPE: DNA
<213> ORGANISM: Artificial Sequence
<220> FEATURE:
<223> OTHER INFORMATION: Normal Probe 10a

<400> SEQUENCE: 47
caccaagaga acggag                                                     16

<210> SEQ ID NO 48
<211> LENGTH: 15
<212> TYPE: DNA
<213> ORGANISM: Artificial Sequence
<220> FEATURE:
<223> OTHER INFORMATION: #TGFBI R124C

<400> SEQUENCE: 48
cacggactgc acgga                                                      15

<210> SEQ ID NO 49
<211> LENGTH: 15
<212> TYPE: DNA
<213> ORGANISM: Artificial Sequence
<220> FEATURE:
<223> OTHER INFORMATION: #TGFBI R124L
```

<400> SEQUENCE: 49
cacggacctc acgga    15

<210> SEQ ID NO 50
<211> LENGTH: 15
<212> TYPE: DNA
<213> ORGANISM: Artificial Sequence
<220> FEATURE:
<223> OTHER INFORMATION: #TGFBI R555Q-1

<400> SEQUENCE: 50
accaagagaa cagag    15

<210> SEQ ID NO 51
<211> LENGTH: 34810
<212> TYPE: DNA
<213> ORGANISM: Artificial Sequence
<220> FEATURE:
<223> OTHER INFORMATION: gene sequence

<400> SEQUENCE: 51
gcttgcccgt cggtcgctag ctcgctcggt gcgcgtcgtc ccgctccatg gcgctcttcg    60
tgcggctgct ggctctcgcc ctggctctgg ccctgggccc cgccgcgacc ctggcgggtc    120
ccgccaagtc gccctaccag ctggtgctgc agcacagcag gctccggggc cgccagcacg    180
ggtaagccga gccgcctggc cagggctgcg gaaggtcag gtagtcgggg ctcggagcgc    240
aagccgctgg gggcattgaa ctgggctggg ggcgcagggg acaaagcccg aactaaaaac    300
cttgcagcat ggagcgctcg gacaccagcc ctgcacgcgg tggaaggaga gagggaggga    360
ggtggaggac catggaggga aagcgggagg ccgccgcttt gtagaaggga gtggggaagt    420
ggaccagaga ctttcgacgc aggccaagag cctgagacgg acagcgcttt cagcttctcc    480
tcccagccac tgcagaaagg gggaaatggc aactctttgg ccataatcac cgtgggaggg    540
tgccaagggc aaagcccacc cagcagtaca cctattccaa cccagccagg cccccggcca    600
gcgactccag acaagaacct gggccacaca cggtggcagc atctaaggtg ccccaggctc    660
ctgtgctcct ggccaggccc tgcactcaga cactgctggc acccgacact gctctctggg    720
tacagcaagg gcaatgtggc acttcttgtc ctgcccgatg aagagcagga gaatgcactg    780
ggccctcaca cacactgttc aaatggggaa actgagtcct gagtggttcc actttcccac    840
agtcctgaag tgtgcactgg agccaggatt ggagtctgtc ttaaagtaat agctgggttt    900
gtaaatgtag gacactatca ttgcaggaat tcctttgaga ccctgaagat gtgttggctt    960
taggagacaa actcaagcag aaggtctggt ctgatagtgg ccctaatact gacccaggca    1020
gaggcaggca acatttctac ctcaaaaacc aggccatacc tgcgtcacaa atacccaggc    1080
tttgctgcag cttccagcct acctggttgc accaacttct ttttcataac taggtaaaac    1140
tatatatgag tagaatcttg tagtgactcc tcagaggaag cctaaatacc atcggggtct    1200
ggcgttcaca cccacaagca atgcccaaac ctccaagaga ctgggcagat ctgtgctcaa    1260
atcaaaactc attgttgggg gtgatagagt tgacttcaca ggccctgaaa gtcttggctc    1320
cttgcactag gagtgctctg ggtacgggta caggctgccc cttgtagggc atagttgctc    1380
ttgtttcctc tacttgtggc tttatggtct aggcctttca ggagtttggg gctctggcgg    1440
agagggcctg ctgggagcac atctggccac cctgcagagt gaaatcaaac caggcctggc    1500
tgcaacctca cacccctcct ggaaagagga gaatactggg gatatcctgg ggtctttctg    1560
gaagtgggag aatcagcttt gacttgggca gtgtgcagaa tagagtgagg ggggatgtca    1620

```
gaaagatgag agggatatga ggcctcaaca tcaaaatgca agcacctggc atttttatta    1680
tctctgccca cctctccgtt ggtctctctg cctttcctgc aatgaattg tgttatgttt     1740
gggtgcctca atttgcctag gagggttcta tttcttctgt atcttcgcca ctaagtcagg    1800
agaagatcct tatagcatgc cctgcaacag tgtcacctgt aagggcatct ctctgcacag    1860
ccacagtgaa ggatcctcaa aggtattgag ggctttccat caagagccat ctttacagca    1920
aacctctttc ccttcagagc ccagaagagt gctgaccagc tggaaaacag gttttttc      1980
ttaaatgcag atgctcttga ttatgagttc cagatattag atcaacttcc ccaccatacc    2040
cctgcaggca aagcctctta attagcttcc tgcagcacag ctggaaaggc ctattgtaat    2100
ctgtgatggg cagagtaatc taagaagtca caggagcacc cctgtcccag tagaatctgg    2160
atgcgcaggc acatgaacca tggcaaaatg gttgcaggca cagttgtatt tactctgatc    2220
taactgtccc tgttaatgcc acagggctgc ctggcctggc acacagggct gtggcgcctt    2280
gtgcaaatgg ataacgttgt tctagctcca gcctttcatt caaagtgaaa actgttagaa    2340
agggaaggaa aactttgcta ttttaaggaa ttgtagcgtg ctgcctgata tgaaggaaga    2400
aataacagct gtgccttgct tgtgcgcagc actcgattgc cgcttttgct ttcgacctca    2460
ccacaacaca gtgagatcta ctgttcatgt tcccatttta caggaggtga aactgcagct    2520
tagtgaggta gagagtgact tagttcagac acagaatgct gttgggagag taataactat    2580
gatatggtct cttgactccc agctatatct gtgttgctat agggaagggg aaaaataata    2640
ctgaaagaga agtaaaaata caatcacact tccaaacatc aaccaccaaa aactgaactg    2700
aatttcctga agcacttggt tttcaaatct aagctgaaca tcaatgctgt tattcttgag    2760
gcccagaagc aacttgctca tttcaattaa gcttcagcat gaacttccta tgtacacagc    2820
ccacccacac tccccgatgt gagaaggaga gggtcacagc cgcccccagc ctctgctgct    2880
gccacaagga cagcagcagt ggaaacattc agcaaaggaa tgttggagcc acatccacaa    2940
gagactcact gaagattcgc caaacgccta cggaaagtgg cagggaattc attgacagta    3000
attgtttcct gcttgatcag attgaagagc ttctgggatt ctgtaacaat aaataggacc    3060
gggggctgga gtatggccag caaggactct tcaggggtta ttcagggact gtctaacctg    3120
tgaatcctag gcagcaaaca gaaaccaggt attcagaaat ctggaggatt tggtcaggcc    3180
cagctaggac tagggaggca tgggcctctg ctggctgtgg tcccttctcc agccttcact    3240
tctcttgtcc ctagatcctt acatggattc attaatgctc attgtccctc ctgggcccac    3300
tcactttcac ctgttgaaca aaaaactggc caagaggtga cagtcatatc accgcagaag    3360
agacagggca gagaaatgaa ggggcagaat ggactcccac ccaaaagcct gactctgaat    3420
atttgagaat tgttcaagtt cctgcagagg aatcatgatg gggacagtag gtgtagtttt    3480
tactgcaata ttggtgtctt cttaacaaat acgctgcaca tcaagtgatg tctgtggatg    3540
gcattcttaa agtaacaggg aaattgatgt taaagaaata cttcatcctt tgggtgatac    3600
ctgaagttct ctgagcttgg aggtcttgtg aaagccctca gtattgtttg ttttatttgc    3660
tttcctctga cttgtgattc agtcagatgc atgcctgcct ctggctcagg aagatcaacc    3720
ctctcctgac tgaccacgcc tctcctgact gaccacgtag cacagcagct tccttccct    3780
agggctcct aatgaagctt tcacaatcac ctggcctgag cacagtttgg gtcaggactt     3840
ggtatacttg aaaaaaacat gcaaaaccaa aatcctgtgg ttctggaaaa ggcttcttag    3900
cagaaccccc agacatttac actctgcttt ttcacagggt ccctgaggat tctttggatc    3960
```

```
tgggtagttt ggggagcagt attttcaaca agttcatttc gtgctccttc tacaccctgc    4020
ctggatgcta ggccccatct agaatgtgaa caacagaaca aggcagaaca cttgtcctca    4080
aggttctgtt gagtgttaga tgcagagaag agacaccccc cacctccccg catcacttac    4140
aggaattctg tttggaaccc aacatcaaat aaggaccgta tccactgtca gaggatggga    4200
agcagcatgt catctgggac attggagaaa ggctcctggg ggaagtggga cttgagctgt    4260
gatctaagta atgaacaact gagagttaaa tgggagagca tccccctatca gggtcctgag    4320 agcaaccagc catggtttaa accagctata aagcctcggg tttataggat agacagtaac    4380
aatggcttgt ctttgggagc caagcagctg gtccaggcat gcagagcatg tctgtatgga    4440
gagctgcctg agagatgctt tgtttacac ttatcaattg cccatgtcaa agaaggatat    4500
gtacatgaag ttcatcagt atgtaagaga gattttaaca attttttgcag gggaagcttt    4560 catgggggct gatgggaatc taggtaaaca gaaccaaagt ctaaacccaa gatatcccca    4620
gtaccaagac tgaaatgact ctctcctcta tctctagaaa gttccagtga cccaaggagg    4680
caaacacgat gggagtcatt aaagtggggt ggacgtgctg atcatcttcc taattctgct    4740
gcttttgttt tcagccccaa cgtgtgtgct gtgcagaagg ttattggcac taataggaag    4800
tacttcacca actgcaagca gtggtaccaa aggaaaatct gtggcaaatc aacgtgagta    4860
tctgtaacca gccaggagac caagctgtat gcacgctggc tgcagttccc cagggcctgg    4920
gccagccttc tagaaggtca ggttgcctaa aaagccatga agatgcatgt gcgaacatgt    4980
ctgggacctg cgtgctaggg agtggcattt ttaggaagct ggccaatttt gttttgcatt    5040
tttaaggctg ctgacaagac ttggagacat ttttcagggc tggtttgggt ttgcaagaaa    5100
catgaaacac tgcgtgtgtg tgtgtgtgtg tgtgtttctc aatcctcata aaataataca    5160
gatatgcagt ggagaagcca ccagcatgtg actctggaaa agaaagccca ttggtgaatc    5220
tgtactaaag aatgccatcc ctatcttaca gtcctaaggt aaacaccca aaaagactta    5280 gagcactaaa catatgcaga ttatgagaca gcatagcata taatatttgc acagacttcc    5340
tcattcaaac cctagctcta cctgggccag tcgattcatc tttagaaccc tccattgctt    5400
tacctgaaaa gttcgtataa caaaaggacc caccttatgg ggttgttaca aggattgaat    5460
gaaataatgt acataagaga ctgaatatgg tgcccagcat atatcagtgc tcaataaatg    5520
ctagctacta ttattattat caccctagat ttgcaaatct agaccacaca agcagaagta    5580
agagtgccaa cggggtgtgg accagtgtgg ttacaatagg gcttgttgat gtctgtttca    5640
gcaaggaggg aggcagcttt tacccccactg cccagctccc tggtggaatc aggtgcatgt    5700
tctaacaatt ctggggaaac ctaatctgtt ttggcactgt caacagatct caaagctggc    5760
tgtctcctat agctaggaag atgtgtatga caaatctcct gagccacttg tgaaggcctg    5820
accttcctcc tgtctccata cataatggga tgattaagaa actctaagcc actctcttaa    5880
gcacttttca atgttaggga ttttttaagtt tattgttgtg acattgcttt tgagcagaca    5940
tctcctccaa tttaatagcc aactgaaaga agagaaaatg ctctttcctt aaactgtatg    6000
tggaaataaa tattccaatg tgtgaccctg attatgttag gcaattagca atcctaatat    6060
gaattgaggg aagttgggat tcatggcaca gctggggaga taccagcagt ccctgggagc    6120
ctgtccaggg caggtccatg gcagcttgct ccatgcctga ttgacagccc agcctgcaag    6180
ctaaaagttg agtgagctag gaggacacac tgccaagatt cagctaacag acacccagcg    6240
atattcttgc tgctatgaac aaaaggagac tatgcaaatt atacaccacc cattcttcca    6300
ggatgcctga cttaaaaaat aagaaaaaag atgggccggg cacagtggct cacgcctgta    6360
```

```
atcccaacac tttgggaggc cgaggtgggc ggatcacaag gtcaggagac agagaccatc   6420
ctggctaaca tggtgaaacc ccgtctctac taaaaaaata caaaaatatt agcgggcgtg   6480
gtggcgggca cctgtagtcc cagctactcg ggaggctgag gcaggagaat ggcgtgaacc   6540
tgggaggcgg agcttgcagt gagccaagat cgtgccactg cagtccagcc tgggtgacag   6600
agtgagacac cgtctcaaaa aaaaaaaaa aaaagaaaa gaaacctt agtactgatt   6660 gattttttcc catgtgtgta tattatctac tcaaattaac aattaattac ttaattaaac   6720
acaaagccag gcctcaccta attgcttctt ggaaggtgac cagagtgcta gtgccaagca   6780
aacaactctt ctatatctca agagccctgg gcttcagagg gccatctttt ttgttaattc   6840
aagtttctct gaaaatggag acccgtttat gatgacaagc tggctacagg gtagcatctg   6900
ccacactgtt tcgggggtgc cgctgggctg aagcatttgc ccagctagtt aacaatagct   6960
cgataacatt ccctatcagt gtccaggctg agaatactgt cagtgatgag tcgccttggc   7020
tcttgtacct gtatctttgt gtgccaggac aaggcacaag caacagagct gtgtgttgcc   7080
aaaatgttcc tgatgagcag gtcaacccct cggggggcagg tttggatatg ataatgtggt   7140
gatgtggtgg cgcagctccc ttacccagtg agcacaaggg gagtcctcta ggaaaaggaa   7200
gaaatgtctg gatgaggtgg ggagatgggg ttcagagtgg actcaggcaa agcccgatgc   7260
ccagtcccag ctgttggcct agtctcacaa agccagaagg atatgacatt tacattcaac   7320
tcttgaattt gtggccactg cttgggcaa cttcaaagag agaaatgaa gatagaaaaa   7380 tattatttga tataaaactt ctaggacaag agaggcccctt cctggaacat tacatgtagt   7440
attaggaagg tggagctgcc ctggaaaaga tccagagaac tcagagagag gaagaggtgg   7500
aacccatctc tgttcttgta gagagctcag taagagtggc ttggcagggc tcctgtgtac   7560
ctgagaccaa gaccagtgag gaggctactg tctgaccacc atacggtcag aattcagtgc   7620
catgggtggt caggtgggaa ggggagagga ctgtgctggc tggagttgat gttatcctgg   7680
ggaaagtagg tccctagatg cctttagttg agtgaggagc agactgggaa atgggagcac   7740
agtagtggtt ggggcaaaaa ggactgtctc tgcatgaggt ccataggcag ttggaatttt   7800
ctcagcaaga ctccagagaa ggaggctgga gcagaggtgt atgttgggat gaaaaggagt   7860
aaagtatcat gggggaggag gcagctcagg ttgtcaaggg tcaagaaacc agaaggagaa   7920
tttcaccttg gaagcagaca acgggtacca agcatacagg ggaatacttt gtggtgagag   7980
gtcacacaga gatacaggag ccgacctggt gagacaggag cctggagcca cctgcctgct   8040
tttgtgaggc cccagactcc actgctatca tcaggtgaag ctctgttgcc tgcacacaaa   8100
agcttttctg catttacaaa gagagaaggg cctgagtttc tggtgcaatg cgtcaagctg   8160
acatatggac tttattacag gaagtggtta ccagtgggtc cctatttagt ggctgttatt   8220 gtgaattta ttgttcggaa attcacttta gcatttattt cagatcctaa atagcaccgg   8280
agtgatacaa tggctaatca aacaaagagg gctgtgggga gcagacagtc agcatccccc   8340 tctgtgatttt caggccctgg tttgattagt agccataaaa ttttttacgt gtggcacttt   8400
gagcaaaggt gcaggaaatt gtggtcagga agcctggctg cctctcgaca ggcttccttt   8460
gtgctagccc cagggagagg aggcctattt aacagccaag tccaagttga catcatggga   8520
ctggaatagt catagcagga gctcagacat cataaacgtg gcatagggag ggctggtgga   8580
ggagctagcg ggtatgggtg gcagctattc attccaaaag tcttgaaatt gtttcacgag   8640
caacacattt cacaagtgcg aagcccttct ctggagccaa gatgagctgg cagagcactc   8700
```

```
ctgtttctct agtagcaagt gttcctttgc ccaggggcaa aaatattaat actccttcag    8760
cactgcatta atgcttaaag atttaacttt taaagagatc agctggtgca tggtcgagct    8820 ttttccatcag ctggcagggc tttttcagta ggtgtccttc tgggcagggc actggggaca   8880
gctgacgtga aggtgaagaa gagctgtcgt tttcctccct tatatcccac aaccttggtc    8940
ccaagaggaa aaaaagaag atggtgagaa gtcatccaag cagaccccag acccatacta     9000
gtgcctcctt tcctgtttca tatccctgtg cagccagctg ggatctcttg aataatctgc    9060
tctgggggca ctgagattgg acatacacca aacagcggag atcgaccaaa cgcctctgtt    9120
gggcagtgtt tcctgagggt tctgtcccat tctgtaaact aggaggctga ctagctgaca    9180
aggaatttta ttctgttggg tatttacatg aacctatgtg ccacctgggg taagaccctg    9240
tggtaggtag aaacatgact tcccaaaaat gtccacatcc taatctctaa ttctgtaaat    9300 atattcccctt actggaaaaa gagactttgc aggtgtgatt aaattaagga tcataagagg   9360
gagagattat ccaggattat ttgatgagtc taatataatc atcagggtac ttaaaagagg    9420
gaggcaggct gtgcctggtg gttcacgcct ttaatcccag cactttggga gactgaggcg    9480
agcgggtcac gaggacagga gttggagacc agcctgacca acatggtgaa actcccctc     9540 tagtaaaaaa aaaatacaa aaattagcca ggcatggtgg tacacacctg taatcccagc    9600
tactcaggag gctgaggcgg gagaattgct tgaacccagg aggcagaggt tgtggtgagc    9660
tgagatcgca ccactgccct ccagcctggg caacagagca agactccatc tcaaaaaaaa   9720
aaaaagaggg aggcagtggg atcagagtca gagaaggcaa cgtgatgatg aaagctgaca    9780
tttgagtgat gcaaccacaa gccaaggaat gcaggcagct tctcaaagct ggaaaggacg    9840
agcaatggat tcttccctac agcctctgtg aggaatgcag cctttgattt taaccccata    9900
aggccgattt ctgactctag cctctggaat tgtaagataa tttgcatgat ctcaagccac    9960
taaatttgtg gtaatttgtc acagaaagca atgggaagcc aacacaggcc ttatttgttg   10020
acttatagat gcatttttct ttatttcaat gtacttttat caatggtctc atgtaggta    10080 ttgctttcaa tgaagatatt aacatagttt caactttaag gtttatatct ggagtttctt   10140
tagaagcttc acaactgacc acttagtaaa cagtaagcat ctgttaagtg cttctcatat   10200
gtaagttcat tcaattctca caatcacact ataagataaa tatgattatt agcccattta   10260
cagatgagga gacaggctca aaagacttt atgcaacctg gtcaaagtca ttcactggta    10320
agctgaggag gtctgtccac ttcctttgc tgccccagg gggtatcaag cctggcagtt     10380
agtgtcagcg acttaggagg tgaacaagtg agcaggcctg taggacctgg ctaaactgcc   10440
ccaggtctct gtctacagcc tcaaacctgt ggctgtgggt cccagagaca aggcctcctc   10500
agcatcagaa aaggatgcct ttgtctcagg gtcatcaacc ttctccaggt tgctcacccc   10560
ctgctgtaaa ggggatcccc aagaccgctc atcagacaag gagcttggga actgaggaga   10620
cacagtcagc ctccaggagt gcccaaaatg ccctcacatg ctgcatacag attgccacaa   10680
ataaagtaca tccacattct gaagactctg tcctcatcac caaccaggct ggcccctggt   10740
gagggctgta gtggttgagg cctttgttgg tagacagtag gttaaagcaa gccatgattt   10800
tctattggga ggcttcagaa tcagctcagc tgtgttccca agaccaggag ggcagaaagc   10860
aaaccatccc aggcaagcag tccatgggcc atgtcagatg tctagacgtt atgggtctgt   10920
gtttgctctg ccattcctct cggaaactat gatgccctgt atggtttacc ttcagtcaca   10980
ggtgactggc ctacagggcc attccttgtt ccaacgactt ctcgagtata attaatcccc   11040
aggcatttac ggccagagca gccggccaaa tccgtgaagt gcagtggttg ttttaaatta   11100
```

```
tattaacttc ttggaaactt attttaggga gagaaaactc agtacttctc tctatccaat    11160
cttgagtaaa aatgttagaa gggactggtg gagagcctcc cagacatccc tacacataga    11220 ctttggttg acattatctc tttgcaccttt ccttgaaact ttcttctaaa ttaggtgcct     11280
tccctaattt aggcaccttc ccagtactag tctgtgacct gttaggaacc aggccacaca    11340
gcaggagttg agtggcaggg agtgagcatt attgcctgag ctccgcctcc tgtcagatca    11400
gcagtggcat tagattctca tagcagtccg aatactattg tgaactgtgc gtgtaaggga    11460
tctagcttgt gcattcctta tgagaatcta atgcccgatg gtctgagatg aagagtttc     11520 ataccaaaac cacccctttcc ccctgccacc atctggggaa atattgtcta ccacgaaact   11580
gatccctggt gccaaaaagg ttggggaccg ctgtcctaag ggatctgctt tttctgacct    11640
gaggtttttc tttattagac tgtatctggc tgaggagaag cctgaagcct ttaatcggaa    11700
cagctttggc tgatgagatt agattcagaa accaacagat tggtcttttc tatgcaggga   11760
agcctaggaa ctgggggggct atggctggga agcccctat tgtttccatc ctttcctatg    11820
ttcatcctgg aggaatggca tcagacccat gcctctgtga ttgctcccag cccatccaac   11880
cacagcatct atgttctgcc tgggaccagg gccagggagc atggcacact gagctgagta    11940
taaggagagt ggagcaggcc actgccagcc cagaaaattt tggtcaaagt tgcctgaaat    12000
cttctcagcc ttcgattcac agctgctctc tgctgctctg gggccatgca gaccagttca    12060
gaaaagagtt aatttgttgg ggcagttgga ggcaggtgga ctgccagctt tgacaccttc    12120
ccagcccaca ggctgctgca ctggggctga aggcgtggct aaccctgca cacctagaga    12180 gtgacagaga tgccagactg ggcagcagga aggcaagagg attaagagag agcttcctgg   12240
ctgaaagcca cactcggtta accaggaaaa agcccttggc acgagaagac tcagtggcct   12300
gagggactga gccttggttg ttgggcatgt gctgcataag ccatccatgt gtgacagtag   12360
agtgtagtcc agccactgtg ggacatgggt gctgaaagac cacatggaga ggaacagtga   12420
gtgctgacaa gggctagcct tgatcacttt ggagacaccc cctgtgtctt ctagatgtca   12480
gactttccaa atctgtctgc tatcctccaa acgtgcattt tcaagagcaa tggaaaaagg   12540
attggacttg atggaatgca gcaagagtcc taggtctgtt actacctacc tatgacctta   12600
agaaactcct tcacccctca gaaccctttac agctttcttt ctgattctat cctgagttac   12660
tctactccaa gctgagactt ttctgcttag atctatccct tcctcctaaa cccccaacct   12720
ccatttctcc tggtgtctttt ctttacacac ccctcagcat acacacacac ctagccacag   12780
gaaccaatga gttaatattt gaggagttgg ttttctttttg tcctcaatga atcctggtg    12840 aggccacttg agctgttcag ctcccttgcg gtattttggg gatggaactc agaagccaac   12900
aatatagaaa aagagtctttt ggccagcttt cccaggggct ccatgccata gagagtactg    12960
cacccgtgtg cacaggggc cctgacatga ggactttgag gataacacta ttcctccaac     13020
tctgcttcag catctccatg gattttcaca cagacacttt aggaaagaaa ctaagtttgg    13080
ggggacttga cctaatccca catcacagcc ccagtaatac agccctggaa tttatcacag    13140
aaagcctaga atcccatgca tatcccatgc atatgcatcc ctagtcctat gggttcaagg    13200
cttggagctc tccctggatt tagctgggaa aagttggcag acagttcttc tctgtcttct     13260
agaaatatgg actagaatcg tgagtgtgag attgcaagta acttttaaaa tcatctagtt    13320
taacttcacc ccatttcata gaccaagaaa ctgagaccag agagagaaat ggactttcaa    13380
gttcaccctg ctagttactg atggatcaca agtcaaatct cctgattcta gcactgtttc    13440
```

```
tcttacacca caccacctttt gaaagtgtgt caatcaaatc ttactttagt tgcagaggat    13500
gactttagtt tctgaagata aaattgtgag tcaatcaaga tgagtcccaa gacaatagcc    13560
tgtttagccc ttataagttc agggatgaaa ggttagaaag aaacaggatg aaggaggac     13620 tggagaaaaa aacaaaagag gaaggaagga ggaggaagca aacaggaaaa aaaaagaatg    13680
tgcatagctt gtcactcctc agtcatttcc tgggagccca tttctagcaa agtgacagct    13740
gcaactccct ggccacctga gcatcttagc tgatctgtct ctgaaacacc cctggagaa     13800 cagatgaatc aggcttcatc ttcgcttaac taagtcttcc ctgagacgac tccatttaaa    13860
tgaacaagag caggatttcc tgggcacact gagagcacct tccagaggcc cctccagagc    13920
cctaaagcct gtatttcttc cagtcggcct gtttctttcc tggtgatgtc attaaacgcc    13980
ctttgagagt cccacagtga gcagttctgc ggtaaaaccc gctgcaatta aagtctgagt    14040
cctttcctgt ctcaaagggc atattcatat agaagaaagg aaaaggaagg actggctgtt    14100
tgcatttggt tccaggcctg ttgagtagag gtcgtgctca ctccaccgaa ggtacagggt    14160
agccttcagc agaacctggg gatttggttt taagcaagtc tttcttaggt gtgggctttc    14220
agaacacttc cttccttgca atattatttg aaattctcag tgttttagcc gtccccagaa    14280
tattggttcg ttaaagctgt gtatttcaga tctccagaca gtggtcactg tttgtatatt    14340
ttcaatttca aaccagaaaa caaaagttct tattgattac tttttttatt taaaaaataa    14400
aaagtaagta tcttcgtaag aggagctttg ttttaatttt aaagtttaaa atttgattgt    14460
gaagacagag aaaaacttga tgattgtaga tatattcccc tctttggcta ttcaatcaga    14520
gaactagaaa atcatgagag atttaatgac cactgcctga tacacatatg tgttttacag    14580
atgaggaaac tgagacccag agagatgatg aaattggctg aggatggccc agctggtcag    14640
tgaaagactc agagccagag ctggtgcagg gctctttcta ttccttcctg ttccctttca    14700
ggaacactca ccatcggctt tcctgtgaat aatgttgaga taaaatcctt ggtgcattat    14760
gttttctagt cacaacattg actaggctgc cagagtcctc tgttctccca gttggttggc    14820
tgtaggtgtt ggcagccgcc aggagcattc tacagaacag aggaggagtg agactctcct    14880
tgctcaggaa aggcagacct atgacttagc aaataactcc taagaggaga gtgtttcacc    14940
caccattcct cttccttggc tgtggaggca acttagtgga gaggggccag atgacctgtg    15000
aggaacagtg aagccctgcc taacacaatg tatggttgtc ttgttacaga gtcatcagct    15060
acgagtgctg tcctggatat gaaaaggtcc ctggggagaa gggctgtcca gcaggtgaat    15120
gaatcctccg ggccttgcct gttggtgtgg gtggaaggga atggtgggag agaggagtac    15180
ccacataaaa ggcagcagag tgtgaatggg ggcagtggca caaggacatg gcattctccc    15240
cacgtgccca ctggcccag gctctatgcg aggggctgag gaatggaagc tggaaacagc    15300
gcatttcctg agctgctcct cctggcctcc ttaccacact ggtggagtag actccaactg    15360
tggcctgtcc atgcccttcc cagcaggcac aggctcaggc tcaggctctt ggcctctgcc    15420
tctggctggg agtgattcta aacacatcca gcagggtcag cctgatagcc catcagtttc    15480
cgatcagctc tgctagagag ccgatgggat gtgggaggag ggggtcactg gtgggctggc    15540
aaccccaagc catccccatc tccctctgtg tctaaacttg gccctttgga gttcggtagg    15600
gagaagagcc ataggccagg tgggctcacc cagagtcagc agagagtccc acaaatggtt    15660
gcactgggcg aaagacagca tggcacctgt gaatttttatt agagcttttc ttttagtgct    15720
acacacaagt gactgtacag gggagttagt attttgtttt aatttgaaa tagagtcatc    15780 ttttggtatc tgcgggggat tgattctagg acccattcta ggatgccata tcctcagatg    15840
```

```
ttcaagtccc tgatataaag tggtatagta tttgcatgta atctatgcat attcttccat   15900
gtactttaaa tcatctcaag attacttata ataccaaata taatgtaaat cctatgtaag   15960
tagttgttat accctctttt aaattttgt attatctttt attgtatttc aaaaaatatt    16020
tttggtccat gtttagttga atctgtgggt gaagaaccca cagatacgaa gggccaactg   16080
tattggctat tttttagtt aagaatgtga gactgaggcc aggcgcagtg gctcatgcct    16140
ttgattccag cactttggga ggccaagagg ggacgatcac ctgagccaag aattcgagac   16200
cagcagcccg tgcaacatag tgagaccttg tctcttaaag attgtgagac tgggctgggc   16260
acggtggctc acgcctgtaa tcctagcact tgggaggcc aaggcaggtg gatcaactga    16320
ggtcaggagt ttgagatcag cctggctaac atagtgaaac tctgtctcta ctaaaaatac   16380
aaaaaaatta gctgggtgtg gtggtgggcg cctataatcc cagctactca ggaggctgag   16440
gcaggagaat cgcttgtatc caggaggcgg aggttgcagt gagctgagat agggccgttg   16500
cactccagcc tgggcaagaa gagcaaaact ccatctcaaa aataaataaa taaataaata   16560
aataaatcat gagactgaga cataacagga aggagggcaa tttggttggt tccaaggttc   16620
ctagagtatg tgatgggaga ggttggtgcg ggtggggcca tggaggtact gactcaagtg   16680
gagggacagg tggggaaatg ggatgggaaa agaagattga ccttagaagg ggagctcaac   16740
ctctgaaccc taatttcaga cccttcaaaa tgaatattaa gctcattttg gtctaagaaa   16800
caaaaaacaa atgaacatga aactcatttt ggtcttataa ggtctgagaa accccttcta   16860
aacttcaagc tgctttaaga aataacattt tattacctgc aaatacacac agtactttgg   16920
agatttataa tagtctctta ttctaataga agccattagg gaaccagttt caataaacag   16980
gtaaatctgt aagactagtt tgtaattagg atatctgttt ccagtgtcca ttcctgcctc   17040
tgttatctaa atgtctggga acaagagctg tgctctgctg tgtttaaaat gattaaaaat   17100
caccaattag ttgagttcac gtagacaggc atttgactta ttgagttgtt ttaagaagac   17160
tataacaagc cttaagcccc ccagaaacag cctgtctttg ggctttccca catgcctcct   17220
cgtcctctcc acctgtagat gtaccgtgct ctctgtcaga gaagggaggg tgtggttggg   17280
ctggacccc agaggccatc cctccttctg tcttctgctc ctgcagccct accactctca    17340
aaccttacg agaccctggg agtcgttgga tccaccacca ctcagctgta cacggaccgc    17400
acggagaagc tgaggcctga gatggagggg cccggcagct tcaccatctt cgcccctagc   17460
aacgaggcct gggcctcctt gccagctgtg agatgacctc cgtctgcccg ggggactctt   17520
atggggaact gccttacttc cccgaggggt gggcatgatg aatgggagtc tgcagtcatt   17580
tcctactgtt tcaggaagct ttctccttaa ccccttagaa aaggctgtgg aacttgagct   17640
aaaatatgtc ttaccaggtt gcgtctaatg ccccccgttc cctactgggc agaaagactt   17700
gggtgcttcc tgaggaggga tccttggcag aagagaggcc tgggctcacg agggctgaga   17760
acatgtttcc cagagttgca aggacccatc tcttaaacac agagtctgca gcccctaact   17820
gacaccctgt ccttcctcct aggaagtgct ggactccctg gtcagcaatg tcaacattga   17880
gctgctcaat gccctccgct accatatggt gggcaggcga gtcctgactg atgagctgaa   17940
acacggcatg accctcacct ctatgtacca gaattccaac atccagatcc accactatcc   18000
taatgggggta ggggatcccc agccatactg catggccctt ggtgcataat gaacccattt   18060
ctgttccatg tgtgggctgg tttctgggt ttaagctgta gacaacccac cctctttgtg    18120
cctgcttctc cttgggccct ctattccaca gcttgtggaa cccacatttt gctactgtgt   18180
```

```
ttgaaaacac tgttttctcc tcccggggct ttgggactat gcctctgttg tgttgactgc    18240
tcatccttgc tgcttctctg ggcagattgt aactgtgaac tgtgcccggc tgctgaaagc    18300
cgaccaccat gcaaccaacg gggtggtgca cctcatcgat aaggtcatct ccaccatcac    18360
caacaacatc cagcagatca ttgagatcga ggacaccttt gagacccttc gggtaaggga    18420
ctgccctggg tggaggccca ggcttgggac acattgcctc caagagggg cctagcagga    18480 actcttctgc aggagaggta gaggatggct cctgtagggg aacatagagc aggttcccct    18540
gaatgccctt gaacatggag aattcattga ccagacattc agcttgacct aacctgtgaa    18600
attctccatc ttctttataa agtgttccct tccttgcctc ccctggaaag gtcagtggtg    18660
tgtggctgca gcagcacagt gtcctctgag ccctggacct gcactgtggc ttccagaggt    18720
ggcagttccc acatgggta ctagaataaa tggcctatca ggctgtgtgt gctttgggat    18780
cacatgtccc caccctagga ccctggttcc aaccatacgc atgttctctt ggagcccaga    18840
acagcagaga agccaccagt gtggacacag aagtcaaggg tctgatttcc agcctggctt    18900
ctgactgctc tggggccgca ggaatacggt tccttccccc atgcccagca ggcatttgtc    18960
ttacaactgg aggggaaggc atgttcctct tggcaaggac tgctcaggag gaagtggagg    19020
caggctgccc tgtcagggtt tttgccttga ttcaaggaga acttcctaac cacaaaggat    19080
acaagtggga gtgaggcgga ccctccctag agatctccaa cacagagaga caaacacgct    19140
ggggctggct ggcactgaca ggcctcgcag gtgtggatgg ctgttagctg ggagcttcgc    19200
tgtctaagct cctctcccat gcttttcttc tgggttgctc gaaggacggg ggtctgcaag    19260
aaaatgatgt tccacatag ttggcagcac gtgaacagca attgatccct ttgcatcacc    19320
tcctcttact gtttagattt ggtaaatatt tcttccttcc ctcttctgac cctccatttt    19380
gccgatcttt ccttcttata acacatactt actaggtacc tgctacttcc cgggtgggcc    19440
tatgtgccag gagtatagag gtgaacaagg aaggcaaagt tctattctca gtagagctaa    19500
tactctatct ggagagagac aacaaacaaa tcaacaaggt agccagggc tgtgataatt    19560 tatgtcaagt gggcaggtaa atcgggagtg acagtagtgc agggaggatt ggaaagtcag    19620
ggagttctct ctggaggagg tggcttttga tctgcagcct aaaggatgag aatgggtcca    19680
ttatacaaaa tgctggggca agagcacacc cagtagaggg gagagtaata gcaaaggctc    19740
agggcaggaa gggcaaggga gaggccagtg ggtgaggtca catgtgaagg gcatacaatg    19800
ggcaaagaca aggccagagt ggccaggccc aatcctccag gacttgcaga cctgggaaag    19860
agtgcatctc catcctggga gcagcaggaa accactcagg cctttagaag atccttctgg    19920
cagctgtgta gagaatgggt ggtgtgatcc ttccatgcat gggctcatgt acgtgattac    19980
cagtaactgt cgagtgacag tgtgaggagg ctgcaagcc atgagtgtag gcacagcaga    20040
cagactcacc tttgtctggc ggtgagatgg ggtgggaagt gtgccaagtt gacctcccaa    20100
agaaatgata ttttagtgga agaatgaata gaatcagaga agcaaagtaa gagggaagag    20160
cagagaggac agcagggaca aggacttggg ggcaggaaga ggaaaggcag gttaaggaca    20220
tgaaagatgg ccaggctggc tggagctcag gcccagcaag gcccctgggg ggccatggtc    20280
atgggtgagc ttgggtttgg cttctgtttt cgtcttgggc ttctgtgaaa gcctcgagcc    20340
cttgcgggga accagtgaag ctgtgtgtgc atcttctgtg gggagtgcca gagtcttcag    20400
ggagcactcc atcttctctc ctccccacag gctgctgtgg ctgcatcagg gctcaacacg    20460
atgcttgaag gtaacggcca gtacacgctt ttggccccga ccaatgaggc cttcgagaag    20520
atccctagtg agactttgaa ccgtatcctg ggcgacccag aagccctgag aggtgagcat    20580
```

```
cctttggctc ctgctgctgc ctcatttgtg cagctagatt gagcccaaga cctgctctgg    20640
tccaagatga acataccacc tgccatgagg tgaccctcag gatatccact gcagccatgg    20700
gctggggtca tcctgtcctg ttgcttcagc taaccgtgtc tctagcagcc acactactct    20760
gagggctgac tacagaatcc agcagctttt gtctgggaga gctggactga agagaggcat    20820
agctggagac ccatagctgg ccctggccag aaacagggag agtgaaaggc tggaatagcc    20880
aaggccagag caaggctaat aggtagagca acagcttaca ggtgtggggg tggcagatac    20940
tggcacccTT gaaatggatt cctcatgccc acgcttcact attcttctct gtggctaggg    21000
gatttatgga taaaccaaaa ttacagttaa aaaccagcca taggccaggc acagtgactc    21060
acgcctttaa tatcagcact tgggaggac aaggtgggcg gatcacctga gatctggaat    21120
ttgagaccag cctggccaac atggcgaaac cccatctcta ctaaaaatac aaaaattagc    21180
tgggcatggt ggtgggcacc tgtaatccca gttactcagg ggctgaggca ggagaaccac    21240
ttgaacccag gaggtggagg ttgcagtgag ccaagcttgc accactgcac tccagcctgg    21300
gtgacacagc gacactccgt ctcaagaaaa aaaaaaaaa aaacagttat agtagtcaac    21360
ttttgactct ccatttcaga tttcgtcatg ccctcctcaa tgagctgcta agttaggcag    21420
tgcattgatt attgctgcag gagagggaag gaaggagcta acgtgttttc acatgttttc    21480
cttttggaga tgagaaagga ggactctgcc ttcccctac cctgcccctt tctactccag    21540
gacctctgaa aggccatgag cacaaagctg ctgcctgagt cccctgaaat gcagggtacg    21600
ccccaggtct ctgatgtacc ccaccacact tttcctctca acatattcc aggatcactt    21660 gatttctttt gaatctattt aaacccaccg tgtcaatgtg ctatataaaa tgtctaatgc    21720
atttcagaca ccctatacat ctatacattt aaagtgttct ccttctatct gtgcagggat    21780
gggaaagggc atatttctga agcacagat gggaagacgg gatttgttcc gtgtccaggt    21840
gattatggta cctctatgcg cctggccggc actggggaca gaggccatga aaatgaatac    21900
agcacagcct ttgcctccaa gaaacttaag acctagtaga aatggcaggc tttaaaacag    21960
gttgttggga tctgatttgg tgagtgcaat gacagagata ctcacagcac aaaatgggga    22020
atgagggcgg gcattgggac acacatagcc ttaaggggcc caaaggcttt tagaactgta    22080
ttccctatta aaacatgatt tgcacagagc acattctttg cttggagac ctcagaactc    22140 cttactatag gccgggcatg gttataatcc cagcactttg ggaagccaag gcgggcagat    22200
cacttgaggc tgagagttca agaccagcct ggccaacatg gtaaaacccc gtctctacta    22260
aaaatacaaa aattagctgg gtgtggtggt ggccacctgt aatcccagct actcaggagg    22320
ctgaggtagg agaatcactt gaacctggga ggcagaagtt gcaataagcc cagatcatgc    22380
cactgcactc cagcctgggc aacaaagcta gactctctca aaagaaaaaa acaaaacaaa    22440
acaaaacaaa acaaaaaaaa ctccttatta taaactgtaa gaaaaaaaag gcccctactt    22500
cgtccctttt gcaaatctgc ctttcctac tcactaacca gctggttcag agcaaggaca    22560
ctctgtttgg tgccatcgct gcagactgga aggaagaggt ccttgcccca cacccaacag    22620
tctcctgctg ttaccggcag gttggcaggc aggcaggcga gaagcagcca gggctggtgg    22680
tgtgtccagt ttgaagacta gtttccagcc ctggccctgc tcaccctcca agtggccctg    22740
gcaggttcct ctaccacatc gtggacttca ccttccttct ctaagaagct caatccccaa    22800
ggcctcattc ccataggcct tctcacccTT ttctttccc tctggctgaa tgtgccagc    22860 acgggcttcc aaggccatca actcgtctgc agcagcccca tgccttgcag ggcctcagag    22920
```

```
cttcctcctg cctatgacag tgtggttttg gttcccacac ttgggatcag attgaaactc  22980
gcctccgtgg tgagaatatg ggacatagag cctcggtgac cttggtgagc agcagtccag  23040
gccacctgct cagcctgggg ttggggggggg ctcctcctcc ttgactggtc cttgcatttg  23100
cctccatcca gcctgtctgg gctctccgag gcaatggaga ccagcaggag tcacgatggg  23160
tcaggagccc cctttgggcc tcagccctgc cctgcccct  aaagtagcac ttggataagc  23220
aaataaatta ttatacttac tatttatggg tgtggtgaat gggatggcaa aggccaagtc  23280
ttactgatca ccaaacctta agatatatcc tggcagctag tagacccttg ggctaaatga  23340
acagaaaact ggacaaataa agtgtacaca aataactcaa agctgtcatt tgtacacttt  23400
tcgtcttttc ctactacagt ttacattttt ataaaggtga gtagatttct aaaatcccgt  23460
ggtaggctct cttgagtttt tcttgtatcc ctgaagttca gctacaaata agctaatcac  23520
taacatttgt tgagcattta ctctgttgtc aggccccgtg ccgagtgctt taggttcaga  23580
atttcatgtc atcccacag  cagccctagg agatgaatgc aattcttatg tccacttgac  23640
tgataaggaa gttgaggttc aaagaggcta aatgactctc ccagggtccc acagctgaaa  23700
agtggccaca gggccccagc tggttttcta gggcagcagg cagaaggcga ggaggatctg  23760
ggccctgtgg tgcccagcc tcatctgagg gtcctcatct gagagaacag gatcctcaca  23820
gcatgggcag gctgcaagtg gtccctgagg ttatcgtgga gtggaccctg acttgacctg  23880
agtctgtttg gaccccagac ctgctgaaca accacatctt gaagtcagct atgtgtgctg  23940
aagccatcgt tgcggggctg tctgtagaga ccctggaggg cacgacactg gaggtgggct  24000
gcagcgggga catgctcact atcaacggga aggcgatcat ctccaataaa gacatcctag  24060
ccaccaacgg ggtgatccac tacattgatg agctactcat cccagactca ggtaggccag  24120
gcctccgggg gccttggccc tgcctggccc accatctctt ctgccatcct ttgtggcggg  24180
ggagggaaa  ttcagagatc tttgggcgac ttccctgcct ggacccagct cacagcttct  24240
cggccactgc aaatgtgtgg gttgtgacca gactgatgtg tcttgagctt caggcttgca  24300
agtgcagtgg agaggcagtg gggagctatt gaaggggtct ggggacagac tcaatcacag  24360
aggcctttca gaagatctgc ctgctgtgca tgggcaaaga gggccacttg ctgacctcag  24420
agcatgtgct ttctcagtag tgcccaagct gtcccatggt cactgaccca gttagaatga  24480
ctgaatggac tttggcttgt gtctcattag gaatcctagc cccattctag tcttccagtg  24540
agatctgtcc atgagtgaag gaatctcaca ggaaaaaaca aaatgcttct atgggtgtgg  24600
ttgctggcct tatctacacc acagaagcca tcacacagac tgtctttctt cccattgtta  24660
gaatgtgccc tgaccaagca gcccacaggg cctgggacag aggctgatct ctgcctaact  24720
gagctcacct ctcctccctc tcctcctgac tggttagatt ttctaggtga ctgttcccct  24780
gatgacacaa gcccgctggg ccccagcagt gtttagaggg gttgttgact cacgagatga  24840
cattcctgct gatgtgtgtc atgccctggg gtggatgaat gataaatgaa aacagcgctt  24900
ttaacttttg aacccacttt ctccttcctt gtagccaaga cactatttga attggctgca  24960
gagtctgatg tgtccacagc cattgacctt tcagacaag  ccggcctcgg caatcatctc  25020
tctggaagtg agcggttgac cctcctggct cccctgaatt ctgtattcaa aggtaacatg  25080
gggaaggcat ccctgttaga ttgtccctgg aggcagcttc cccaccctg  tcacctccac  25140
aacactctcc gatttacagc accccatggg acattagaac ttccactcag ctcaaccaaa  25200
agcagatgtg acttcagcag aaacttcaga ggctctgttg tttcattagg cagtgcgagag 25260
aatgcctttg gggagccgtt cctcagaact caagacttga catctgggag gcagccgttc  25320
```

```
ctcagaactc aagacttgac atctgggaga gcagagcatt cccttgcctt tctatttgca    25380
gggtcacttg ccaatgtata gtcaagaggt cagagtgagg gtacagctga gctgcagccc    25440
caggaaggca gagaagggg ccaagttgtg tgcgtgcctg cccttccctc ttagggcaaa     25500
actccaaaca cccttgatta tctggatctt ctttaattct ccatagaaga taccagatgt    25560
taaggaatat tggcagcttc acttggtttc tcaatccctg tttccaaact caaggaggga    25620
tgggcttttt cactgtattt atctctcatc actctcttca ttgcaggagc acatctctct    25680
ggacctaacc atcacccttt cttgtagatg aaccctcc aattgatgcc catacaagga     25740
atttgcttcg gaaccacata attaaagacc agctggcctc taagtatctg taccatggac    25800
agaccctgga aactctgggc ggcaaaaaac tgagagtttt tgtttatcgt aatgtaagtt    25860
ctgggtccta aatcatgctc ctgggaagct ccttactgtg ggacttgtat tagtgtaaaa    25920
aaaaatgtcc tcaataagca ggagtttgca tgagaactgg ttgctgacaa ggaaggaaat    25980
aatttctgga aaatatagat aacaaaatga gatcctgcag aaggattgga atctcttttt    26040
ctggaggcct ttgagaataa accacacaat tatccaacct gtattgtgaa ggaataagtc    26100
cttcttgaat tcaggaatta acacctggga ggagggatgg agttcagact ctttctgagc    26160
ttatgagaag agaagccccc taaactaaaa tacagccctc cttggtccaa aaggtgcctt    26220
ctctcttctg ctgtatcttc tttgttttca aacccaacag ttaccctgga atcaaaaag    26280
gaagtacaac tcaacatagc tcttgcctgg gaccaaccag caccatttgg ctaaagatgg    26340
ttatcatctg ttaaacaaag aaataaataa atgggttcaa cgtatttatt tcaacattgt    26400
caatggacct catgtgtaac tgatattctc attatgggac ctctgtgtga ctttattggg    26460
gcctctctaa ccgttctttc cttaaggaag accatttatt gttttatttc ctggagaaaa    26520
tacatcattt tatcccagcc ttaataaccc atcccagtgt atactccttc atcttcatgg    26580
ataatgaccc tgctacatgc tctgaacaaa tcaggaggcc cctcgtggaa gtataaccag    26640
tcctttcttt ctctgtccct cttctgtgca gagcctctgc attgagaaca gctgcatcgc    26700
ggcccacgac aagaggggga ggtacggac cctgttcacg atggaccggg tgctgacccc    26760
cccaatgggg actgtcatgg atgtcctgaa gggagacaat cgctttaggt aattagttcc    26820
atccccgggt ggagcttctg cccagtggtc atgctggagt gggatgtggg gccccagcta    26880
tttgtcaagc tttcttctac cttggggatt caattaacac tagcagtgca ctgctgcgac    26940
cttccagact tgggatgggg aaaaggcaag ggtcgccttg aaagcttaca ttgggaagaa    27000
gggttacttc taagagtgta atcttcacat gcatgggaag cagggagggg ggactacatt    27060
tttatgactg aagtgcaagg aaaacatcac cctctcattg taaagctcca agtgagccaa    27120
gagcacatag tttacagtgc acgatgagcc tctcactctc tgcgcagtat ctgtttattg    27180
caactgaagc acccttgtga gtttgttttc ttgcccggct atctccattt ctgacttgct    27240
cattcacctt ggggtgctgt catattgaat gtttccctgt cactgacttc agccacctgc    27300
acaagggctt ggagaccaca cccctctgcc ctcccagaat catatccctg gaggctcagc    27360
tagtctctgg gtcagccata cctctgcct ttcttttccc tcctttctcc tgtggcctct    27420
gacgtctggc catttaacag agcttagcat ttttgctggg tggagagagc tggagcctgg    27480
aatcactccc tctttgtgca tacggagggc atgaaaacca aggtgtgtgc attccagtgg    27540
cctggactct actatcctca gtggtgaggt atttaaggaa atacctctc agcgtggtga    27600
ggtatttaag gaaaatacct gttgacaggt gacatttct gtgtgtgtat ctacagcatg     27660
```

```
ctggtagctg ccatccagtc tgcaggactg acggagaccc tcaaccggga aggagtctac    27720
acagtctttg ctcccacaaa tgaagccttc cgagccctgc caccaagaga acggagcaga    27780
ctcttgggta aagaccaact taagtacacg tctccatttt tctaaagtag tgatccctca    27840
gggccccagc agcaaacagt tggcacatca aggattgact tgaagggatt ttatgacaag    27900
actattagtg aaagagtggg cgggactaaa ggaactagca aaggatgagg ccaaccaggg    27960
actagcaacc ctgggaagcc tttactaccc ctaggcctgg gggaatggga ggatgagagc    28020
aggaaccagg gaggtcatga gccttggaca agggcacaga acagcagcca gagccatgtg    28080
cagccagcca ctgtcagaac catgcaaggg ggaccactca gcgccccagc ctccctctca    28140
gacagttgcc atctgggtct cttgttggct gatgcgagag caggagggag cccactgatg    28200
cagttcatag agctcagcct cctgggcagg aaaccgggca gagaggagta gaaaagaatt    28260
aagggtggct gcgaccagcc cagtcactga ggcacgtttc ccactggaga cctatgagca    28320
cagtgataat aaagccagtt acctgcactg actatccctc cagacaaaag ctttcccaag    28380
aagttagtca tggctctgag agatctagtt gaggatgttt ggcaggggat ctagtggtta    28440
cgggtggcta agaaaaatga ggaaggtaag agtatcttgc agcctgtgtt gggaggatta    28500
aataggatgc cacacacagg gccaggcaga cagcctggtc agtaatagcc atgacgatgg    28560 gggcggggggg agcaggaatg ggagttgcag tgtttagctc agatgcatgc ctgtgagaga    28620
tgcttccact ctcacagaaa gatgagacca aggaaaagga ggaggaagag gaaggacctt    28680
gacaaacctt ggggcccaca ttgtctacac ctccttcct gctctagagc agaatagaaa    28740
gttcaggttg caggcagctc taagttgaat tcgtgtcctg tttaattttc tttattgcta    28800
aatgaatgcc tgtgtctgtg atgctgacgt atgttcctaa ggagagggga gaagttcatt    28860
ctgaacataa acttttcatc ctctctctgt ccagcaagaa tggaatattc cccaagtggc    28920
ctgagccagc ttggctttct ttttgttttc aattatgtgg gagttgagga gggggatggg    28980
aaaagcttcc caaacacacc ctcccccagg cctgaggcac ccctggggga cagagagtgt    29040
tagaggttgg tacaggtgtt agagatattg aaaggacatc ccatgcaccc caggggctgg    29100
tgtggctctg tacttccagg caatattttg tggaagggga accttgtcag ctccaggttg    29160
tggatgtttg aaaatcagtt ggtacccagt ggctccatcc tctggcaggc atgtggattt    29220
gtcaataacc aagtgaactc tccaaaataa gttaaaactt cctcccttct cagtttcaag    29280
atgctggaaa tagctgttca taagccctgg ggaaatttag ccctttggct ggtaatggga    29340
gtatccgaga tgagagggca gctggaaact ttcggaatga cctcccacac ttaatttggg    29400
aaatgcctct gcacctttat gggcaaccag atgcctgccc cagttgctgg agacactgat    29460
gtgggctgaa aggaatgctg agacgtgacg aggagagatg ctgcggaggg aatatccccc    29520
tcagccctga cctcatcggc tccatggctc ctccacagta cagctgtcta ctctttaag    29580 ttctcccttc aggaaatagc catctcaaac agaatgtgca tttgagggca gaatgtgtaa    29640
atattgcact actgtgttat aaccgtcagg agccatgctg atgatgaaac gtcccagatg    29700
ccggtgctgg aaaggtccct ggcttttccaa gcaaatattt atctcatgga acatgagtc    29760 atactcacag aggagtatgg attaactcct tctcagcagc cagggagccc agcatcccag    29820
acagcatatt taacccagag gccaactgac tgctggggca gatttgtggt catgaacatg    29880
tgctttgtgt cctctgacca ttagacagat tgtgggtcac aacgttgagt atacagtggg    29940
agcttaataa gtgcttattc cctgggcagg gagttcttca tttcaggggt gaccacttac    30000
atcttctcct ctgggccctc cttgaccagg ctaattacca ttcttgggat taactctatc    30060
```

| | | | | |
|---|---|---|---|---|
| tccttttccc | gcaacctgca | ggagatgcca | aggaacttgc | caacatcctg | aaataccaca | 30120 |
| ttggtgatga | aatcctggtt | agcggaggca | tcggggccct | ggtgcggcta | aagtctctcc | 30180 |
| aaggtgacaa | gctggaagtc | agcttggtaa | gtgtcctgca | aatcaaaggc | tggctaaatt | 30240 |
| tccccagggc | agggctccag | gacatatctc | accccagga | tggaattata | cacacacaac | 30300 |
| cttcaagttg | cagcccgaat | ctctgagtgt | aattcgtcca | agaaaaaga | gaaaagagaa | 30360 |
| gagggtcttc | agggaaatca | agtgagatca | tagttagaca | tgagtaagaa | cttccagatt | 30420 |
| tacaagggaa | tagagcatct | gatttggcat | ctgagagagg | ctattagatc | ttccttctct | 30480 |
| taaggaggtt | gtaggcaact | agttatgtga | ctgaagagat | cagtctgtac | tcacaccatc | 30540 |
| ccacccccca | aacccagggc | ttcactgagt | tgtaccatga | accagaccat | cccaagaggc | 30600 |
| tttttgagtt | ctgacacttg | ctctgtgagc | cttcccttgc | tctgcacatt | gatgatataa | 30660 |
| ctttgtaact | gcactaagag | tgttcctaaa | gcagatagcc | agccgagctc | cagaaatctc | 30720 |
| cctggctgca | cctgcagagg | ccactgaccc | ctctgtggag | ggaccgctct | tcagtgtgtg | 30780 |
| gctggcttct | actctctgct | cctctctctt | ggtcttcagc | catccattgc | tcaccagttt | 30840 |
| ctcacgagga | gcataggaag | atatgcatgt | agggaggtag | gcacggggat | gacttgtttg | 30900 |
| actttagcag | gtcattcaag | aatctcctcg | cacctggttt | cagatgctgg | ggtcctgtct | 30960 |
| gtcacaggct | tctgtgcctc | ctaccccctt | gagtttgtca | catggccctt | caggaaggcc | 31020 |
| tgagatagat | ttgccctggg | tgggcctcct | atgagaaaat | cttaagtgag | gcacccaggc | 31080 |
| aaaatggaaa | gagccttttg | cccagagcag | gaagcctgtc | ttccatttcc | agctgttcca | 31140 |
| cctacttagc | ttaaaagagg | cacttcgcct | gtcttcagtc | tcagtctcag | tctcctcttc | 31200 |
| tgtggaatgg | gacaataata | tctactctcc | ttatcataca | ctgctgtgag | gactgagtgg | 31260 |
| atcacacaaa | aaagcattat | gtaaattgca | aagtgctaaa | tccacacagg | agatttgaat | 31320 |
| taatccacca | cactgaaggt | ctgtcaaggg | cagggactgt | ttcattcacc | agagtatccc | 31380 |
| cagtctaaca | caggacttgg | catatgaaaa | gtgttcagta | ggccgggtgc | agtggctcat | 31440 |
| gcctgtaatc | ccagcacttt | gggaggccaa | agtgggcgga | tcatctgagg | tcaggagttc | 31500 |
| aagtccagcc | tggccaacgt | ggtgaaacca | catctctact | aaaaatacaa | aattagctgg | 31560 |
| gcgtggtggc | acatgcctgt | aatcacagct | actctggagg | ctgaggcagg | agaatcactt | 31620 |
| gaacccagga | ggcggaggtt | gcagtgagtc | gagatcatgc | cactgcactc | cagcctgggc | 31680 |
| gacaagattg | aaactccatc | tcaaaaacaa | agaacaagga | aaaaacgaa | aactgttcag | 31740 |
| taaacacttg | ctgaatgaat | aaaataaata | tataaatgta | taaataaatg | ctctactttc | 31800 |
| aaccactact | ctgtttttct | tttagaaaaa | caatgtggtg | agtgtcaaca | aggagcctgt | 31860 |
| tgccgagcct | gacatcatgg | ccacaaatgg | cgtggtccat | gtcatcacca | atgttctgca | 31920 |
| gcctccaggt | aagtgtcgca | tccccactga | ctctgcagcc | agtccttttc | ttcatgtggc | 31980 |
| agttggtgga | gagaagaaaa | actgttctaa | acaatgatga | gaataacatg | taattgtgat | 32040 |
| agttaaactg | tgcctatgtg | actgattgca | gagtgaattg | ggagctgttg | gttttgaatg | 32100 |
| caccacacta | aggaatgtga | ggacacattg | ctctttgcgg | agttgcccag | ctatattagc | 32160 |
| tccccctcgga | cacagcccag | ttttctgtat | tcgcgtggat | gctgtccgcg | cgattcccag | 32220 |
| cactcctctt | acagcatctc | acctcagtgt | atgttccttg | cctccagtgc | agttgaacct | 32280 |
| cagtcctgcc | tctcctcatg | tgtgcattca | cctttcttgg | tgctctctcc | ccatgggcca | 32340 |
| agttctacca | tgagttatga | aacattatgg | agaaaacatg | tctttggaaa | tgtgagccag | 32400 |

-continued

| | |
|---|---|
| aaagcccacc agtgccctc agtcacggtt gttatgaatg acatgctaat ggtttcactc | 32460 |
| tggtcaaacc tgccttttct ttcctcttca gccaacagac ctcaggaaag aggggatgaa | 32520 |
| cttgcagact ctgcgcttga gatcttcaaa caagcatcag cgttttccag ggtaagatgc | 32580 |
| ctgctaggtt tgccgcctagc ctgagcagcc tcaggtcctc tgtttgggcc atagaggagc | 32640 |
| ctctccagcc cctgtcttcc ttggctgctc cccagggctc tcttaaaact tctccccact | 32700 |
| cccactgagg catcctcagc cccagcctgt gtcaaattca gagtaaagaa ccaaggcaac | 32760 |
| tccctggctt tcatgggcca aagcgcaggc tttcacaccg aggcctctga gcctcagatc | 32820 |
| atggggaagt cactgctgga gagaacagac atagctctgg aagccatctg cccaagaggg | 32880 |
| cagcccatcc caagttcatc ttacagtggc caggcctgcc ctgagccggg gcctctgggt | 32940 |
| cactcttctg ctgtccatgg cattgcccat cctgggtgag gctggggctc tcctgggcac | 33000 |
| tgtatgtatt ctggatacag ggatactggg ctcgctatgt gtgtggagcc atcccttcct | 33060 |
| tgccccagcc ccacctccct ctcaaaccct ctctggctct ttctgagctt cctttcctgc | 33120 |
| tccccagctt gcccagtgct cagtgcccca cttggctctt ttgctacttc gggtcaggtg | 33180 |
| gagcctcttg ggaatgtgaa gtgccttaca gaaagattgc acttcaagag gagaggctgc | 33240 |
| agggagccat cctaaaccca gaggcctgga gcttactgtg tcactttact tttgtacaca | 33300 |
| ggggtctcct tagtgccctc gagaaggatt cttggccctg agcttctact cctgaggcca | 33360 |
| cctctgtgca gccccagctc cctcaactct aggctgtagt ctcagtggga aagcctggct | 33420 |
| tgggggtctc ctaggaatgt ccacctgaag gcacacttga tagggcttg cacaacttat | 33480 |
| gtctgccaag gccacctgag gaactccctg gtgcctataa gttccacctt ccccttcctc | 33540 |
| ttcctcgccc cagcattttt tctgagtagg ggtggcaatg ggcaaagcca ttgtcataag | 33600 |
| cagttgcagg tataactttc actagaaaac ctgacacctt gtgttttctt tcaggcttcc | 33660 |
| cagaggtctg tgcgactagg tgagtctggt ctgggtttga agtcattgca gacctgttta | 33720 |
| ggccttaccc ccaagcaagc ccaagcctgc catctgctgt atatagataa gaacatcatg | 33780 |
| gtgcagtaaa agaagcctgg cctttggagt cagaacagca gggtgacttg gggtcagacc | 33840 |
| cagagcaccc catttccttc tctgtaagat gaggataata agagtaacaa ccttttaggg | 33900 |
| ttaaggtgag ttttcagctt aggaagtctg ggaatattgc aaagggcttg gcaggaaccc | 33960 |
| atggtgagga tctagttcca agttgatagg tacagaaaac cagaacatcg ggccttgagt | 34020 |
| aaagagtgaa gtttcacaaa ccacaaagca cctgctatgt gcaggagagc atggcagaag | 34080 |
| gaggctgctt ggccctggtc cttgagattc tgacagtgtc ctagacagac atggggagat | 34140 |
| ctgcacctat ttgacgttac caacttctct tttttcagccc ctgtctatca aaagttatta | 34200 |
| gagaggatga agcattagct tgaagcacta caggaggaat gcaccacggc agctctccgc | 34260 |
| caatttctct cagatttcca cagagactgt ttgaatgttt tcaaaaccaa gtatcacact | 34320 |
| ttaatgtaca tgggccgcac cataatgaga tgtgagcctt gtgcatgtgg gggaggaggg | 34380 |
| agagagatgt acttttaaaa tcatgttccc cctaaacatg gctgttaacc cactgcatgc | 34440 |
| agaaacttgg atgtcactgc ctgacattca cttccagaga ggacctatcc caaatgtgga | 34500 |
| attgactgcc tatgccaagt ccctggaaaa ggagcttcag tattgtgggg ctcataaaac | 34560 |
| atgaatcaag caatccagcc tcatgggaag tcctggcaca gttttgtaa agcccttgca | 34620 |
| cagctggaga aatggcatca ttataagcta tgagttgaaa tgttctgtca aatgtgtctc | 34680 |
| acatctacac gtggcttgga ggcttttatg gggccctgtc caggtagaaa agaaatggta | 34740 |
| tgtagagctt agatttccct attgtgacag agccatggtg tgtttgtaat aataaaacca | 34800 | aagaaacata 34810

<210> SEQ ID NO 52
<211> LENGTH: 683
<212> TYPE: PRT
<213> ORGANISM: Artificial Sequence
<220> FEATURE:
<223> OTHER INFORMATION: gene protein product

<400> SEQUENCE: 52

```
Met Ala Leu Phe Val Arg Leu Ala Leu Ala Leu Ala Leu
1               5                   10              15

Gly Pro Ala Ala Thr Leu Ala Gly Pro Ala Lys Ser Pro Tyr Gln Leu
            20                  25                  30

Val Leu Gln His Ser Arg Leu Arg Gly Arg Gln His Gly Pro Asn Val
        35                  40                  45

Cys Ala Val Gln Lys Val Ile Gly Thr Asn Arg Lys Tyr Phe Thr Asn
    50                  55                  60

Cys Lys Gln Trp Tyr Gln Arg Lys Ile Cys Gly Lys Ser Thr Val Ile
65                  70                  75                  80

Ser Tyr Glu Cys Cys Pro Gly Tyr Glu Lys Val Pro Gly Glu Lys Gly
                85                  90                  95

Cys Pro Ala Ala Leu Pro Leu Ser Asn Leu Tyr Glu Thr Leu Gly Val
            100                 105                 110

Val Gly Ser Thr Thr Thr Gln Leu Tyr Thr Asp Arg Thr Glu Lys Leu
        115                 120                 125

Arg Pro Glu Met Glu Gly Pro Gly Ser Phe Thr Ile Phe Ala Pro Ser
130                 135                 140

Asn Glu Ala Trp Ala Ser Leu Pro Ala Glu Val Leu Asp Ser Leu Val
145                 150                 155                 160

Ser Asn Val Asn Ile Glu Leu Leu Asn Ala Leu Arg Tyr His Met Val
                165                 170                 175

Gly Arg Arg Val Leu Thr Asp Glu Leu Lys His Gly Met Thr Leu Thr
            180                 185                 190

Ser Met Tyr Gln Asn Ser Asn Ile Gln Ile His His Tyr Pro Asn Gly
        195                 200                 205

Ile Val Thr Val Asn Cys Ala Arg Leu Leu Lys Ala Asp His His Ala
    210                 215                 220

Thr Asn Gly Val Val His Leu Ile Asp Lys Val Ile Ser Thr Ile Thr
225                 230                 235                 240

Asn Asn Ile Gln Gln Ile Ile Glu Ile Glu Asp Thr Phe Glu Thr Leu
                245                 250                 255

Arg Ala Ala Val Ala Ala Ser Gly Leu Asn Thr Met Leu Glu Gly Asn
            260                 265                 270

Gly Gln Tyr Thr Leu Leu Ala Pro Thr Asn Glu Ala Phe Glu Lys Ile
        275                 280                 285

Pro Ser Glu Thr Leu Asn Arg Ile Leu Gly Asp Pro Glu Ala Leu Arg
    290                 295                 300

Asp Leu Leu Asn Asn His Ile Leu Lys Ser Ala Met Cys Ala Glu Ala
305                 310                 315                 320

Ile Val Ala Gly Leu Ser Val Glu Thr Leu Glu Gly Thr Thr Leu Glu
                325                 330                 335

Val Gly Cys Ser Gly Asp Met Leu Thr Ile Asn Gly Lys Ala Ile Ile
            340                 345                 350
```

```
Ser Asn Lys Asp Ile Leu Ala Thr Asn Gly Val Ile His Tyr Ile Asp
        355                 360                 365

Glu Leu Leu Ile Pro Asp Ser Ala Lys Thr Leu Phe Glu Leu Ala Ala
    370                 375                 380

Glu Ser Asp Val Ser Thr Ala Ile Asp Leu Phe Arg Gln Ala Gly Leu
385                 390                 395                 400

Gly Asn His Leu Ser Gly Ser Glu Arg Leu Thr Leu Leu Ala Pro Leu
            405                 410                 415

Asn Ser Val Phe Lys Asp Gly Thr Pro Ile Asp Ala His Thr Arg
        420                 425                 430

Asn Leu Leu Arg Asn His Ile Ile Lys Asp Gln Leu Ala Ser Lys Tyr
        435                 440                 445

Leu Tyr His Gly Gln Thr Leu Glu Thr Leu Gly Gly Lys Lys Leu Arg
    450                 455                 460

Val Phe Val Tyr Arg Asn Ser Leu Cys Ile Glu Asn Ser Cys Ile Ala
465                 470                 475                 480

Ala His Asp Lys Arg Gly Arg Tyr Gly Thr Leu Phe Thr Met Asp Arg
                485                 490                 495

Val Leu Thr Pro Pro Met Gly Thr Val Met Asp Val Leu Lys Gly Asp
            500                 505                 510

Asn Arg Phe Ser Met Leu Val Ala Ala Ile Gln Ser Ala Gly Leu Thr
        515                 520                 525

Glu Thr Leu Asn Arg Glu Gly Val Tyr Thr Val Phe Ala Pro Thr Asn
    530                 535                 540

Glu Ala Phe Arg Ala Leu Pro Pro Arg Glu Arg Ser Arg Leu Leu Gly
545                 550                 555                 560

Asp Ala Lys Glu Leu Ala Asn Ile Leu Lys Tyr His Ile Gly Asp Glu
                565                 570                 575

Ile Leu Val Ser Gly Gly Ile Gly Ala Leu Val Arg Leu Lys Ser Leu
            580                 585                 590

Gln Gly Asp Lys Leu Glu Val Ser Leu Lys Asn Asn Val Val Ser Val
        595                 600                 605

Asn Lys Glu Pro Val Ala Glu Pro Asp Ile Met Ala Thr Asn Gly Val
    610                 615                 620

Val His Val Ile Thr Asn Val Leu Gln Pro Pro Ala Asn Arg Pro Gln
625                 630                 635                 640

Glu Arg Gly Asp Glu Leu Ala Asp Ser Ala Leu Glu Ile Phe Lys Gln
                645                 650                 655

Ala Ser Ala Phe Ser Arg Ala Ser Gln Arg Ser Val Arg Leu Ala Pro
            660                 665                 670

Val Tyr Gln Lys Leu Leu Glu Arg Met Lys His
        675                 680
```

<210> SEQ ID NO 53
<211> LENGTH: 15
<212> TYPE: DNA
<213> ORGANISM: Artificial Sequence
<220> FEATURE:
<223> OTHER INFORMATION: #TGFBI R124NI

<400> SEQUENCE: 53
cacggaccgc acgga                                                    15

<210> SEQ ID NO 54
<211> LENGTH: 15
<212> TYPE: DNA

```
<213> ORGANISM: Artificial Sequence
<220> FEATURE:
<223> OTHER INFORMATION: #TGFBI R124H

<400> SEQUENCE: 54
cacggaccac acgga                                                     15

<210> SEQ ID NO 55
<211> LENGTH: 15
<212> TYPE: DNA
<213> ORGANISM: Artificial Sequence
<220> FEATURE:
<223> OTHER INFORMATION: #TGFBI R555NI

<400> SEQUENCE: 55
caccaagaga acgga                                                     15

<210> SEQ ID NO 56
<211> LENGTH: 15
<212> TYPE: DNA
<213> ORGANISM: Artificial Sequence
<220> FEATURE:
<223> OTHER INFORMATION: #TGFBI R555W

<400> SEQUENCE: 56
accaagagaa cagag                                                     15

<210> SEQ ID NO 57
<211> LENGTH: 20
<212> TYPE: DNA
<213> ORGANISM: Artificial Sequence
<220> FEATURE:
<223> OTHER INFORMATION: #TGFBI 124F

<400> SEQUENCE: 57
tccaccacca ctcagctgta                                                20

<210> SEQ ID NO 58
<211> LENGTH: 19
<212> TYPE: DNA
<213> ORGANISM: Artificial Sequence
<220> FEATURE:
<223> OTHER INFORMATION: #TGFBI 124R

<400> SEQUENCE: 58
ccatctcagg cctcagctt                                                 19

<210> SEQ ID NO 59
<211> LENGTH: 22
<212> TYPE: DNA
<213> ORGANISM: Artificial Sequence
<220> FEATURE:
<223> OTHER INFORMATION: #TGFBI 555F

<400> SEQUENCE: 59
acacagtctt tgctcccaca aa                                             22

<210> SEQ ID NO 60
<211> LENGTH: 28
<212> TYPE: DNA
<213> ORGANISM: Artificial Sequence
<220> FEATURE:
<223> OTHER INFORMATION: #TGFBI 555R
```

```
<400> SEQUENCE: 60
acttaagttg gtctttaccc aagagtct                                              28
```